US009955692B2

(12) United States Patent
Soergel et al.

(10) Patent No.: US 9,955,692 B2
(45) Date of Patent: May 1, 2018

(54) PYRAZOLES FOR CONTROLLING INVERTEBRATE PESTS

(71) Applicant: BASF SE, Ludwigshafen (DE)

(72) Inventors: Sebastian Soergel, Ludwigshafen (DE); Daniel Saelinger, Ludwigshafen (DE); Birgit Gockel, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days. days.

(21) Appl. No.: 15/114,974

(22) PCT Filed: Jan. 30, 2015

(86) PCT No.: PCT/EP2015/051968
§ 371 (c)(1),
(2) Date: Jul. 28, 2016

(87) PCT Pub. No.: WO2015/114106
PCT Pub. Date: Aug. 6, 2015

(65) Prior Publication Data
US 2016/0345581 A1    Dec. 1, 2016

(30) Foreign Application Priority Data

Jan. 31, 2014  (EP) .................................... 14153482

(51) Int. Cl.
*A01N 43/58* (2006.01)
*C07D 403/12* (2006.01)
*A01N 43/36* (2006.01)
*A01N 43/56* (2006.01)

(52) U.S. Cl.
CPC ............ *A01N 43/58* (2013.01); *C07D 403/12* (2013.01); *A01N 43/36* (2013.01); *A01N 43/56* (2013.01)

(58) Field of Classification Search
CPC ................................ A01N 43/56; A01N 43/36
See application file for complete search history.

(56) References Cited

U.S. PATENT DOCUMENTS 9,439,427 B2 *  9/2016  Defieber .............. C07D 401/14
2010/0305124 A1   12/2010  Fusslein et al.

FOREIGN PATENT DOCUMENTS

| WO | WO 2009027393 | 3/2009 |
| WO | WO 2010034737 | 4/2010 |
| WO | WO 2010034738 | 4/2010 |
| WO | WO 2010112177 | 10/2010 |
| WO | WO 2013156318 | 10/2013 |

OTHER PUBLICATIONS

International Preliminary Report on Patentability, issued in PCT/EP2015/051968, dated Aug. 2, 2016.
International Search Report, issued in PCT/EP2015/051968, dated Mar. 10, 2015.

* cited by examiner

*Primary Examiner* — Johann R Richter
*Assistant Examiner* — Danielle Sullivan
(74) *Attorney, Agent, or Firm* — Brinks Gilson & Lione

(57) ABSTRACT

The present invention relates to novel pyrazoles of formula I. Moreover, the invention relates to processes and intermediates for preparing the pyrazoles of formula I, and also to active compound combinations comprising them, to compositions comprising them, and to their use for protecting growing plants from attack or infestation by invertebrate pests. Furthermore, the invention relates to methods of applying such compounds. The present invention also relates to seed comprising such compounds.

22 Claims, No Drawings

PYRAZOLES FOR CONTROLLING INVERTEBRATE PESTS

This application is a National Stage application of International Application No. PCT/EP2015/051968, filed Jan. 30, 2015. This application also claims priority under 35 U.S.C. § 119 to European Patent Application No. 14153482.6, filed Jan. 31, 2014.

The present invention relates to novel pyrazoles of formula I. Moreover, the invention relates to processes and intermediates for preparing the pyrazoles of formula I, and also to active compound combinations comprising them, to compositions comprising them, and to their use for protecting growing plants from attack or infestation by invertebrate pests. Furthermore, the invention relates to methods of applying such compounds. The present invention also relates to seed comprising such compounds.

Invertebrate pests and in particular arthropods and nematodes destroy growing and harvested crops and attack wooden dwelling and commercial structures, thereby causing large economic loss to the food supply and to property. There is an ongoing need for new agents for combating invertebrate pests such as insects, arachnids and nematodes.

WO 2009/027393, WO 2010/034737, WO 2010/034738, and WO 2010/112177 describe derivatives of N-arylamides, derived from pyrazole carboxylic acids. These compounds are mentioned to be useful for combating invertebrate pests.

Nevertheless, there remains a need for highly effective and versatile agents for combating invertebrate pests. It is therefore an object of the present invention to provide compounds having a good pesticidal activity and showing a broad activity spectrum against a large number of different invertebrate pests, especially against difficult to control pests, such as insects.

It has been found that these objects can be achieved by compounds of formula I as depicted and defined below, and by their stereoisomers, salts, tautomers and N-oxides, in particular their agriculturally acceptable salts.

In a first aspect, the present invention relates to compounds of formula I

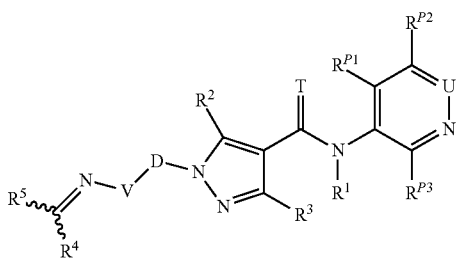

wherein

V is O, S or $NR^{1a}$, wherein $R^{1a}$ is selected from H, $C_1$-$C_{10}$-alkyl,
  $C_1$-$C_4$-haloalkyl, $C_3$-$C_{10}$-cycloalkyl, $C_3$-$C_{10}$-cycloalkylmethyl,
  $C_3$-$C_{10}$-halocycloalkyl, $C_2$-$C_{10}$-alkenyl, $C_2$-$C_{10}$-haloalkenyl, $C_2$-$C_{10}$-alkynyl, $C_1$-$C_{10}$-alkoxy-$C_1$-$C_4$-alkyl, $OR^a$, heterocyclyl, heterocyclyl-$C_1$-$C_4$-alkyl, phenyl, hetaryl, phenyl-$C_1$-$C_4$-alkyl and hetaryl-$C_1$-$C_4$-alkyl, wherein the ring in the six last mentioned radicals may be unsubstituted or may carry 1, 2, 3, 4 or 5 identical or different substituents selected from halogen, CN, $NO_2$, $C_1$-$C_4$-alkyl, $C_1$-$C_4$-haloalkyl, $C_1$-$C_4$-alkoxy and $C_1$-$C_4$-haloalkoxy, or wherein $R^{1a}$ and $R^4$ together with the carbon atom to which $R^4$ is bound and the nitrogen atom to which $R^{1a}$ is bound as well as the nitrogen atom between said carbon atom and said nitrogen atom form a 4- to 8-membered heterocycle, which contains the two nitrogen atoms as heteroatoms, and may further contain 1 or 2 heteroatoms which, independently of each other, are selected from $NR^B$, O, and S, wherein S may be oxidized, and/or wherein the heterocycle may be unsubstituted or may be partially or fully substituted by substituents which, independently of each other, are selected from $R^A$;

D is $C_1$-$C_8$-alkylene, $C_3$-$C_8$-cycloalkylene, $C_3$-$C_8$-heterocycloalkylene, $C_2$-$C_8$-alkenylene, $C_3$-$C_8$-cycloalkenylene, $C_3$-$C_8$-heterocycloalkenylene, or $C_2$-$C_8$-alkynylene, wherein D may be unsubstituted or may be partially or fully substituted by substituents which, independently of each other, are selected from $R^A$;

U is N or $CR^U$;

T is S, O or $NR^{1b}$, wherein Rib is selected from H, $C_1$-$C_{10}$-alkyl,
  $C_1$-$C_4$-haloalkyl, $C_3$-$C_{10}$-cycloalkyl, $C_3$-$C_{10}$-cycloalkylmethyl,
  $C_3$-$C_{10}$-halocycloalkyl, $C_2$-$C_{10}$-alkenyl, $C_2$-$C_{10}$-haloalkenyl, $C_2$-$C_{10}$-alkynyl, $C_1$-$C_{10}$-alkoxy-$C_1$-$C_4$-alkyl, $OR^a$, heterocyclyl, heterocyclyl-$C_1$-$C_4$-alkyl, phenyl, hetaryl, phenyl-$C_1$-$C_4$-alkyl and hetaryl-$C_1$-$C_4$-alkyl, wherein the ring in the six last mentioned radicals may be unsubstituted or may carry 1, 2, 3, 4 or 5 identical or different substituents selected from halogen, CN, $NO_2$, $C_1$-$C_4$-alkyl, $C_1$-$C_4$-haloalkyl, $C_1$-$C_4$-alkoxy and $C_1$-$C_4$-haloalkoxy;

$R^{P1}$, $R^{P2}$, $R^{P3}$, and $R^U$ are independently of each other selected from H, halogen, $C_1$-$C_4$-alkyl, $C_1$-$C_3$-haloalkyl, $C_1$-$C_4$-alkoxy, $C_1$-$C_3$-haloalkoxy, $C_1$-$C_4$-alkylthio, $C_1$-$C_3$-haloalkylthio, $C_1$-$C_4$-alkylsulfinyl, $C_1$-$C_3$-haloalkylsulfinyl, $C_1$-$C_4$-alkylsulfonyl, $C_1$-$C_3$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl or $C_1$-$C_4$-alkoxy-$C_1$-$C_4$-alkyl;

$R^1$ is H, CN, $C_1$-$C_{10}$-alkyl, $C_1$-$C_{10}$-haloalkyl, $C_3$-$C_{10}$-cycloalkyl, $C_3$-$C_{10}$-halocycloalkyl, $C_1$-$C_4$-alkoxy-$C_1$-$C_4$-alkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_1$-$C_5$-alkylen-CN, $OR^a$, $C_1$-$C_5$-alkylen-$OR^a$, $C(Y)R^b$, $C_1$-$C_5$-alkylen-$C(Y)R^b$, $C(Y)OR^c$, $C_1$-$C_5$-alkylen-$C(Y)OR^c$, $S(O)_2R^d$, $NR^eR^f$, $C_1$-$C_5$-alkylen-$NR^eR^f$, $C(Y)NR^gR^h$, $C_1$-$C_5$-alkylen-$C(Y)NR^gR^h$, $S(O)_nNR^eR^f$, $C(Y)NR^tNR^eR^f$, $C_1$-$C_5$-alkylen-$S(O)_2R^d$, $C_1$-$C_5$-alkylen-$S(O)_nNR^eR^f$, $C_1$-$C_5$-alkylen-$C(Y)NR^tN$-$R^eR^f$, phenyl, heterocyclyl, hetaryl, phenyl-$C_1$-$C_5$-alkyl, $C_3$-$C_{10}$-cycloalkyl-$C_1$-$C_5$-alkyl, heterocyclyl-$C_1$-$C_5$-alkyl and hetaryl-$C_1$-$C_5$-alkyl wherein the ring of the seven last mentioned radicals may be unsubstituted or may carry 1, 2, 3, 4 or 5 identical or different substituents selected from the radicals $R^y$ and $R^x$;

$R^2$ and $R^3$ are independently of each other selected from H, halogen, CN, $NO_2$, $C_1$-$C_{10}$-alkyl, $C_2$-$C_{10}$-alkenyl and $C_2$-$C_{10}$-alkynyl, wherein the 3 last mentioned radicals may be unsubstituted, may be partially or fully halogenated or may carry 1, 2 or 3 identical or different substituents $R^x$, or wherein $R^2$ and $R^3$ are further selected from $OR^a$, $SR^a$, $C(Y)R^b$, $C(Y)OR^c$, $S(O)R^d$, $S(O)_2R^d$, $NR^eR^f$, $C(Y)NR^gR^h$, heterocyclyl, hetaryl, $C_3$-$C_{10}$-cycloalkyl, $C_5$-$C_{10}$-cycloalkenyl and phenyl, wherein the five last mentioned radicals may be unsubstituted or may carry 1, 2, 3, 4 or 5 identical or different substituents selected from the radicals $R^y$ and $R^x$, and wherein $R^4$ is H, $C_1$-$C_6$-alkyl, $C_1$-$C_6$-alkyl-X, $C_3$-$C_6$-cycloalkyl or $C_3$-$C_6$-cycloalkyl-X, wherein X is selected from O, S, or $NR^B$, wherein the $C_1$-$C_6$-alkyl or $C_3$-$C_6$-cycloalkyl may be unsubstituted or may be partially or fully substituted by substituents which, independently of each other, are selected from $R^A$; and $R^5$ is $C_1$-$C_6$-alkyl, $C_1$-$C_6$-alkyl-X, $C_3$-$C_6$-cycloalkyl or $C_3$-$C_6$-cycloalkyl-X, wherein X is selected from O, S, or $NR^B$, wherein the $C_1$-$C_6$-alkyl or $C_3$-$C_6$-cycloalkyl may be unsubstituted or may be partially or fully substituted by substituents which, independently of each other, are selected from $R^A$, or wherein $R^4$ and $R^5$ together with the carbon atom to which they are bound form a 3- to 8-membered, saturated or unsaturated carbo- or heterocycle, which may contain 1, 2, or 3 heteroatoms which, independently of each other, are selected from $NR^B$, O, and S, wherein S may be oxidized and/or wherein the carbo- or heterocycle may be unsubstituted or may be partially or fully substituted by substituents which, independently of each other, are selected from $R^A$;

and wherein $R^A$ is halogen, $NO_2$, CN, $C_1$-$C_6$-alkyl, $C_1$-$C_6$-alkoxy, $C_1$-$C_6$-haloalkyl, $C_1$-$C_6$-haloalkoxy, $C_3$-$C_6$-cycloalkyl, $C_3$-$C_6$-cycloalkoxy, $C_3$-$C_6$-halocycloalkyl, $C_3$-$C_6$-halocycloalkoxy, $C_2$-$C_4$-alkenyl, $C_2$-$C_4$-alkynyl, $S(O)_nR^D$, =O, =S, =$NR^c$, =$NOR^C$, and =$NSR^C$; or wherein two $R^A$ bound to the same carbon atom or to adjacent carbon atoms together with the carbon atom(s) to which they are bound form a 3- to 6-membered, saturated or unsaturated carbo- or heterocycle, which may contain 1 or 2 heteroatoms which, independently of each other, are selected from $NR^B$, O, and S, wherein S may be oxidized;

and wherein $R^B$ is H, $C_1$-$C_2$-alkyl, $C_1$-$C_2$-haloalkyl, $C_1$-$C_2$-alkylcarbonyl, $C_1$-$C_2$-haloalkylcarbonyl, or $C_1$-$C_2$-alkoxycarbonyl;

$R^C$ is H, $C_1$-$C_4$-alkyl, $C_1$-$C_2$-haloalkyl, $C_3$-$C_6$-cycloalkyl, or $C_3$-$C_6$-halocycloalkyl;

$R^D$ is H, $C_1$-$C_4$-alkyl, $C_1$-$C_4$-haloalkyl, $C_3$-$C_6$-cycloalkyl, or $C_3$-$C_6$-halocycloalkyl, $C_1$-$C_4$-alkoxy, or $C_1$-$C_4$-haloalkoxy;

n is 0, 1, or 2;

Y is O or S;

$R^a$, $R^b$, $R^c$ are independently of each other selected from H, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, phenyl, hetaryl, phenyl-$C_1$-$C_4$-alkyl and hetaryl-$C_1$-$C_4$-alkyl, wherein the ring in the six last mentioned radicals may be unsubstituted or may carry 1, 2, 3, 4 or 5 substituents which, independently of each other, are selected from halogen, CN, $NO_2$, $C_1$-$C_4$-alkyl, $C_1$-$C_4$-haloalkyl, $C_1$-$C_4$-alkoxy and $C_1$-$C_4$-haloalkoxy;

$R^d$ is selected from $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, phenyl, hetaryl, phenyl-$C_1$-$C_4$-alkyl and hetaryl-$C_1$-$C_4$-alkyl, wherein the ring in the six last mentioned radicals may be unsubstituted or may carry 1, 2, 3, 4 or 5 substituents which are independently of each other selected from halogen, CN, $NO_2$, $C_1$-$C_4$-alkyl, $C_1$-$C_4$-haloalkyl, $C_1$-$C_4$-alkoxy and $C_1$-$C_4$-haloalkoxy; and wherein $R^e$ and $R^f$ are independently of each other selected from H, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, heterocyclyl, heterocyclyl-$C_1$-$C_4$-alkyl, heterocyclylcarbonyl, heterocyclylsulfonyl, phenyl, phenylcarbonyl, phenylsulfonyl, hetaryl, hetarylcarbonyl, hetarylsulfonyl, phenyl-$C_1$-$C_4$-alkyl and hetaryl-$C_1$-$C_4$-alkyl, wherein the ring in the twelve last mentioned radicals may be unsubstituted or may carry 1, 2, 3, 4 or 5 substituents which, independently of each other, are selected from halogen, CN, $NO_2$, $C_1$-$C_4$-alkyl, $C_1$-$C_4$-haloalkyl, $C_1$-$C_4$-alkoxy and $C_1$-$C_4$-haloalkoxy; or $R^e$ and $R^f$ together with the nitrogen atom to which they are bound form a 5- or 6-membered, saturated or unsaturated heterocycle, which may carry a further heteroatom being selected from O, S and N as a ring member atom and wherein the heterocycle may be unsubstituted or may carry 1, 2, 3, 4 or 5 substituents which are independently of each other selected from halogen, CN, $NO_2$, $C_1$-$C_4$-alkyl, $C_1$-$C_4$-haloalkyl, $C_1$-$C_4$-alkoxy and $C_1$-$C_4$-haloalkoxy;

and wherein $R^g$ and $R^h$ are independently of each other selected from H, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, phenyl, hetaryl, phenyl-$C_1$-$C_4$-alkyl and hetaryl-$C_1$-$C_4$-alkyl, wherein the ring in the six last mentioned radicals may be unsubstituted or may carry 1, 2, 3, 4 or 5 substituents which are independently of each other selected from halogen, CN, $NO_2$, $C_1$-$C_4$-alkyl, $C_1$-$C_4$-haloalkyl, $C_1$-$C_4$-alkoxy and $C_1$-$C_4$-haloalkoxy;

$R^i$ is selected from H, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl and phenyl-$C_1$-$C_4$-alkyl wherein the phenyl ring in the two last mentioned radicals may be unsubstituted or may carry 1, 2, 3, 4 or 5 substituents which are independently of each other selected from halogen, CN, $NO_2$, $C_1$-$C_4$-alkyl, $C_1$-$C_4$-haloalkyl, $C_1$-$C_4$-alkoxy and $C_1$-$C_4$-haloalkoxy;

$R^x$ is CN, $NO_2$, $C_1$-$C_4$-alkoxy, $C_1$-$C_4$-haloalkoxy, $S(O)_nR^d$, $S(O)_nNR^eR^f$, $C_1$-$C_{10}$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, 5- to 7-membered heterocyclyl, 5- or 6-membered hetaryl, phenyl, $C_3$-$C_6$-cycloalkoxy, 3- to 6-membered heterocyclyloxy and phenoxy, wherein the last 7 mentioned radicals may be unsubstituted or may carry 1, 2, 3, 4 or 5 identical or different radicals $R^y$; and $R^y$ is selected from halogen, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_nR^d$, $S(O)_nNR^eR^f$, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl, and the salts, stereoisomers, tautomers and N-oxides thereof.

In further aspects, the present invention relates to a composition and to an agricultural composition for combating animal pests comprising at least one compound of formula I. In still further aspects, the present invention relates to a method for combating or controlling invertebrate pests and to a method for protecting growing plants from attack or infestation by invertebrate pests. In another aspect, the present invention relates to seed comprising a compound of formula I, and in yet another aspect, the present invention relates to the use of the compounds of formula I for protecting growing plants from attack or infestation by invertebrate pests.

Further embodiments of the present invention can be found in the claims, the description and the examples. It is to be understood that the features mentioned above and those still to be illustrated below of the subject matter of the invention can be applied not only in the respective given combination but also in other combinations without leaving the scope of the invention.

In the compounds of formula I above, the wavy lines to the substituents $R^4$ and $R^5$ indicate that $R^4$ and $R^5$ may be present in both positions at the carbon atom of the carbon-nitrogen double bond, i.e. either in cis configuration or in trans configuration relative to V. Thus, two geometric isomers GISO-A and GISO-B as depicted below are covered by the compounds of formula I of the invention.

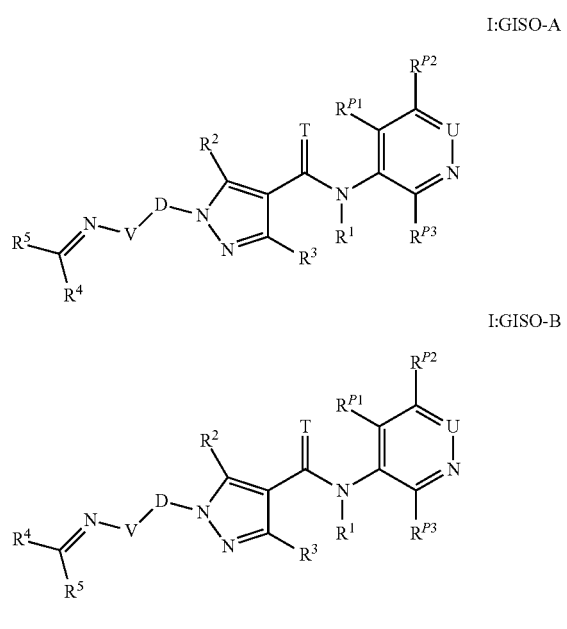

I:GISO-A

I:GISO-B

For reasons of clarity, it is referred to geometric isomer GISO-A only throughout the specification, but its description embraces the disclosure of the other geometric isomer GISO-B as well.

It is noted that, as used herein, the terms "geometric isomers" and "geometric isomerisation" in particular refer to "E/Z-isomers" and "E/Z-isomerisation" regarding the carbon-nitrogen double bond of the oxime, thiooxime or hydrazone group in the compounds of formula I, wherein the E and Z configurations are determined according to IUPAC applying the Cahn-Ingold-Prelog priority rules.

In case of carbon-nitrogen double bonds as present in the oxime, thiooxime or hydrazone group of the compounds of formula I of the invention, the energy barrier for E/Z-isomerisations is typically rather low, in particular if compared to the energy barrier for E/Z-isomerisations of carbon-carbon double bonds. Accordingly, if the geometric isomers GISO-A and GISO-B are e.g. provided in solution, they will typically be present in an equilibrium, wherein the geometric isomer, which is more stable, will be present in a higher proportion than the geometric isomer, which is less stable. For steric reasons, the E-isomers are often more stable than the Z-isomers, and will be present in excess. Therefore, it is a preferred embodiment of the invention that in the compounds of formula I, the ratio of the E-isomer to the Z-isomer is at least 50:50, preferably at least 70:30, more preferably at least 90:1, and most preferably at least 99:1. In certain particularly preferred embodiments, the compounds of formula I will be present in the form of the E-isomer.

In one embodiment, the present invention relates to compounds of formula I, wherein T is O, S or $NR^{1b}$. These compounds correspond to formula I.1, formula I.2 and formula I.3, respectively.

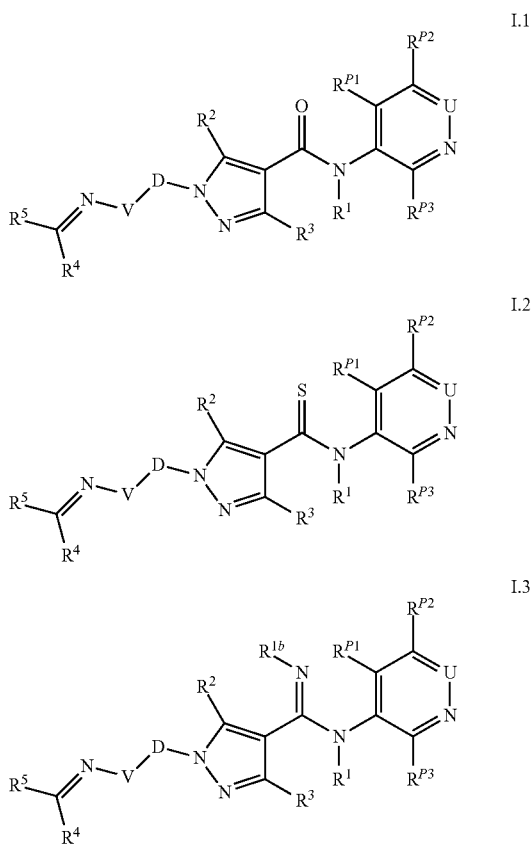

Compounds of formula I.1 are preferred according to the invention.

The compounds according to the invention can be prepared analogously to the synthesis routes described in WO 2009/027393 and WO 2010/034737 according to standard processes of organic chemistry.

Compounds of formula I.1, wherein T is O, can be prepared e.g. by reacting activated pyrazole carboxylic acid derivatives of formula II with a 3-aminopyridine, or 4-aminopyridazine of formula III (e.g. Houben-Weyl: "Methoden der organ. Chemie" [Methods of Organic Chemistry], Georg-Thieme-Verlag, Stuttgart, N.Y. 1985, Volume E5, pp. 941-1045).

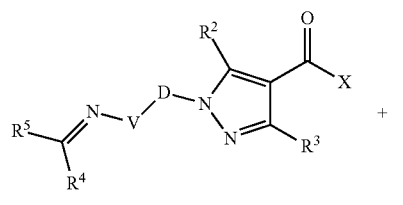

II

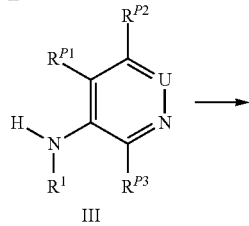

III

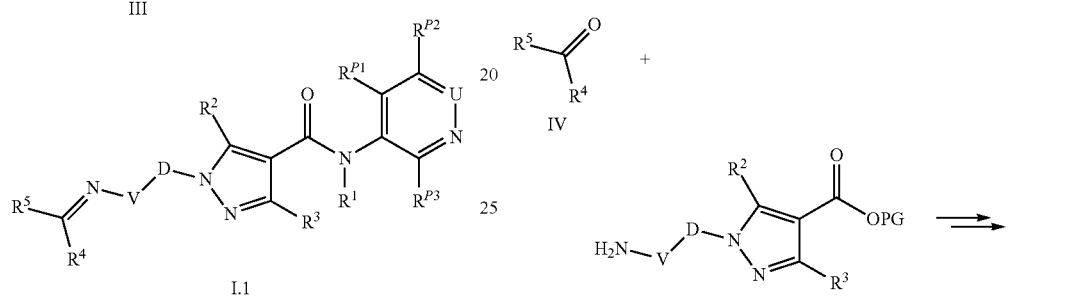

I.1

Compounds of formula I.1 wherein $R^1$ is different from hydrogen can also be prepared by alkylating the amides I.1, in which $R^1$ is hydrogen, using suitable alkylating agents in the presence of bases. The alkylation can be effected under standard conditions known from literature.

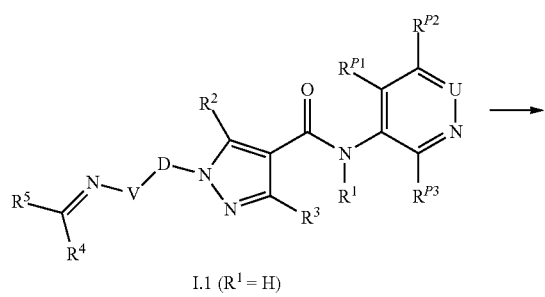

I.1 ($R^1$ = H)

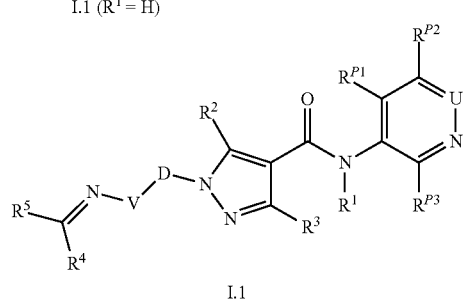

I.1

In formulae II and III, the radicals have the meanings mentioned above for formula I and in particular the meanings mentioned as being preferred, X is a suitable leaving group such as halogen, $N_3$, p-nitrophenoxy or pentafluorophenoxy and the like.

Activated pyrazole carboxylic acid derivatives of formula II are preferably halides, activated esters, anhydrides, azides, for example chlorides, fluorides, bromides, para-nitrophenyl esters, pentafluorophenyl esters, N-hydroxysuccinimides, hydroxybenzotriazol-1-yl esters.

The oxime, thiooxime or hydrazone group of the activated pyrazole carboxylic acid derivatives of formula II can be formed by reacting an aldehyde or ketone of formula IV with a protected pyrazole carboxylic acid derivative of formula V, wherein PG is a protecting group such as ethyl, tert-butyl, benzyl or the like. The resulting product may then be deprotected and transformed into the activated pyrazole carboxylic acid derivative of formula II. Methods of preparing compounds of formula II with V being O, V being S and V being $NR^{1a}$ are described in WO 2013/072882, J. Org. Chem. 48(20), p. 3531 (1983), and JP 2013/023476, respectively.

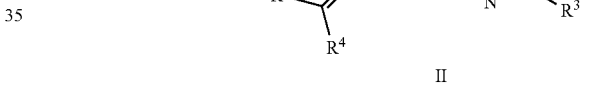

IV

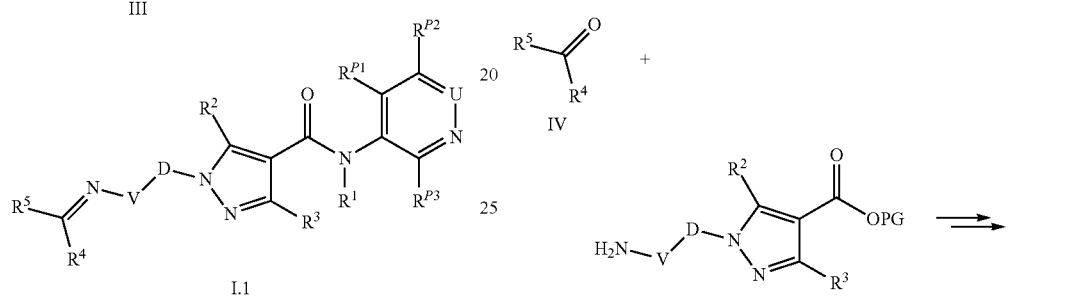

V

II

Alternatively, the oxime, thiooxime or hydrazone group of the activated pyrazole carboxylic acid derivatives of formula II can be formed by reacting an oxime, thiooxime or hydrazone of formula VI with a protected pyrazole carboxylic acid derivative of formula VII, wherein PG is a protecting group such as ethyl, tert-butyl, benzyl or the like, and wherein X is a leaving group such as chlorine, bromine, iodine, methylsulfonyloxy, 4-toluenesulfonyloxy or the like. The resulting product may then be deprotected and transformed into the activated pyrazole carboxylic acid derivative of formula II. A method of preparing oximes according to this procedure is e.g. described in J. Med. Chem, 28(7), p. 896 (1985).

VI

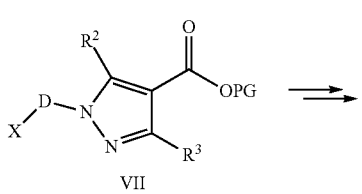

VII

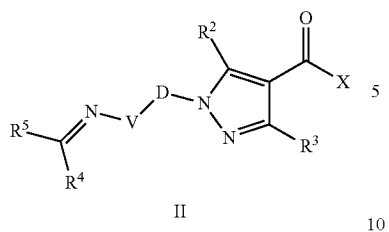

II

The compounds of formula IV and VI are known in the art or are commercially available or can be prepared by methods known in the literature.

The compounds of formula III, V, and VII are known in the art or are commercially available or can be prepared by methods known from the literature (cf. WO 05/040169; WO 08/074824; Journal of Fluorine chemistry 132(11), p. 995 (2011)).

Compounds of formula I.2, wherein T is S, can be prepared e.g. by reacting compounds of formula I.1 with 2,4-bis(4-methoxyphenyl)-1,3,2,4-dithiadiphosphetane-2,4-disulfide or $PS_5$ according to the method described in Synthesis 2003, p. 1929.

Compounds of formula I.3, wherein T is $NR^{1b}$, can be prepared e.g. via imine formation starting from the compounds of formula I.1.

In one embodiment, the present invention relates to compounds of formula I, wherein U is $CR^U$, preferably CH, or N. Compounds, wherein U is CH and U is N, correspond to formula I.A and formula I.B, respectively.

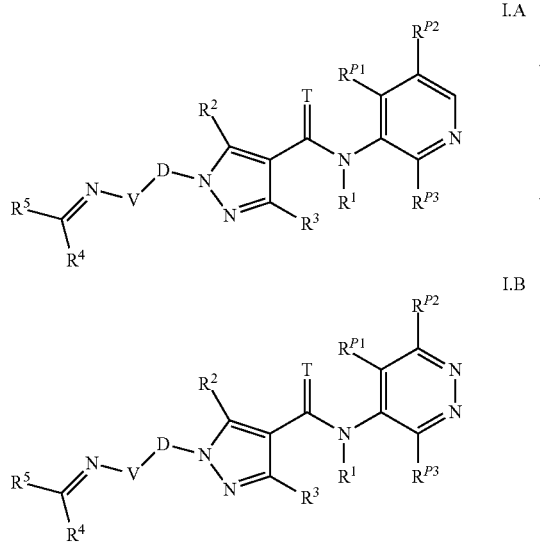

Compounds of formula I.B are particularly preferred according to the invention.

If $R^1$ is H, the compounds of formula I may be present in two or three tautomeric forms depending on the meaning of U. For example, if U is selected to be CH, as in the compounds of formula I.A, two tautomers T-A and T-B can be formed.

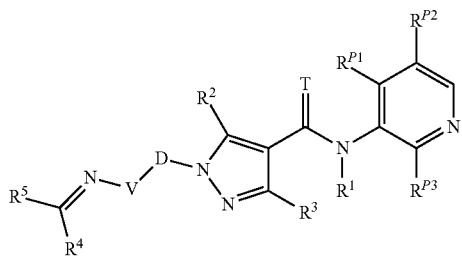

I.A($R^1$ = H):T-A

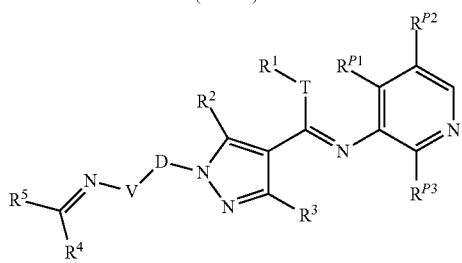

I.A($R^1$ = H):T-B

If U is selected to be N, as in the compounds of formula I.B, three tautomers T-A, T-B and T-C can be formed.

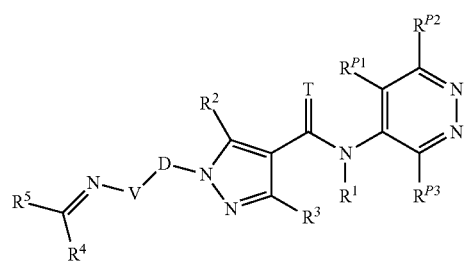

I.B($R^1$ = H):T-A

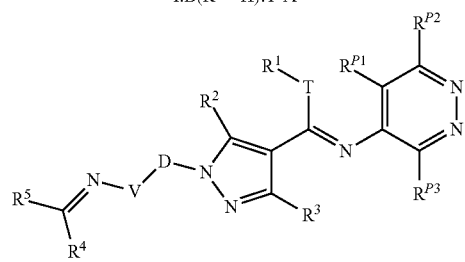

I.B($R^1$ = H):T-B

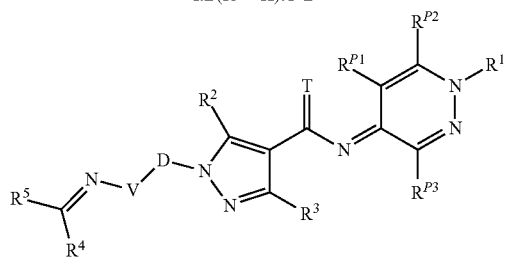

I.B($R^1$ = H):T-C

For reasons of clarity it is referred to tautomer T-A only throughout the specification, but its description embraces the disclosure of the other tautomers as well.

If $R^1$ is different from H, the compounds of formula I may be present in two or three isomeric forms depending on the meaning of U. For example, if U is selected to be CH, as in the compounds of formula I.A, two structural isomers ISO-A and ISO-B can be formed.

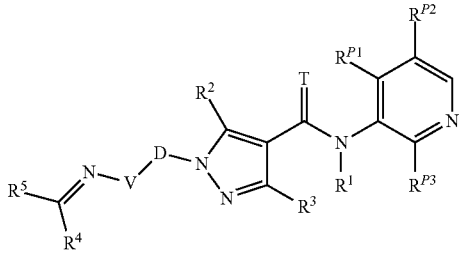

I.A(R¹ ≠ H):ISO-A

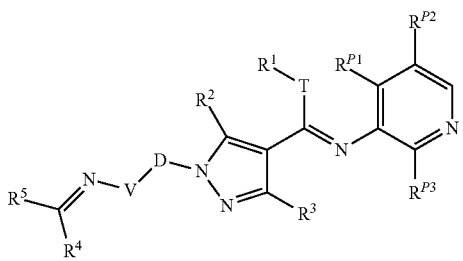

I.A(R¹ ≠ H):ISO-B

If U is selected to be N, as in the compounds of formula I.B, three structural isomers ISO-A, ISO-B and ISO-C can be formed.

I.B(R¹ ≠ H):ISO-A

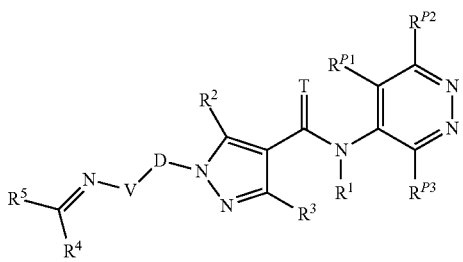

I.B(R¹ ≠ H):ISO-B

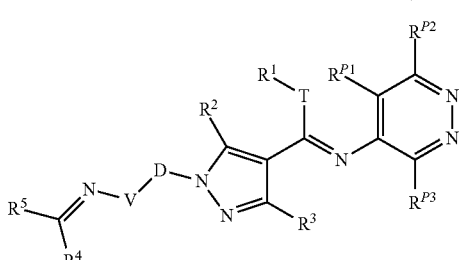

I.B(R¹ ≠ H):ISO-C

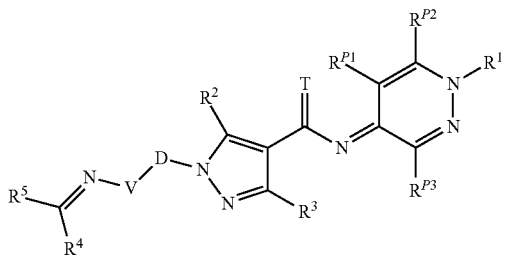

It is preferred according to the present invention, that the compounds of formula I are present in the form of the structural isomers ISO-A. However, the compounds of formula I may also be present in the form of the structural isomers ISO-B or ISO-C or the in form of mixtures of two or more of the structural isomers ISO-A, ISO-B and ISO-C. For reasons of clarity it is referred to the structural isomer ISO-A only throughout the specification, but its description embraces the disclosure of the other structural isomers as well.

Isomers ISO-C can be obtained by alkylation of compounds I.B, wherein $R^1$ is hydrogen. The reaction can be performed by analogy to known N-alkylation of pyridazines. N-Alkylation of pyridazines is known in literature and can be found in e.g.: J. Chem. Soc., Perkin Trans. Vol. 1, p. 401 (1988), and J. Org. Chem. Vol. 46, p. 2467 (1981). For example, the following compound I.B. may be used as starting material.

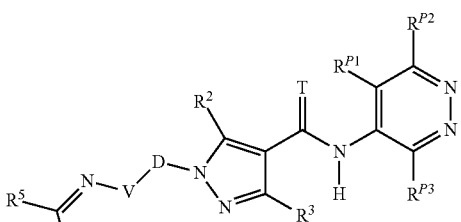

I.B (R¹ = H)

In one further embodiment, the present invention relates to compounds of formula I, wherein V is O, S or $NR^{1a}$. These compounds correspond to formula I.X, formula I.Y and formula I.Z, respectively. Depending on the meaning of V, these compounds may be referred to as oxime, thiooxime and hydrazone compounds, respectively.

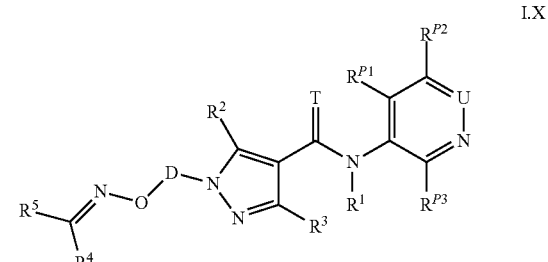

I.X

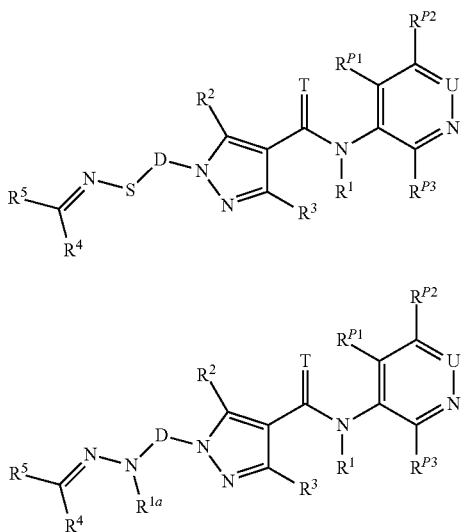

Compounds of formula I.X and formula I.Y are preferred according to the invention. Compounds of formula I.X are particularly preferred.

The compounds of formula I may form further tautomers because of the oxime, thiooxime and hydrazone moieties, which are established depending on the selection of V. For example, imine-enamine tautomerism may be present in the compounds of formula I.X, I.Y, and I.Z, if any one of $R^4$ or $R^5$ provides for a hydrogen atom at the α-carbon atom, and/or azo-hydrazone tautomerism may be present in the compounds of formula I.Z. if $R^{1a}$ is selected to be H. Tautomers, which are formed because of the oxime, thiooxime and hydrazone moieties, are also covered by the compounds of formula I according to the invention.

N-oxides of the compounds of formula I, can be prepared by oxidation of compounds I according to standard methods of preparing heteroaromatic N-oxides, e.g. by the method described in Journal of Organometallic Chemistry 1989, 370, 17-31.

If individual compounds cannot be prepared via the above-described routes, they can be prepared by derivatization of other compounds I or by customary modifications of the synthesis routes described. For example, in individual cases, certain compounds I can advantageously be prepared from other compounds I by ester hydrolysis, amidation, esterification, ether cleavage, olefination, reduction, oxidation and the like.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration.

The term "compound(s) according to the invention", or "compounds of formula I" comprises the compound(s) as defined herein as well as a stereoisomer, salt, tautomer or N-oxide thereof.

The term "compound(s) of the present invention" is to be understood as equivalent to the term "compound(s) according to the invention", therefore also comprising a stereoisomer, salt, tautomer or N-oxide thereof.

The radicals attached to the backbone of formula I may contain one or more centers of chirality. In this case the compounds of formula I are present in the form of different enantiomers or diastereomers, depending on the substituents. The present invention relates to every possible stereoisomer of the formula I, i.e. to single enantiomers or diastereomers, as well as to mixtures thereof.

As already indicated above, the compounds of formula I may be present in the form of different geometric isomers depending on the configuration of the substituents at the carbon-nitrogen double bond of the oxime, thiooxime or hydrazone group. The present invention relates to both, the E- and Z-isomers of the compounds of formula I. In preferred embodiments of the invention, the compounds of formula I will be present in the form of E-isomers.

As already indicated above, the compounds of formula I may be present in the form of different structural isomers depending on the position of $R^1$, provided that $R^1$ is different from H. The present invention relates to every possible structural isomer as indicated in the compounds of formula I.A($R^1 \neq H$):ISO-A, formula I.A($R^1 \neq H$):ISO-B, formula I.B ($R^1 \neq H$):ISO-A, formula I.B($R^1 \neq H$):ISO-B, formula I.B ($R^1 \neq H$):ISO-C, and mixtures thereof.

As already indicated above, the compounds of formula I may also be present in the form of different tautomers, if $R^1$ is H, if V is $NR^{1a}$ with $R^{1a}$ being H and/or if any one of $R^4$ or $R^5$ provides for a hydrogen atom at the α-carbon atom. The present invention relates to every possible tautomer of the formula I.

The compounds of formula I may be amorphous or may exist in one or more different crystalline states (polymorphs) which may have different macroscopic properties such as stability or show different biological properties such as activities. The present invention relates to amorphous and crystalline compounds of formula I, mixtures of different crystalline states of the respective compound I, as well as amorphous or crystalline salts thereof.

Salts of the compounds of the formula I are preferably veterinary and/or agriculturally acceptable salts, preferably agriculturally acceptable salts. They can be formed in a customary manner, e.g. by reacting the compound with an acid of the anion in question if the compound of formula I has a basic functionality.

Veterinary and/or agriculturally useful salts of the compounds of formula I encompass especially the acid addition salts of those acids whose cations and anions, respectively, have no adverse effect on the pesticidal action of the compounds of formula I.

Anions of useful acid addition salts are primarily chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate. They can be formed by reacting compounds of formula I with an acid of the corresponding anion, preferably of hydrochloric acid, hydrobromic acid, sulfuric acid, phosphoric acid or nitric acid.

The term "N-oxide" includes any compound of formula I which has at least one tertiary nitrogen atom that is oxidized to an N-oxide moiety.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine or bromine.

The term "alkyl" as used herein and in the alkyl moieties of alkylamino, alkylcarbonyl, alkylthio, alkylsulfinyl, alkylsulfonyl and alkoxyalkyl denotes in each case a straight-chain or branched alkyl group having usually from 1 to 10 carbon atoms, frequently from 1 to 6 carbon atoms, preferably 1 to 4 carbon atoms, more preferably from 1 to 3 carbon atoms. Examples of an alkyl group are methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl.

The term "haloalkyl" as used herein and in the haloalkyl moieties of haloalkylcarbonyl, haloalkoxycarbonyl, haloalkylthio, haloalkylsulfonyl, haloalkylsulfinyl, haloalkoxy and haloalkoxyalkyl, denotes in each case a straight-chain or branched alkyl group having usually from 1 to 10 carbon atoms, frequently from 1 to 6 carbon atoms, preferably from 1 to 4 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_3$-haloalkyl or $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "alkoxy" as used herein denotes in each case a straight-chain or branched alkyl group which is bound via an oxygen atom and has usually from 1 to 10 carbon atoms, frequently from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert.-butyloxy, and the like.

The term "alkoxyalkyl" as used herein refers to alkyl usually comprising 1 to 10, frequently 1 to 4, preferably 1 to 2 carbon atoms, wherein 1 carbon atom carries an alkoxy radical usually comprising 1 to 4, preferably 1 or 2 carbon atoms as defined above. Examples are $CH_2OCH_3$, $CH_2$—$OC_2H_5$, 2-(methoxy)ethyl, and 2-(ethoxy)ethyl.

The term "haloalkoxy" as used herein denotes in each case a straight-chain or branched alkoxy group having from 1 to 10 carbon atoms, frequently from 1 to 6 carbon atoms, preferably 1 to 4 carbon atoms, wherein the hydrogen atoms of this group are partially or totally replaced with halogen atoms, in particular fluorine atoms. Preferred haloalkoxy moieties include $C_1$-$C_4$-haloalkoxy, in particular $C_1$-$C_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoro-ethoxy, 2,2dichloro-2-fluorethoxy, 2,2,2-trichloroethoxy, pentafluoroethoxy and the like.

The term "alkylthio" (alkylsulfanyl: alkyl-S—)" as used herein refers to a straight-chain or branched saturated alkyl group having 1 to 10 carbon atoms, preferably 1 to 4 carbon atoms (=$C_1$-$C_4$-alkylthio), more preferably 1 to 3 carbon atoms, which is attached via a sulfur atom.

The term "haloalkylthio" as used herein refers to an alkylthio group as mentioned above wherein the hydrogen atoms are partially or fully substituted by fluorine, chlorine, bromine and/or iodine.

The term "alkylsulfinyl" (alkylsulfoxyl: $C_1$-$C_6$-alkyl-S(=O)—), as used herein refers to a straight-chain or branched saturated alkyl group (as mentioned above) having 1 to 10 carbon atoms, preferably 1 to 4 carbon atoms (=$C_1$-$C_4$-alkylsulfinyl), more preferably 1 to 3 carbon atoms bound through the sulfur atom of the sulfinyl group at any position in the alkyl group.

The term "haloalkylsulfinyl" as used herein refers to an alkylsulfinyl group as mentioned above wherein the hydrogen atoms are partially or fully substituted by fluorine, chlorine, bromine and/or iodine.

The term "alkylsulfonyl" (alkyl-S(=O)$_2$—) as used herein refers to a straight-chain or branched saturated alkyl group having 1 to 10 carbon atoms, preferably 1 to 4 carbon atoms (=$C_1$-$C_4$-alkylsulfonyl), preferably 1 to 3 carbon atoms, which is bound via the sulfur atom of the sulfonyl group at any position in the alkyl group.

The term "haloalkylsulfonyl" as used herein refers to a alkylsulfonyl group as mentioned above wherein the hydrogen atoms are partially or fully substituted by fluorine, chlorine, bromine and/or iodine.

The term "alkylcarbonyl" refers to an alkyl group as defined above, which is bound via the carbon atom of a carbonyl group (C=O) to the remainder of the molecule.

The term "haloalkylcarbonyl" refers to an alkylcarbonyl group as mentioned above, wherein the hydrogen atoms are partially or fully substituted by fluorine, chlorine, bromine and/or iodine.

The term "alkoxycarbonyl" refers to an alkyl group as defined above, which is bound via an oxygen atom to the remainder of the molecule.

The term "haloalkoxycarbonyl" refers to an alkoxycarbonyl group as mentioned above, wherein the hydrogen atoms are partially or fully substituted by fluorine, chlorine, bromine and/or iodine.

The term "alkenyl" as used herein denotes in each case a singly unsaturated hydrocarbon radical having usually 2 to 10, frequently 2 to 6, preferably 2 to 4 carbon atoms, e.g. vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "haloalkenyl" as used herein refers to an alkenyl group as defined above, wherein the hydrogen atoms are partially or totally replaced with halogen atoms.

The term "alkynyl" as used herein denotes in each case a singly unsaturated hydrocarbon radical having usually 2 to 10, frequently 2 to 6, preferably 2 to 4 carbon atoms, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "haloalkynyl" as used herein refers to an alkynyl group as defined above, wherein the hydrogen atoms are partially or totally replaced with halogen atoms.

The term "cycloalkyl" as used herein and in the cycloalkyl moieties of cycloalkoxy and cycloalkylmethyl denotes in each case a monocyclic cycloaliphatic radical having usually from 3 to 10 or from 3 to 6 carbon atoms, such as cyclopropyl, cyclobutyl, cyclopentyl, cyclohexyl, cycloheptyl, cyclooctyl, cyclononyl and cyclodecyl or cyclopropyl, cyclobutyl, cyclopentyl and cyclohexyl.

The term "halocycloalkyl" as used herein and in the halocycloalkyl moieties of halocycloalkoxy denotes in each case a monocyclic cycloaliphatic radical having usually from 3 to 10 C atoms or 3 to 6 C atoms, wherein at least one, e.g. 1, 2, 3, 4 or 5 of the hydrogen atoms, are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-,2- and 3-fluorocyclopentyl, 1,2-, 2,2-, 2,3-, 3,3-, 3,4-, 2,5-difluorocyclopentyl, 1-,2- and 3-chlorocyclopentyl, 1,2-, 2,2-, 2,3-, 3,3-, 3,4-, 2,5-dichlorocyclopentyl and the like.

The term "cycloalkoxy" refers to a cycloalkyl group as defined above, which is bound via an oxygen atom to the remainder of the molecule.

The term "halocycloalkoxy" refers to a halocycloalkyl group as defined above, which is bound via an oxygen atom to the remainder of the molecule.

The term "cycloalkylalkyl" refers to a cycloalkyl group as defined above which is bound via an alkyl group, such as a $C_1$-$C_5$-alkyl group or a $C_1$-$C_4$-alkyl group, in particular a methyl group (=cycloalkylmethyl), to the remainder of the molecule.

The term "cycloalkenyl" as used herein denotes in each case a monocyclic singly unsaturated non-aromatic radical having usually from 5 to 10 or from 3 to 8 carbon atoms, including e.g. cycloheptenyl or cyclooctenyl.

The term "heterocyclyl" includes in general 5-, or 6-membered, in particular 6-membered monocyclic heterocyclic non-aromatic radicals. The heterocyclic non-aromatic radicals usually comprise 1, 2, or 3 heteroatoms selected from N, O and S as ring members, where S-atoms as ring members may be present as S, SO or $SO_2$. Examples of 5-, or 6-membered heterocyclic radicals comprise saturated or unsaturated, non-aromatic heterocyclic rings, such as oxiranyl, oxetanyl, thietanyl, thietanyl-S-oxid (S-oxothietanyl), thietanyl-S-dioxid (S-dioxothiethanyl), pyrrolidinyl, pyrrolinyl, pyrazolinyl, tetrahydrofuranyl, dihydrofuranyl, 1,3-dioxolanyl, thiolanyl, Soxothiolanyl, S-dioxothiolanyl, dihydrothienyl, S-oxodihydrothienyl, S-dioxodihydrothienyl, oxazolidinyl, oxazolinyl, thiazolinyl, oxathiolanyl, piperidinyl, piperazinyl, pyranyl, dihydropyranyl, tetrahydropyranyl, 1,3- and 1,4-dioxanyl, thiopyranyl, S.oxothiopyranyl, S-dioxothiopyranyl, dihydrothiopyranyl, S-oxodihydrothiopyranyl, S-dioxodihydrothiopyranyl, tetrahydrothiopyranyl, Soxotetrahydrothiopyranyl, S-dioxotetrahydrothiopyranyl, morpholinyl, thiomorpholinyl, S-oxothiomorpholinyl, 5-dioxothiomorpholinyl, thiazinyl and the like. Examples for heterocyclic ring also comprising 1 or 2 carbonyl groups as ring members comprise pyrrolidin-2-onyl, pyrrolidin-2,5-dionyl, imidazolidin-2-onyl, oxazolidin-2-onyl, thiazolidin-2-onyl and the like.

The term "hetaryl" includes monocyclic 5- or 6-membered heteroaromatic radicals comprising as ring members 1, 2, 3 or 4 heteroatoms selected from N, O and S. Examples of 5- or 6-membered heteroaromatic radicals include pyridyl, i.e. 2-, 3-, or 4-pyridyl, pyrimidinyl, i.e. 2-, 4- or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3- or 5-oxazolyl, isoxazolyl, i.e. 3-, 4- or 5-isoxazolyl, thiazolyl, i.e. 2-, 3- or 5-thiazolyl, isothiazolyl, i.e. 3-, 4- or 5-isothiazolyl, pyrazolyl, i.e. 1-, 3-, 4- or 5-pyrazolyl, i.e. 1-, 2-, 4- or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl. The term "hetaryl" also includes bicyclic 8 to 10-membered heteroaromatic radicals comprising as ring members 1, 2 or 3 heteroatoms selected from N, O and S, wherein a 5- or 6-membered heteroaromatic ring is fused to a phenyl ring or to a 5- or 6-membered heteroaromatic radical. Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

The terms "heterocyclyloxy" and "phenoxy" refer to heterocyclyl as defined above and phenyl, which are bound via an oxygen atom to the remainder of the molecule.

The terms "heterocyclylsulfonyl", "phenylsulfonyl" and "hetarylsulfonyl" refer to heterocyclyl as defined above, phenyl, and hetaryl as defined above, respectively, which are bound via the sulfur atom of a sulfonyl group to the remainder of the molecule.

The terms "heterocyclylcarbonyl", "phenylcarbonyl" and "hetarylcarbonyl" refer to heterocyclyl as defined above, phenyl, and hetaryl as defined above, respectively, which are bound via the carbon atom of a carbonyl group (C=O) to the remainder of the molecule.

The terms "heterocyclyolalkyl" and "hetarylalkyl" refer to heterocyclyl or hetaryl, respectively, as defined above which are bound via a $C_1$-$C_5$-alkyl group or a $C_1$-$C_4$-alkyl group, in particular a methyl group (=heterocyclylmethyl or hetarylmethyl, respectively), to the remainder of the molecule.

The term "phenylalkyl" refers to phenyl, which is bound via $C_1$-$C_5$-alkyl group or a $C_1$-$C_4$-alkyl group, in particular a methyl group (=phenylmethyl), to the remainder of the molecule, examples including benzyl, 1-phenylethyl, 2-phenylethyl, 2-phenoxyethyl etc.

The term "heterocycloalkyl" includes in general 3- to 8-membered, in particular 6-membered monocyclic saturated heterocyclic non-aromatic radicals. The heterocyclic non-aromatic radicals usually comprise 1, 2, or 3 heteroatoms selected from N, O and S as ring members, where S-atoms as ring members may be present as S, SO or $SO_2$.

The term "heterocycloalkenyl" includes in general 3- to 8-membered, in particular 6-membered monocyclic singly unsaturated heterocyclic non-aromatic radicals. The heterocyclic non-aromatic radicals usually comprise 1, 2, or 3 heteroatoms selected from N, O and S as ring members, where S-atoms as ring members may be present as S, SO or $SO_2$.

The terms "alkylene", "cycloalkylene", "heterocycloalkylene", "alkenylene", "cycloalkenylene", "heterocycloalkenylene" and "alkynylene" refer to alkyl, cycloalkyl, heterocycloalkyl, alkenyl, cycloalkenyl, heterocycloalkenyl and alkyinyl as defined above, respectively, which are bound to the remainder of the molecule, via two atoms, preferably via two carbon atoms, of the respective group.

The term "carbocycle" includes in general a 3- to 8-membered or a 5- to 8-membered, preferably a 5- or 6-membered mono-cyclic, non-aromatic ring comprising 3 to 8 or 5 to 8, preferably 5 or 6 carbon atoms.

The term "heterocycle" includes in general a 3- to 8-membered or a 5- to 8-membered, preferably a 5- or 6-membered monocyclic non-aromatic ring as described for the "carbocycle" above, which comprises 1, 2, or 3 heteroatoms selected from N, O and S as ring members, where S-atoms as ring members may be present as S, SO or $SO_2$.

With respect to the variables, the particularly preferred embodiments of the intermediates correspond to those of the compounds of the formula I.

In a particular embodiment, the variables of the compounds of the formula I have the following meanings, these meanings, both on their own and in combination with one another, being particular embodiments of the compounds of the formula I:

In a preferred embodiment, the invention relates to compounds of formula I, wherein T is O, i.e. compounds of formula I.1 as depicted above.

In another preferred embodiment, the invention relates to compounds of formula I, wherein U is CH or N, i.e. compounds of formula I.A and I.B as depicted above. Compounds of formula I, wherein U is N, i.e. compounds of formula I.B, are particularly preferred according to the invention.

In another preferred embodiment, the invention relates to compounds of formula I, wherein V is O or S, i.e. compounds of formula I.X and I.Y as depicted above.

In a preferred embodiment of the compounds of formula I, $R^{P1}$, $R^{P2}$ and $R^{P3}$ are H. These compounds correspond to formula I*.

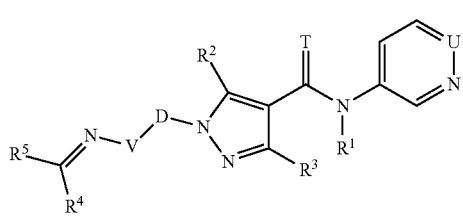

The compounds of formula I* may also be represented by the following formula I*, wherein $R^N$ represents the $(R^5)(R^4)C=N-V-D$-substituent at the nitrogen atom of the pyrazole ring.

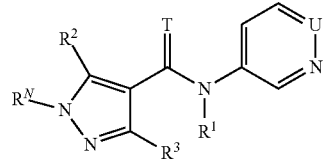

In another preferred embodiment of the compounds of formula I, $R^1$ is H, $C_1$-$C_2$-alkyl, or $C_1$-$C_2$-alkoxy-$C_1$-$C_2$-alkyl, and preferably $C_1$-$C_2$-alkyl.

In another preferred embodiment of the compounds of formula I, $R^2$ and $R^3$ are independently of each other selected from H, halogen, CN, $C_1$-$C_4$-alkyl, $C_1$-$C_4$-haloalkyl, $C_3$-$C_4$-cycloalkyl, $C_3$-$C_4$-halocycloalkyl, $OR^a$, and $SR^a$, wherein $R^a$ is $C_1$-$C_4$-alkyl, $C_1$-$C_4$-haloalkyl, $C_3$-$C_4$-cycloalkyl, or $C_3$-$C_4$-halocycloalkyl. Preferably $R^2$ is $C_1$-$C_2$-alkyl, $C_1$-$C_2$-haloalkyl, $C_3$-cycloalkyl, or $C_3$-halocycloalkyl, more preferably $R^2$ is $CH_3$ or halomethyl. Preferably $R^3$ is H.

In a first preferred embodiment of the compounds of formula I, $R^4$ is H, $C_1$-$C_4$-alkyl, $C_1$-$C_4$-haloalkyl, $C_3$-$C_6$-cycloalkyl or $C_3$-$C_6$-cycloalkylmethyl, and $R^5$ is $C_1$-$C_4$-alkyl, $C_1$-$C_4$-haloalkyl, $C_3$-$C_6$-cycloalkyl, or $C_3$-$C_6$-cycloalkylmethyl, wherein in each case the $C_1$-$C_4$-alkyl, $C_1$-$C_4$-haloalkyl, $C_3$-$C_6$-cycloalkyl or $C_3$-$C_6$-cycloalkylmethyl may be unsubstituted or may be partially or fully substituted by substituents which, independently of each other, are selected from $R^A$.

In a second preferred embodiment of the compounds of formula I, $R^4$ and $R^5$ are both independently selected from $C_1$-$C_4$-alkyl-X, wherein X is selected from O, S or $NR^B$.

In a third preferred embodiment of the compounds of formula I, $R^4$ and $R^5$ together with the carbon atom to which they are bound form a non-aromatic 5- to 6-membered carbo- or heterocycle, which may contain 1 or 2 heteroatoms which, independently from each other, are selected from $NR^B$, O, and S, wherein S may be oxidized, and/or wherein the carbo- or heterocycle may be unsubstituted or may be partially or fully substituted by substituents which, independently of each other, are selected from $R^A$.

In another preferred embodiment of the compounds of formula I, D is $C_1$-$C_8$-alkylene, $C_3$-$C_8$-cycloalkylene or $C_3$-$C_8$-heterocycloalkylene, preferably $C_2$-$C_8$-alkylene, wherein D may be unsubstituted or may be partially or fully substituted by substituents which, independently of each other, are selected from $R^A$. Preferably D is a branched $C_2$-$C_8$-alkylene, more preferably an alpha-branched $C_2$-$C_8$-alkylene, wherein the $C_2$-$C_8$-alkylene may be unsubstituted or may be partially or fully substituted by substituents which, independently of each other, are selected from $R^A$. It is particularly preferred that D is $CH(CH_3)CH_2$, wherein preferably the $CH_2$ group is bound to V and the $CH(CH_3)$ group is bound to the nitrogen atom of the pyrazole moiety, so that a connectivity of V—$CH_2CH(CH_3)$—N is obtained.

In a first preferred embodiment, $R^A$ is halogen, CN, $C_1$-$C_2$-alkyl, $C_1$-$C_2$-haloalkyl, $C_1$-$C_2$-alkoxy, $C_1$-$C_2$-haloalkoxy, $C_3$-$C_4$-cycloalkyl, $C_3$-$C_4$-halocycloalkyl, $C_3$-$C_4$-cycloalkoxy, or $C_3$-$C_4$-halocycloalkoxy.

In a second preferred embodiment, two $R^A$ are bound to the same carbon atom and together with the carbon atom to which they are bound form a cyclopropane.

In a preferred embodiment, $R^B$ is H, $C_1$-$C_2$-alkyl, $C_1$-$C_2$-haloalkyl or $C_3$-$C_6$-cycloalkyl.

In view of the above, the invention preferably relates to compounds of formula I,
wherein T is O, U is CH, V is O and $R^{P1}$, $R^{P2}$ and $R^{P3}$ are H, i.e. compounds of formula I* 1.A.X;
wherein T is O, U is N, V is O and $R^{P1}$, $R^{P2}$ and $R^{P3}$ are H, i.e. compounds of formula I*.1.B.X;
wherein T is O, U is CH, V is S and $R^{P1}$, $R^{P2}$ and $R^{P3}$ are H, i.e. compounds of formula I*.1.A.Y; or
wherein T is O, U is N, V is S and $R^{P1}$, $R^{P2}$ and $R^{P3}$ are H, i.e. compounds of formula I*.1.A.Y.

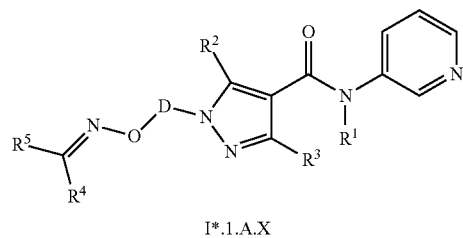

I*.1.A.X

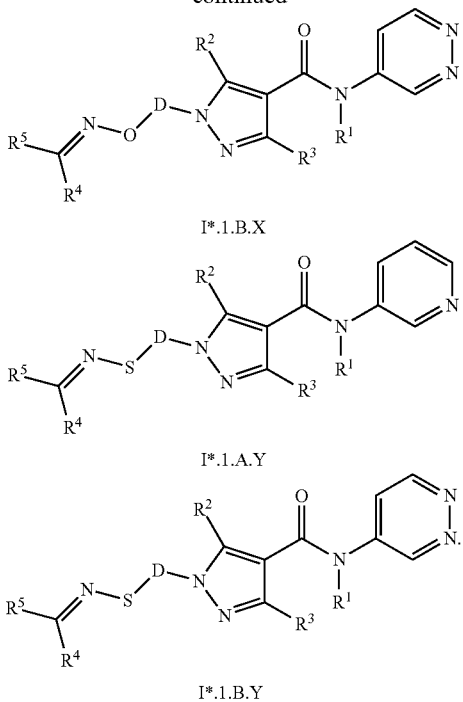

I*.1.B.X

I*.1.A.Y

I*.1.B.Y

In particular with a view to their use, preference is given to the compounds of the formula I compiled in the tables below, which compounds correspond to the formula I.1, in particular compounds of formulae I*.1.A.X, I*.1.B.X, I*.1.A.Y, and I*.1.B.Y, respectively (tables 1 to 9 cover compounds of formula I*.1.A.X, tables 10 to 18 cover compounds of formula I*.1.B.X, tables 19 to 27 cover compounds of formula I*.1.A.Y, and tables 28 to 36 cover compounds of formula I*.1.B.Y). Each of the groups mentioned for a substituent in the tables is furthermore per se, independently of the combination in which it is mentioned, a particularly preferred aspect of the substituent in question.

Table 1
Compounds of the formula I.1, in which U is CH, V is O, $R^{P1}$, $R^{P2}$ and $R^{P3}$ are H, $R^1$ is H, $R^3$ is H, D is $CH_2$ and the combination of $R^2$, $R^4$ and $R^5$ for a compound corresponds in each case to one row of Table A Table 2
Compounds of the formula I.1, in which U is CH, V is O, $R^{P1}$, $R^{P2}$ and $R^{P3}$ are H, $R^1$ is $CH_3$, $R^3$ is H, D is $CH_2$ and the combination of $R^2$, $R^4$ and $R^5$ for a compound corresponds in each case to one row of Table A Table 3
Compounds of the formula I.1, in which U is CH, V is O, $R^{P1}$, $R^{P2}$ and $R^{P3}$ are H, $R^1$ is $CH_2CH_3$, $R^3$ is H, D is $CH_2$ and the combination of $R^2$, $R^4$ and $R^5$ for a compound corresponds in each case to one row of Table A Table 4
Compounds of the formula I.1, in which U is CH, V is O, $R^{P1}$, $R^{P2}$ and $R^{P3}$ are H, $R^1$ is H, $R^3$ is H, D is $CH_2CH_2$ and the combination of $R^2$, $R^4$ and $R^5$ for a compound corresponds in each case to one row of Table A Table 5
Compounds of the formula I.1, in which U is CH, V is O, $R^{P1}$, $R^{P2}$ and $R^{P3}$ are H, $R^1$ is $CH_3$, $R^3$ is H, D is $CH_2CH_2$ and the combination of $R^2$, $R^4$ and $R^5$ for a compound corresponds in each case to one row of Table A Table 6
Compounds of the formula I.1, in which U is CH, V is O, $R^{P1}$, $R^{P2}$ and $R^{P3}$ are H, $R^1$ is $CH_2CH_3$, $R^3$ is H, D is $CH_2CH_2$ and the combination of $R^2$, $R^4$ and $R^5$ for a compound corresponds in each case to one row of Table A Table 7
Compounds of the formula I.1, in which U is CH, V is O, $R^{P1}$, $R^{P2}$ and $R^{P3}$ are H, $R^1$ is H, $R^3$ is H, D is $CH_2CH(CH_3)$, wherein the $CH_2$ group is bound to V and the $CH(CH_3)$ group is bound to the nitrogen atom of the pyrazole moiety, so that a connectivity of V—$CH_2CH(CH_3)$—N is obtained, and in which the combination of $R^2$, $R^4$ and $R^5$ for a compound corresponds in each case to one row of Table A Table 8
Compounds of the formula I.1, in which U is CH, V is O, $R^{P1}$, $R^{P2}$ and $R^{P3}$ are H, $R^1$ is $CH_3$, $R^3$ is H, D is $CH_2CH(CH_3)$, wherein the $CH_2$ group is bound to V and the $CH(CH_3)$ group is bound to the nitrogen atom of the pyrazole moiety, so that a connectivity of V—$CH_2CH(CH_3)$—N is obtained, and in which the combination of $R^2$, $R^4$ and $R^5$ for a compound corresponds in each case to one row of Table A Table 9
Compounds of the formula I.1, in which U is CH, V is O, $R^{P1}$, $R^{P2}$ and $R^{P3}$ are H, $R^1$ is $CH_2CH_3$, $R^3$ is H, D is $CH_2CH(CH_3)$, wherein the $CH_2$ group is bound to V and the $CH(CH_3)$ group is bound to the nitrogen atom of the pyrazole moiety, so that a connectivity of V—$CH_2CH(CH_3)$—N is obtained, and in which the combination of $R^2$, $R^4$ and $R^5$ for a compound corresponds in each case to one row of Table A Table 10
Compounds of the formula I.1, in which U is N, V is O, $R^{P1}$, $R^{P2}$ and $R^{P3}$ are H, $R^1$ is H, $R^3$ is H, D is $CH_2$ and the combination of $R^2$, $R^4$ and $R^5$ for a compound corresponds in each case to one row of Table A Table 11
Compounds of the formula I.1, in which U is N, V is O, $R^{P1}$, $R^{P2}$ and $R^{P3}$ are H, $R^1$ is $CH_3$, $R^3$ is H, D is $CH_2$ and the combination of $R^2$, $R^4$ and $R^5$ for a compound corresponds in each case to one row of Table A Table 12
Compounds of the formula I.1, in which U is N, V is O, $R^{P1}$, $R^{P2}$ and $R^{P3}$ are H, $R^1$ is $CH_2CH_3$, $R^3$ is H, D is $CH_2$ and the combination of $R^2$, $R^4$ and $R^5$ for a compound corresponds in each case to one row of Table A Table 13
Compounds of the formula I.1, in which U is N, V is O, $R^{P1}$, $R^{P2}$ and $R^{P3}$ are H, $R^1$ is H, $R^3$ is H, D is $CH_2CH_2$ and the combination of $R^2$, $R^4$ and $R^5$ for a compound corresponds in each case to one row of Table A Table 14
Compounds of the formula I.1, in which U is N, V is O, $R^{P1}$, $R^{P2}$ and $R^{P3}$ are H, $R^1$ is $CH_3$, $R^3$ is H, D is $CH_2CH_2$ and the combination of $R^2$, $R^4$ and $R^5$ for a compound corresponds in each case to one row of Table A Table 15
Compounds of the formula I.1, in which U is N, V is O, $R^{P1}$, $R^{P2}$ and $R^{P3}$ are H, $R^1$ is $CH_2CH_3$, $R^3$ is H, D is $CH_2CH_2$ and the combination of $R^2$, $R^4$ and $R^5$ for a compound corresponds in each case to one row of Table A Table 16
Compounds of the formula I.1, in which U is N, V is O, $R^{P1}$, $R^{P2}$ and $R^{P3}$ are H, $R^1$ is H, $R^3$ is H, D is $CH_2CH(CH_3)$, wherein the $CH_2$ group is bound to V and the $CH(CH_3)$ group is bound to the nitrogen atom of the pyrazole moiety, so that a connectivity of V—$CH_2CH(CH_3)$—N is obtained, and in which the combination of $R^2$, $R^4$ and $R^5$ for a compound corresponds in each case to one row of Table A Table 17
Compounds of the formula I.1, in which U is N, V is O, $R^{P1}$, $R^{P2}$ and $R^{P3}$ are H, $R^1$ is $CH_3$, $R^3$ is H, D is $CH_2CH(CH_3)$, wherein the $CH_2$ group is bound to V and the $CH(CH_3)$ group is bound to the nitrogen atom of the pyrazole moiety, so that a connectivity of V—$CH_2CH(CH_3)$—N is obtained, and in which the combination of $R^2$, $R^4$ and $R^5$ for a compound corresponds in each case to one row of Table A Table 18
Compounds of the formula I.1, in which U is N, V is O, $R^{P1}$, $R^{P2}$ and $R^{P3}$ are H, $R^1$ is $CH_2CH_3$, $R^3$ is H, D is $CH_2CH(CH_3)$, wherein the $CH_2$ group is bound to V and the $CH(CH_3)$ group is bound to the nitrogen atom of the pyrazole moiety, so that a connectivity of V—$CH_2CH(CH_3)$—N is obtained, and in which the combination of $R^2$, $R^4$ and $R^5$ for a compound corresponds in each case to one row of Table A Table 19
Compounds of the formula I.1, in which U is CH, V is S, $R^{P1}$, $R^{P2}$ and $R^{P3}$ are H, $R^1$ is H, $R^3$ is H, D is $CH_2$ and the combination of $R^2$, $R^4$ and $R^5$ for a compound corresponds in each case to one row of Table A Table 20
Compounds of the formula I.1, in which U is CH, V is S, $R^{P1}$, $R^{P2}$ and $R^{P3}$ are H, $R^1$ is $CH_3$, $R^3$ is H, D is $CH_2$ and the combination of $R^2$, $R^4$ and $R^5$ for a compound corresponds in each case to one row of Table A Table 21
Compounds of the formula I.1, in which U is CH, V is S, $R^{P1}$, $R^{P2}$ and $R^{P3}$ are H, $R^1$ is $CH_2CH_3$, $R^3$ is H, D is $CH_2$ and the combination of $R^2$, $R^4$ and $R^5$ for a compound corresponds in each case to one row of Table A Table 22
Compounds of the formula I.1, in which U is CH, V is S, $R^{P1}$, $R^{P2}$ and $R^{P3}$ are H, $R^1$ is H, $R^3$ is H, D is $CH_2CH_2$ and the combination of $R^2$, $R^4$ and $R^5$ for a compound corresponds in each case to one row of Table A Table 23
Compounds of the formula I.1, in which U is CH, V is S, $R^{P1}$, $R^{P2}$ and $R^{P3}$ are H, $R^1$ is $CH_3$, $R^3$ is H, D is $CH_2CH_2$ and the combination of $R^2$, $R^4$ and $R^5$ for a compound corresponds in each case to one row of Table A Table 24
Compounds of the formula I.1, in which U is CH, V is S, $R^{P1}$, $R^{P2}$ and $R^{P3}$ are H, $R^1$ is $CH_2CH_3$, $R^3$ is H, D is $CH_2CH_2$ and the combination of $R^2$, $R^4$ and $R^5$ for a compound corresponds in each case to one row of Table A Table 25
Compounds of the formula I.1, in which U is CH, V is S, $R^{P1}$, $R^{P2}$ and $R^{P3}$ are H, $R^1$ is H, $R^3$ is H, D is $CH_2CH(CH_3)$, wherein the $CH_2$ group is bound to V and the $CH(CH_3)$ group is bound to the nitrogen atom of the pyrazole moiety, so that a connectivity of V—$CH_2CH(CH_3)$—N is obtained, and in which the combination of $R^2$, $R^4$ and $R^5$ for a compound corresponds in each case to one row of Table A Table 26
Compounds of the formula I.1, in which U is CH, V is S, $R^{P1}$, $R^{P2}$ and $R^{P3}$ are H, $R^1$ is $CH_3$, $R^3$ is H, D is $CH_2CH(CH_3)$, wherein the $CH_2$ group is bound to V and the $CH(CH_3)$ group is bound to the nitrogen atom of the pyrazole moiety, so that a connectivity of V—$CH_2CH(CH_3)$—N is obtained, and in which the combination of $R^2$, $R^4$ and $R^5$ for a compound corresponds in each case to one row of Table A Table 27
Compounds of the formula I.1, in which U is CH, V is S, $R^{P1}$, $R^{P2}$ and $R^{P3}$ are H, $R^1$ is $CH_2CH_3$, $R^3$ is H, D is $CH_2CH(CH_3)$, wherein the $CH_2$ group is bound to V and the $CH(CH_3)$ group is bound to the nitrogen atom of the pyrazole moiety, so that a connectivity of V—$CH_2CH(CH_3)$—N is obtained, and in which the combination of $R^2$, $R^4$ and $R^5$ for a compound corresponds in each case to one row of Table A Table 28
Compounds of the formula I.1, in which U is N, V is S, $R^{P1}$, $R^{P2}$ and $R^{P3}$ are H, $R^1$ is H, $R^3$ is H, D is $CH_2$ and the combination of $R^2$, $R^4$ and $R^5$ for a compound corresponds in each case to one row of Table A Table 29
Compounds of the formula I.1, in which U is N, V is S, $R^{P1}$, $R^{P2}$ and $R^{P3}$ are H, $R^1$ is $CH_3$, $R^3$ is H, D is $CH_2$ and the combination of $R^2$, $R^4$ and $R^5$ for a compound corresponds in each case to one row of Table A Table 30
Compounds of the formula I.1, in which U is N, V is S, $R^{P1}$, $R^{P2}$ and $R^{P3}$ are H, $R^1$ is $CH_2CH_3$, $R^3$ is H, D is $CH_2$ and the combination of $R^2$, $R^4$ and $R^5$ for a compound corresponds in each case to one row of Table A Table 31
Compounds of the formula I.1, in which U is N, V is S, $R^{P1}$, $R^{P2}$ and $R^{P3}$ are H, $R^1$ is H, $R^3$ is H, D is $CH_2CH_2$ and the combination of $R^2$, $R^4$ and $R^5$ for a compound corresponds in each case to one row of Table A Table 32
Compounds of the formula I.1, in which U is N, V is S, $R^{P1}$, $R^{P2}$ and $R^{P3}$ are H, $R^1$ is $CH_3$, $R^3$ is H, D is $CH_2CH_2$ and the combination of $R^2$, $R^4$ and $R^5$ for a compound corresponds in each case to one row of Table A Table 33
Compounds of the formula I.1, in which U is N, V is S, $R^{P1}$, $R^{P2}$ and $R^{P3}$ are H, $R^1$ is $CH_2CH_3$, $R^3$ is H, D is $CH_2CH_2$ and the combination of $R^2$, $R^4$ and $R^5$ for a compound corresponds in each case to one row of Table A Table 34
Compounds of the formula I.1, in which U is N, V is S, $R^{P1}$, $R^{P2}$ and $R^{P3}$ are H, $R^1$ is H, $R^3$ is H, D is $CH_2CH(CH_3)$, wherein the $CH_2$ group is bound to V and the $CH(CH_3)$ group is bound to the nitrogen atom of the pyrazole moiety, so that a connectivity of V—$CH_2CH(CH_3)$—N is obtained, and in which the combination of $R^2$, $R^4$ and $R^5$ for a compound corresponds in each case to one row of Table A Table 35
Compounds of the formula I.1, in which U is N, V is S, $R^{P1}$, $R^{P2}$ and $R^{P3}$ are H, $R^1$ is $CH_3$, $R^3$ is H, D is $CH_2CH(CH_3)$, wherein the $CH_2$ group is bound to V and the $CH(CH_3)$ group is bound to the nitrogen atom of the pyrazole moiety, so that a connectivity of V—$CH_2CH(CH_3)$—N is obtained, and in which the combination of $R^2$, $R^4$ and $R^5$ for a compound corresponds in each case to one row of Table A Table 36
Compounds of the formula I.1, in which U is N, V is S, $R^{P1}$, $R^{P2}$ and $R^{P3}$ are H, $R^1$ is $CH_2CH_3$, $R^3$ is H, D is $CH_2CH(CH_3)$, wherein the $CH_2$ group is bound to V and the $CH(CH_3)$ group is bound to the nitrogen atom of the pyrazole moiety, so that a connectivity of V—$CH_2CH(CH_3)$—N is obtained, and in which the combination of $R^2$, $R^4$ and $R^5$ for a compound corresponds in each case to one row of Table A

TABLE A

| No. | R² | R⁵ | R⁴ |
|---|---|---|---|
| A-1 | CH₃ | CH₃ | H |
| A-2 | CH₃ | CH₂CH₃ | H |
| A-3 | CH₃ | CH₂CH₂CH₃ | H |
| A-4 | CH₃ | CH(CH₃)₂ | H |
| A-5 | CH₃ | CH₂CH₂CH₂CH₃ | H |
| A-6 | CH₃ | CH(CH₃)(CH₂CH₃) | H |
| A-7 | CH₃ | CH₂CH(CH₃)₂ | H |
| A-8 | CH₃ | C(CH₃)₃ | H |
| A-9 | CH₃ | CH₂F | H |
| A-10 | CH₃ | CHF₂ | H |
| A-11 | CH₃ | CF₃ | H |
| A-12 | CH₃ | CH₂CH₂F | H |
| A-13 | CH₃ | CH₂CHF₂ | H |
| A-14 | CH₃ | CH₂CF₃ | H |
| A-15 | CH₃ | c-C₃H₅ | H |
| A-16 | CH₃ | c-C₄H₇ | H |
| A-17 | CH₃ | c-C₅H₉ | H |
| A-18 | CH₃ | c-C₆H₁₁ | H |
| A-19 | CH₃ | CH₂—c-C₃H₅ | H |
| A-20 | CH₃ | CH₂—c-C₄H₇ | H |
| A-21 | CH₃ | CH₂—c-C₅H₉ | H |
| A-22 | CH₃ | CH₂—c-C₆H₁₁ | H |
| A-23 | CH₃ | CH₂CN | H |
| A-24 | CH₃ | CH₂CH₂CN | H |
| A-25 | CH₃ | CH₂OCH₃ | H |
| A-26 | CH₃ | CH(CH₃)OCH₃ | H |
| A-27 | CH₃ | CH₂CH₂OCH₃ | H |
| A-28 | CHF₂ | CH₃ | H |
| A-29 | CHF₂ | CH₂CH₃ | H |
| A-30 | CHF₂ | CH₂CH₂CH₃ | H |
| A-31 | CHF₂ | CH(CH₃)₂ | H |
| A-32 | CHF₂ | CH₂CH₂CH₂CH₃ | H |
| A-33 | CHF₂ | CH(CH₃)(CH₂CH₃) | H |
| A-34 | CHF₂ | CH₂CH(CH₃)₂ | H |
| A-35 | CHF₂ | C(CH₃)₃ | H |
| A-36 | CHF₂ | CH₂F | H |
| A-37 | CHF₂ | CHF₂ | H |
| A-38 | CHF₂ | CF₃ | H |
| A-39 | CHF₂ | CH₂CH₂F | H |
| A-40 | CHF₂ | CH₂CHF₂ | H |
| A-41 | CHF₂ | CH₂CF₃ | H |
| A-42 | CHF₂ | c-C₃H₅ | H |
| A-43 | CHF₂ | c-C₄H₇ | H |
| A-44 | CHF₂ | c-C₅H₉ | H |
| A-45 | CHF₂ | c-C₆H₁₁ | H |
| A-46 | CHF₂ | CH₂—c-C₃H₅ | H |
| A-47 | CHF₂ | CH₂—c-C₄H₇ | H |
| A-48 | CHF₂ | CH₂—c-C₅H₉ | H |
| A-49 | CHF₂ | CH₂—c-C₆H₁₁ | H |
| A-50 | CHF₂ | CH₂CN | H |
| A-51 | CHF₂ | CH₂CH₂CN | H |
| A-52 | CHF₂ | CH₂OCH₃ | H |
| A-53 | CHF₂ | CH(CH₃)OCH₃ | H |
| A-54 | CHF₂ | CH₂CH₂OCH₃ | H |
| A-55 | CF₃ | CH₃ | H |
| A-56 | CF₃ | CH₂CH₃ | H |
| A-57 | CF₃ | CH₂CH₂CH₃ | H |
| A-58 | CF₃ | CH(CH₃)₂ | H |
| A-59 | CF₃ | CH₂CH₂CH₂CH₃ | H |
| A-60 | CF₃ | CH(CH₃)(CH₂CH₃) | H |
| A-61 | CF₃ | CH₂CH(CH₃)₂ | H |
| A-62 | CF₃ | C(CH₃)₃ | H |
| A-63 | CF₃ | CH₂F | H |
| A-64 | CF₃ | CHF₂ | H |
| A-65 | CF₃ | CF₃ | H |
| A-66 | CF₃ | CH₂CH₂F | H |
| A-67 | CF₃ | CH₂CHF₂ | H |
| A-68 | CF₃ | CH₂CF₃ | H |
| A-69 | CF₃ | c-C₃H₅ | H |
| A-70 | CF₃ | c-C₄H₇ | H |
| A-71 | CF₃ | c-C₅H₉ | H |
| A-72 | CF₃ | c-C₆H₁₁ | H |
| A-73 | CF₃ | CH₂—c-C₃H₅ | H |
| A-74 | CF₃ | CH₂—c-C₄H₇ | H |
| A-75 | CF₃ | CH₂—c-C₅H₉ | H |
| A-76 | CF₃ | CH₂—c-C₆H₁₁ | H |
| A-77 | CF₃ | CH₂CN | H |
| A-78 | CF₃ | CH₂CH₂CN | H |
| A-79 | CF₃ | CH₂OCH₃ | H |
| A-80 | CF₃ | CH(CH₃)OCH₃ | H |
| A-81 | CF₃ | CH₂CH₂OCH₃ | H |
| A-82 | CH₃ | CH₃ | CH₃ |
| A-83 | CH₃ | CH₂CH₃ | CH₃ |
| A-84 | CH₃ | CH₂CH₂CH₃ | CH₃ |
| A-85 | CH₃ | CH(CH₃)₂ | CH₃ |
| A-86 | CH₃ | CH₂CH₂CH₂CH₃ | CH₃ |
| A-87 | CH₃ | CH(CH₃)(CH₂CH₃) | CH₃ |
| A-88 | CH₃ | CH₂CH(CH₃)₂ | CH₃ |
| A-89 | CH₃ | C(CH₃)₃ | CH₃ |
| A-90 | CH₃ | CH₂F | CH₃ |
| A-91 | CH₃ | CHF₂ | CH₃ |
| A-92 | CH₃ | CF₃ | CH₃ |
| A-93 | CH₃ | CH₂CH₂F | CH₃ |
| A-94 | CH₃ | CH₂CHF₂ | CH₃ |
| A-95 | CH₃ | CH₂CF₃ | CH₃ |
| A-96 | CH₃ | c-C₃H₅ | CH₃ |
| A-97 | CH₃ | c-C₄H₇ | CH₃ |
| A-98 | CH₃ | c-C₅H₉ | CH₃ |
| A-99 | CH₃ | c-C₆H₁₁ | CH₃ |
| A-100 | CH₃ | CH₂—c-C₃H₅ | CH₃ |
| A-101 | CH₃ | CH₂—c-C₄H₇ | CH₃ |
| A-102 | CH₃ | CH₂—c-C₅H₉ | CH₃ |
| A-103 | CH₃ | CH₂—c-C₆H₁₁ | CH₃ |
| A-104 | CH₃ | CH₂CN | CH₃ |
| A-105 | CH₃ | CH₂CH₂CN | CH₃ |
| A-106 | CH₃ | CH₂OCH₃ | CH₃ |
| A-107 | CH₃ | CH(CH₃)OCH₃ | CH₃ |
| A-108 | CH₃ | CH₂CH₂OCH₃ | CH₃ |
| A-109 | CHF₂ | CH₃ | CH₃ |
| A-110 | CHF₂ | CH₂CH₃ | CH₃ |
| A-111 | CHF₂ | CH₂CH₂CH₃ | CH₃ |
| A-112 | CHF₂ | CH(CH₃)₂ | CH₃ |
| A-113 | CHF₂ | CH₂CH₂CH₂CH₃ | CH₃ |
| A-114 | CHF₂ | CH(CH₃)(CH₂CH₃) | CH₃ |
| A-115 | CHF₂ | CH₂CH(CH₃)₂ | CH₃ |
| A-116 | CHF₂ | C(CH₃)₃ | CH₃ |
| A-117 | CHF₂ | CH₂F | CH₃ |
| A-118 | CHF₂ | CHF₂ | CH₃ |
| A-119 | CHF₂ | CF₃ | CH₃ |
| A-120 | CHF₂ | CH₂CH₂F | CH₃ |
| A-121 | CHF₂ | CH₂CHF₂ | CH₃ |
| A-122 | CHF₂ | CH₂CF₃ | CH₃ |
| A-123 | CHF₂ | c-C₃H₅ | CH₃ |
| A-124 | CHF₂ | c-C₄H₇ | CH₃ |
| A-125 | CHF₂ | c-C₅H₉ | CH₃ |
| A-126 | CHF₂ | c-C₆H₁₁ | CH₃ |
| A-127 | CHF₂ | CH₂—c-C₃H₅ | CH₃ |
| A-128 | CHF₂ | CH₂—c-C₄H₇ | CH₃ |
| A-129 | CHF₂ | CH₂—c-C₅H₉ | CH₃ |
| A-130 | CHF₂ | CH₂—c-C₆H₁₁ | CH₃ |
| A-131 | CHF₂ | CH₂CN | CH₃ |
| A-132 | CHF₂ | CH₂CH₂CN | CH₃ |
| A-133 | CHF₂ | CH₂OCH₃ | CH₃ |
| A-134 | CHF₂ | CH(CH₃)OCH₃ | CH₃ |
| A-135 | CHF₂ | CH₂CH₂OCH₃ | CH₃ |
| A-136 | CF₃ | CH₃ | CH₃ |
| A-137 | CF₃ | CH₂CH₃ | CH₃ |
| A-138 | CF₃ | CH₂CH₂CH₃ | CH₃ |
| A-139 | CF₃ | CH(CH₃)₂ | CH₃ |
| A-140 | CF₃ | CH₂CH₂CH₂CH₃ | CH₃ |
| A-141 | CF₃ | CH(CH₃)(CH₂CH₃) | CH₃ |
| A-142 | CF₃ | CH₂CH(CH₃)₂ | CH₃ |
| A-143 | CF₃ | C(CH₃)₃ | CH₃ |
| A-144 | CF₃ | CH₂F | CH₃ |
| A-145 | CF₃ | CHF₂ | CH₃ |
| A-146 | CF₃ | CF₃ | CH₃ |
| A-147 | CF₃ | CH₂CH₂F | CH₃ |
| A-148 | CF₃ | CH₂CHF₂ | CH₃ |
| A-149 | CF₃ | CH₂CF₃ | CH₃ |
| A-150 | CF₃ | c-C₃H₅ | CH₃ |
| A-151 | CF₃ | c-C₄H₇ | CH₃ |
| A-152 | CF₃ | c-C₅H₉ | CH₃ |
| A-153 | CF₃ | c-C₆H₁₁ | CH₃ |
| A-154 | CF₃ | CH₂—c-C₃H₅ | CH₃ |
| A-155 | CF₃ | CH₂—c-C₄H₇ | CH₃ |
| A-156 | CF₃ | CH₂—c-C₅H₉ | CH₃ |

TABLE A-continued

| No. | $R^2$ | $R^5$ | $R^4$ |
|---|---|---|---|
| A-157 | $CF_3$ | $CH_2$—c-$C_6H_{11}$ | $CH_3$ |
| A-158 | $CF_3$ | $CH_2CN$ | $CH_3$ |
| A-159 | $CF_3$ | $CH_2CH_2CN$ | $CH_3$ |
| A-160 | $CF_3$ | $CH_2OCH_3$ | $CH_3$ |
| A-161 | $CF_3$ | $CH(CH_3)OCH_3$ | $CH_3$ |
| A-162 | $CF_3$ | $CH_2CH_2OCH_3$ | $CH_3$ |
| A-163 | $CH_3$ | $OCH_3$ | $OCH_3$ |
| A-164 | $CH_3$ | $OCH_2CH_3$ | $OCH_2CH_3$ |
| A-165 | $CH_3$ | $SCH_3$ | $SCH_3$ |
| A-166 | $CH_3$ | $SCH_2CH_3$ | $SCH_2CH_3$ |
| A-167 | $CH_3$ | $N(CH_3)_2$ | $N(CH_3)_2$ |
| A-168 | $CH_3$ | $N(CH_2CH_3)_2$ | $N(CH_2CH_3)_2$ |
| A-169 | $CHF_2$ | $OCH_3$ | $OCH_3$ |
| A-170 | $CHF_2$ | $OCH_2CH_3$ | $OCH_2CH_3$ |
| A-171 | $CHF_2$ | $SCH_3$ | $SCH_3$ |
| A-172 | $CHF_2$ | $SCH_2CH_3$ | $SCH_2CH_3$ |
| A-173 | $CHF_2$ | $N(CH_3)_2$ | $N(CH_3)_2$ |
| A-174 | $CHF_2$ | $N(CH_2CH_3)_2$ | $N(CH_2CH_3)_2$ |
| A-175 | $CF_3$ | $OCH_3$ | $OCH_3$ |
| A-176 | $CF_3$ | $OCH_2CH_3$ | $OCH_2CH_3$ |
| A-177 | $CF_3$ | $SCH_3$ | $SCH_3$ |
| A-178 | $CF_3$ | $SCH_2CH_3$ | $SCH_2CH_3$ |
| A-179 | $CF_3$ | $N(CH_3)_2$ | $N(CH_3)_2$ |
| A-180 | $CF_3$ | $N(CH_2CH_3)_2$ | $N(CH_2CH_3)_2$ |
| A-181 | $CH_3$ | $OCH_3$ | $OCH_2CH_3$ |
| A-182 | $CH_3$ | $OCH_3$ | $SCH_3$ |
| A-183 | $CH_3$ | $OCH_3$ | $SCH_2CH_3$ |
| A-184 | $CH_3$ | $OCH_3$ | $N(CH_3)_2$ |
| A-185 | $CH_3$ | $OCH_3$ | $N(CH_2CH_3)_2$ |
| A-186 | $CH_3$ | $OCH_2CH_3$ | $SCH_3$ |
| A-187 | $CH_3$ | $OCH_2CH_3$ | $SCH_2CH_3$ |
| A-188 | $CH_3$ | $OCH_2CH_3$ | $N(CH_3)_2$ |
| A-189 | $CH_3$ | $OCH_2CH_3$ | $N(CH_2CH_3)_2$ |
| A-190 | $CH_3$ | $SCH_3$ | $SCH_2CH_3$ |
| A-191 | $CH_3$ | $SCH_3$ | $N(CH_3)_2$ |
| A-192 | $CH_3$ | $SCH_3$ | $N(CH_2CH_3)_2$ |
| A-193 | $CH_3$ | $SCH_2CH_3$ | $N(CH_3)_2$ |
| A-194 | $CH_3$ | $SCH_2CH_3$ | $N(CH_2CH_3)_2$ |
| A-195 | $CH_3$ | $N(CH_3)_2$ | $N(CH_2CH_3)_2$ |
| A-196 | $CHF_2$ | $OCH_3$ | $OCH_2CH_3$ |
| A-197 | $CHF_2$ | $OCH_3$ | $SCH_3$ |
| A-198 | $CHF_2$ | $OCH_3$ | $SCH_2CH_3$ |
| A-199 | $CHF_2$ | $OCH_3$ | $N(CH_3)_2$ |
| A-200 | $CHF_2$ | $OCH_3$ | $N(CH_2CH_3)_2$ |
| A-201 | $CHF_2$ | $OCH_2CH_3$ | $SCH_3$ |
| A-202 | $CHF_2$ | $OCH_2CH_3$ | $SCH_2CH_3$ |
| A-203 | $CHF_2$ | $OCH_2CH_3$ | $N(CH_3)_2$ |
| A-204 | $CHF_2$ | $OCH_2CH_3$ | $N(CH_2CH_3)_2$ |
| A-205 | $CHF_2$ | $SCH_3$ | $SCH_2CH_3$ |
| A-206 | $CHF_2$ | $SCH_3$ | $N(CH_3)_2$ |
| A-207 | $CHF_2$ | $SCH_3$ | $N(CH_2CH_3)_2$ |
| A-208 | $CHF_2$ | $SCH_2CH_3$ | $N(CH_3)_2$ |
| A-209 | $CHF_2$ | $SCH_2CH_3$ | $N(CH_2CH_3)_2$ |
| A-210 | $CHF_2$ | $N(CH_3)_2$ | $N(CH_2CH_3)_2$ |
| A-211 | $CF_3$ | $OCH_3$ | $OCH_2CH_3$ |
| A-212 | $CF_3$ | $OCH_3$ | $SCH_3$ |
| A-213 | $CF_3$ | $OCH_3$ | $SCH_2CH_3$ |
| A-214 | $CF_3$ | $OCH_3$ | $N(CH_3)_2$ |
| A-215 | $CF_3$ | $OCH_3$ | $N(CH_2CH_3)_2$ |
| A-216 | $CF_3$ | $OCH_2CH_3$ | $SCH_3$ |
| A-217 | $CF_3$ | $OCH_2CH_3$ | $SCH_2CH_3$ |
| A-218 | $CF_3$ | $OCH_2CH_3$ | $N(CH_3)_2$ |
| A-219 | $CF_3$ | $OCH_2CH_3$ | $N(CH_2CH_3)_2$ |
| A-220 | $CF_3$ | $SCH_3$ | $SCH_2CH_3$ |
| A-221 | $CF_3$ | $SCH_3$ | $N(CH_3)_2$ |
| A-222 | $CF_3$ | $SCH_3$ | $N(CH_2CH_3)_2$ |
| A-223 | $CF_3$ | $SCH_2CH_3$ | $N(CH_3)_2$ |
| A-224 | $CF_3$ | $SCH_2CH_3$ | $N(CH_2CH_3)_2$ |
| A-225 | $CF_3$ | $N(CH_3)_2$ | $N(CH_2CH_3)_2$ |
| A-226 | $CH_3$ | | $CH_2CH_2CH_2CH_2$ |
| A-227 | $CH_3$ | | $CH_2CH_2CH_2CH_2CH_2$ |
| A-228 | $CH_3$ | | O—$CH_2CH_2CH_2$ |
| A-229 | $CH_3$ | | $CH_2CH_2$—O—$CH_2$ |
| A-230 | $CH_3$ | | O—$CH_2CH_2$—O |
| A-231 | $CH_3$ | | S—$CH_2CH_2$—S |
| A-232 | $CH_3$ | | $N(CH_3)$—$CH_2CH_2$—$N(CH_3)$ |
| A-233 | $CH_3$ | | O—$CH_2CH_2CH_2CH_3$ |
| A-234 | $CH_3$ | | $CH_2CH_2$—O—$CH_2CH_2$ |
| A-235 | $CH_3$ | | $CH_2CH_2CH_2$—O—$CH_2$ |
| A-236 | $CHF_2$ | | $CH_2CH_2CH_2CH_2$ |
| A-237 | $CHF_2$ | | $CH_2CH_2CH_2CH_2CH_2$ |
| A-238 | $CHF_2$ | | O—$CH_2CH_2CH_2$ |
| A-239 | $CHF_2$ | | $CH_2CH_2$—O—$CH_2$ |
| A-240 | $CHF_2$ | | O—$CH_2CH_2$—O |
| A-241 | $CHF_2$ | | S—$CH_2CH_2$—S |
| A-242 | $CHF_2$ | | $N(CH_3)$—$CH_2CH_2$—$N(CH_3)$ |
| A-243 | $CHF_2$ | | O—$CH_2CH_2CH_2CH_3$ |
| A-244 | $CHF_2$ | | $CH_2CH_2$—O—$CH_2CH_2$ |
| A-245 | $CHF_2$ | | $CH_2CH_2CH_2$—O—$CH_2$ |
| A-246 | $CF_3$ | | $CH_2CH_2CH_2CH_2$ |
| A-247 | $CF_3$ | | $CH_2CH_2CH_2CH_2CH_2$ |
| A-248 | $CF_3$ | | O—$CH_2CH_2CH_2$ |
| A-249 | $CF_3$ | | $CH_2CH_2$—O—$CH_2$ |
| A-250 | $CF_3$ | | O—$CH_2CH_2$—O |
| A-251 | $CF_3$ | | S—$CH_2CH_2$—S |
| A-252 | $CF_3$ | | $N(CH_3)$—$CH_2CH_2$—$N(CH_3)$ |
| A-253 | $CF_3$ | | O—$CH_2CH_2CH_2CH_3$ |
| A-254 | $CF_3$ | | $CH_2CH_2$—O—$CH_2CH_2$ |
| A-255 | $CF_3$ | | $CH_2CH_2CH_2$—O—$CH_2$ |

The present invention also relates to a mixture of at least one compound of the present invention with at least one mixing partner as defined herein after. Preferred are binary mixtures of one compound of the present invention as component I with one mixing partner as defined herein after as component II. Preferred weight ratios for such binary mixtures are from 5000:1 to 1:5000, preferably from 1000:1 to 1:1000, more preferably from 100:1 to 1:100, particularly preferably from 10:1 to 1:10. In such binary mixtures, components I and II may be used in equal amounts, or an excess of component I, or an excess of component II may be used.

Mixing partners can be selected from pesticides, in particular insecticides, nematicides, and acaricides, fungicides, herbicides, plant growth regulators, fertilizers, and the like. Preferred mixing partners are insecticides, nematicides and fungicides.

The following list M of pesticides, grouped and numbered according the Mode of Action Classification of the Insecticide Resistance Action Committee (IRAC), together with which the compounds of the present invention can be used and with which potential synergistic effects might be produced, is intended to illustrate the possible combinations, but not to impose any limitation:

M.1 Acetylcholine esterase (AChE) inhibitors from the class of: M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as: M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of M.3A pyrethroids, for example acrinathrin, allethrin, d-cis-trans allethrin, d-trans allethrin, bifenthrin, bioallethrin, bioallethrin Scylclopentenyl, bioresmethrin, cycloprothrin, cyfluthrin, beta-cyfluthrin, cyhalothrin, lambdacyhalothrin, gamma-cyhalothrin, cypermethrin, alpha-cypermethrin, beta-cypermethrin, thetacypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, heptafluthrin, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of M.4A neonicotinoids, for example acetamiprid, clothianidin, cycloxaprid, dinotefuran, imidacloprid, nitenpyram, thiacloprid and thiamethoxam; or the compounds M.4A.2: (2E-)-1-[(6-Chloropyridin-3-yl)methyl]-N'-nitro-2-pentylidenehydrazinecarboximidamide; or M4.A.3: 1-[(6-Chloropyridin-3-yl)methyl]-7-methyl-8-nitro-5-propoxy-1,2,3,5,6,7-hexahydroimidazo[1,2-a]pyridine; or from the class M.4B nicotine;

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as M.7A juvenile hormone analogues as hydroprene, kinoprene and methoprene; or others as M.7B fenoxycarb or M.7C pyriproxyfen;

M.8 miscellaneous non-specific (multi-site) inhibitors, for example M.8A alkyl halides as methyl bromide and other alkyl halides, or M.8B chloropicrin, or M.8C sulfuryl fluoride, or M.8D borax, or M.8E tartar emetic;

M.9 Selective homopteran feeding blockers, for example M.9B pymetrozine, or M.9C flonicamid;

M.10 Mite growth inhibitors, for example M.10A clofentezine, hexythiazox and diflovidazin, or M.10B etoxazole;

M.11 Microbial disruptors of insect midgut membranes, for example *bacillus thuringiensis* or *bacillus sphaericus* and the insecticdal proteins they produce such as *bacillus thuringiensis* subsp. *israelensis, bacillus sphaericus, bacillus thuringiensis* subsp. *aizawai, bacillus thuringiensis* subsp. *kurstaki* and *bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example M.12A diafenthiuron, or M.12B organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example M.20A hydramethylnon, or M.20B acequinocyl, or M.20C fluacrypyrim;

M.21 Mitochondrial complex I electron transport inhibitors, for example M.21A METI acaricides and insecticides such as fenazaquin, fenpyroximate, pyrimidifen, pyridaben, tebufenpyrad or tolfenpyrad, or M.21B rotenone;

M.22 Voltage-dependent sodium channel blockers, for example M.22A indoxacarb, or M.22B metaflumizone, or M.22B.1: 2-[2-(4-Cyanophenyl)-1-[3-(trifluoromethyl)phenyl]ethylidene]-N-[4-(difluoromethoxy)phenyl]-hydrazinecarboxamide or M.22B.2: N-(3-Chloro-2-methylphenyl)-2-[(4-chlorophenyl)[4-[methyl(methylsulfonyl)amino]phenyl]methylene]-hydrazinecarboxamide;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example M.24A phosphine such as aluminium phosphide, calcium phosphide, phosphine or zinc phosphide, or M.24B cyanide;

M.25 Mitochondrial complex II electron transport inhibitors, such as beta-ketonitrile derivatives, for example cyenopyrafen or cyflumetofen;

M.28 Ryanodine receptor-modulators from the class of diamides, as for example flubendiamide, chlorantraniliprole (Rynaxypyr®), cyantraniliprole (Cyazypyr®), tetraniliprole, or the phthalamide compounds M.28.1: (R)-3-Chlor-N1-{2-methyl-4-[1,2,2,2 tetrafluor-1-(trifluormethyl)ethyl]phenyl}-N2-(1-methyl-2-methylsulfonylethyl)phthalamid and M.28.2: (S)-3-Chlor-N1-{2-methyl-4-[1,2,2,2 tetrafluor-1-(trifluormethyl)ethyl]phenyl}-N2-(1-methyl-2-methylsulfonylethyl)phthalamid, or the compound M.28.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound M.28.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate; or a compound selected from M.28.5a) to M.28.5d) and M.28.5h) to M.28.5l): M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; M.28.5b) N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide; M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide; M.28.5d) N-[4,6-dichloro-2-[(di-2-propyl-lambda-4-sulfanylidene)carbamoyl]-phenyl]-2-(3- chloro-2-pyridyl)-5-(trifluoromethyl)pyrazole-3-carboxamide; M.28.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide; M.28.5i) N-[2-(5-Amino-1,3,4-thiadiazol-2-yl)-4-chloro-6-methylphenyl]-3-bromo-1-(3-chloro-2-pyridinyl)-1H-pyrazole-5-carboxamide; M.28.5j) 3-Chloro-1-(3-chloro-2-pyridinyl)-N-[2,4-dichloro-6-[[(1-cyano-1-methylethyl)amino]carbonyl]phenyl]-1H-pyrazole-5-carboxamide; M.28.5k) 3-Bromo-N-[2,4-dichloro-6-(methylcarbamoyl)phenyl]-1-(3,5-dichloro-2-pyridyl)-1H-pyrazole-5-carboxamide; M.28.5l) N-[4-Chloro-2-[[(1,1-dimethylethyl)amino]carbonyl]-6-methylphenyl]-1-(3-chloro-2-pyridinyl)-3-(fluoromethoxy)-1H-pyrazole-5-carboxamide; or a compound selected from M.28.6: N-(2-cyanopropan-2-yl)-N-(2,4-dimethylphenyl)-3-iodobenzene-1,2-dicarboxamide; or M.28.7: 3-Chloro-N-(2-cyanopropan-2-yl)-N-(2,4-dimethylphenyl)-benzene-1,2-dicarboxamide;

M.29. insecticidal active compounds of unknown or uncertain mode of action, as for example afidopyropen, afoxolaner, azadirachtin, amidoflumet, benzoximate, bifenazate, broflanilide, bromopropylate, chinomethionat, cryolite, dicloromezotiaz, dicofol, flufenerim, flometoquin, fluensulfone, fluhexafon, fluopyram, flupyradifurone, fluralaner, metoxadiazone, piperonyl butoxide, pyflubumide, pyridalyl, pyrifluquinazon, sulfoxaflor, tioxazafen, triflumezopyrim, or the compounds M.29.3: 11-(4-chloro-2,6-dimethylphenyl)-12-hydroxy-1,4-dioxa-9-azadispiro[4.2.4.2]-tetradec-11-en-10-one, or the compound M.29.4: 3-(4'-fluoro-2,4-dimethylbiphenyl-3-yl)-4-hydroxy-8-oxa-1-azaspiro[4.5]dec-3-en-2-one, or the compound M.29.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of *bacillus firmus* (Votivo, 1-1582); or a compound selected from the group of M.29.6, wherein the compound is selected from M.29.6a) to M.29.6k): M.29.6a) (E/Z)—N-[1-[(6-chloro-3-pyridyl)methyl]-2-pyridylidene]-2,2,2-trifluoro-acetamide; M.29.6b) (E/Z)—N-[1-[(6-chloro-5-fluoro-3-pyridyl)methyl]-2-pyridylidene]-2,2,2-trifluoro-acetamide; M.29.6c) (E/Z)-2,2,2-trifluoro-N-[1-[(6-fluoro-3-pyridyl)methyl]-2-pyridylidene]acetamide; M.29.6d) (E/Z)—N-[1-[(6-bromo-3-pyridyl)methyl]-2-pyridylidene]-2,2,2-trifluoro-acetamide; M.29.6e) (E/Z)—N-[1-[1-(6-chloro-3-pyridyl)ethyl]-2-pyridylidene]-2,2,2-trifluoro-acetamide; M.29.6f) (E/Z)—N-[1-[(6-chloro-3-pyridyl)methyl]-2-pyridylidene]-2,2-difluoroacetamide; M.29.6g) (E/Z)-2-chloro-N-[1-[(6-chloro-3-pyridyl)methyl]-2-pyridylidene]-2,2-difluoroacetamide; M.29.6h) (E/Z)—N-[1-[(2-chloropyrimidin-5-yl)methyl]-2-pyridylidene]-2,2,2-trifluoro-acetamide; M.29.6i) (E/Z)—N-[1-[(6-chloro-3-pyridyl)methyl]-2-pyridylidene]-2,2,3,3,3-pentafluoropropanamide.); M.29.6j) N-[1-[(6-chloro-3-pyridyl)methyl]-2-pyridylidene]-2,2,2-trifluoro-thioacetamide; or M.29.6k) N-[1-[(6-chloro-3-pyridyl)methyl]-2-pyridylidene]-2,2,2-trifluoro-N'-isopropyl-acetamidine; or the compounds M.29.8: 8-chloro-N-[2-chloro-5-methoxyphenyl)sulfonyl]-6-trifluoromethyl)-imidazo[1,2-a]pyridine-2-carboxamide; or the compounds M.29.9.a): 4-[5-(3,5-dichlorophenyl)-5-(trifluoromethyl)-4H-isoxazol-3-yl]-2-methyl-N-(1-oxothietan-3-yl)benzamide; or M.29.9.b): 4-[5-(3,5-Dichlorophenyl)-5-trifluoromethyl-4,5-dihydroisoxazol-3-yl]-N-[(methoxyimino)methyl]-2-methylbenzamide; or M.29.10: 5-[3-[2,6-dichloro-4-(3,3-dichloroallyloxy)phenoxy]propoxy]-1H-pyrazole; or a compound selected from the group of M.29.11, wherein the compound is selected from M.29.11 b) to M.29.11p): M.29.11.b) 3-(benzoylmethylamino)-N-[2-bromo-4-[1,2,2,3,3,3-hexafluoro-1-(trifluoromethyl)propyl]-6-(trifluoromethyl)phenyl]-2-fluoro-benzamide; M.29.11.c) 3-(benzoylmethylamino)-2-fluoro-N-[2-iodo-4-[1,2,2,2-tetrafluoro-1-(trifluoromethyl)ethyl]-6-(trifluoromethyl)phenyl]-benzamide; M.29.11.d) N-[3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.29.11.e) N-[3-[[[2-bromo-4-[1,2,2,2-tetrafluoro-1-(trifluoromethyl)ethyl]-6-(trifluoromethyl)phenyl]amino]carbonyl]-2-fluorophenyl]-4-fluoro-N-methyl-benzamide; M.29.11.f) 4-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.29.11.g) 3-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.29.11.h) 2-chloro-N-[3-[[[2-iodo-4-[1,2,2,2-tetrafluoro-1-(trifluoromethyl)ethyl]-6-(trifluoromethyl)phenyl]amino]carbonyl]phenyl]-3-pyridinecarboxamide; M.29.11.i) 4-cyano-N-[2-cyano-5-[[2,6-dibromo-4-[1,2,2,3,3,3-hexafluoro-1-(trifluoromethyl)propyl]phenyl]carbamoyl]phenyl]-2-methyl-benzamide; M.29.11.j) 4-cyano-3-[(4-cyano-2-methylbenzoyl)amino]-N-[2,6-dichloro-4-[1,2,2,3,3,3-hexafluoro-1-(trifluoromethyl)propyl]phenyl]-2-fluoro-benzamide; M.29.11.k) N-[5-[[2-chloro-6-cyano-4-[1,2,2,3,3,3-hexafluoro-1-(trifluoromethyl)propyl]phenyl]carbamoyl]-2-cyano-phenyl]-4-cyano-2-methyl-benzamide; M.29.11.l) N-[5-[[2-bromo-6-chloro-4-[2,2,2-trifluoro-1-hydroxy-1-(trifluoromethyl)ethyl]phenyl]carbamoyl]-2-cyano-phenyl]-4-cyano-2-methyl-benzamide; M.29.11.m) N-[5-[[2-bromo-6-chloro-4-[1,2,2,3,3,3-hexafluoro-1-(trifluoromethyl)propyl]phenyl]carbamoyl]-2-cyano-phenyl]-4-cyano-2-methyl-benzamide; M.29.11.n) 4-cyano-N-[2-cyano-5-[[2,6-dichloro-4-[1,2,2,3,3,3-hexafluoro-1-(trifluoromethyl)propyl]phenyl]carbamoyl]phenyl]-2-methyl-benzamide; M.29.11.o) 4-cyano-N-[2-cyano-5-[[2,6-dichloro-4-[1,2,2,2-tetrafluoro-1-(trifluoromethyl)ethyl]phenyl]carbamoyl]phenyl]-2-methyl-benzamide; M.29.11.p) N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide; or a compound selected from the group of M.29.12, wherein the compound is selected from M.29.12a) to M.29.12m): M.29.12.a) 2-(1,3-Dioxan-2-yl)-6-[2-(3-pyridinyl)-5-thiazolyl]-pyridine; M.29.12.b) 2-[6-[2-(5-Fluoro-3-pyridinyl)-5-thiazolyl]-2-pyridinyl]-pyrimidine; M.29.12.c) 2-[6-[2-(3-Pyridinyl)-5-thiazolyl]-2-pyridinyl]-pyrimidine; M.29.12.d) N-Methylsulfonyl-6-[2-(3-pyridyl)thiazol-5-yl]pyridine-2-carboxamide; M.29.12.e) N-Methylsulfonyl-6-[2-(3-pyridyl)thiazol-5-yl]pyridine-2-carboxamide; M.29.12.f) N-Ethyl-N-[4-methyl-2-(3-pyridyl)thiazol-5-yl]-3-methyl-thio-propanamide; M.29.12.g) N-Methyl-N-[4-methyl-2-(3-pyridyl)thiazol-5-yl]-3-methylthio-propanamide; M.29.12.h) N,2-Dimethyl-N-[4-methyl-2-(3-pyridyl)thiazol-5-yl]-3-methylthio-propanamide; M.29.12.i) N-Ethyl-2-methyl-N-[4-methyl-2-(3-pyridyl)thiazol-5-yl]-3-methylthio-propanamide; M.29.12.j) N-[4-Chloro-2-(3-pyridyl)thiazol-5-yl]-N-ethyl-2-methyl-3-methylthio-propanamide; M.29.12.k) N-[4-Chloro-2-(3-pyridyl)thiazol-5-yl]-N,2-dimethyl-3-methylthio-propanamide; M.29.12.l) N-[4-Chloro-2-(3-pyridyl)thiazol-5-yl]-N-methyl-3-methylthiopropanamide; M.29.12.m) N-[4-Chloro-2-(3-pyridyl)thiazol-5-yl]-N-ethyl-3-methylthio-propanamide; or the compounds M.29.14a) 1-[(6-Chloro-3-pyridinyl)methyl]-1,2,3,5,6,7-hexahydro-5-methoxy-7-methyl-8-nitro-imidazo[1,2-a]pyridine; or M.29.14b) 1-[(6-Chloropyridin-3-yl)methyl]-7-methyl-8-nitro-1,2,3,5,6,7-hexahydroimidazo[1,2-a]pyridin-5-ol; or the compounds M.29.16a) 1-isopropyl-N,5-dimethyl-N-pyridazin-4-yl-pyrazole-4-carboxamide; or M.29.16b) 1-(1,2-dimethylpropyl)-N-ethyl-5-methyl-N-pyridazin-4-yl-pyrazole-4-carboxamide; M.29.16c) N,5-dimethyl-N-pyridazin-4-yl-1-(2,2,2-trifluoro-1-methyl-ethyl)pyrazole-4-carboxamide; M.29.16d) 1-[1-(1-cyanocyclopropyl)ethyl]-N-ethyl-5-methyl-N-pyridazin-4-yl-pyrazole-4-carboxamide; M.29.16e) N-ethyl-1-(2-fluoro-1-methyl-propyl)-5-methyl-N-pyridazin-4-yl-pyrazole-4-carboxamide; M.29.16f) 1-(1,2-dimethylpropyl)-N,5-dimethyl-N-pyridazin-4-yl-pyrazole-4-carboxamide; M.29.16g) 1-[1-(1-cyanocyclopropyl)ethyl]-N,5-dimethyl-N-pyridazin-4-yl-pyrazole-4-carboxamide; M.29.16h) N-methyl-1-(2-fluoro-1-methyl-propyl)-5-methyl-N-pyridazin-4-yl-pyrazole-4-carboxamide; M.29.16i) 1-(4,4-difluorocyclohexyl)-N-ethyl-5-methyl-N-pyridazin-4-yl-pyrazole-4-carboxamide; or M.29.16j) 1-(4,4-difluorocyclohexyl)-N,5-dimethyl-N-pyridazin-4-yl-pyrazole-4-carboxamide.

The commercially available compounds of the group M listed above may be found in The Pesticide Manual, 16th Edition, C. MacBean, British Crop Protection Council (2013) among other publications. The online Pesticide Manual is updated regularly and is accessible through http://bcpcdata.com/pesticide-manual.html.

Another online data base for pesticides providing the ISO common names is http://www.alanwood.net/pesticides.

The M.4 neonicotinoid cycloxaprid is known from WO2010/069266 and WO2011/069456, the neonicotinoid M.4A.2, sometimes also to be named as guadipyr, is known from WO2013/003977, and the neonicotinoid M.4A.3 (approved as paichongding in China) is known from WO2007/101369. The metaflumizone analogue M.22B.1 is described in CN10171577 and the analogue M.22B.2 in CN102126994. The phthalamides M.28.1 and M.28.2 are both known from WO2007/101540. The anthranilamide M.28.3 is described in WO2005/077934. The hydrazide compound M.28.4 is described in WO2007/043677. The anthranilamides M.28.5a) to M.28.5d) and M.28.5h) are described in WO 2007/006670, WO2013/024009 and WO2013/024010, the anthranilamide M.28.5i) is described in WO2011/085575, M.28.5j) in WO2008/134969, M.28.5k) in US2011/046186 and M.28.5l) in WO2012/034403. The diamide compounds M.28.6 and M.28.7 can be found in CN102613183. The spiroketal-substituted cyclic ketoenol derivative M.29.3 is known from WO2006/089633 and the biphenyl-substituted spirocyclic ketoenol derivative M.29.4 from WO2008/067911. The triazoylphenylsulfide M.29.5 is described in WO2006/043635, and biological control agents on the basis of *bacillus firmus* are described in WO2009/124707. The compounds M.29.6a) to M.29.6i) listed under M.29.6 are described in WO2012/029672, and M.29.6j) and M.29.6k) in WO2013/129688. The nematicide M.29.8 is known from WO2013/055584. The isoxazoline M.29.9.a) is described in WO2013/050317. The isoxazoline M.29.9.b) is described in WO2014/126208. The pyridalyl-type analogue M.29.10 is known from WO2010/060379. The carboxamides broflanilide and M.29.11.b) to M.29.11.h) are described in WO2010/018714, and the carboxamides M.29.11i) to M.29.11.p) in WO2010/127926.

The pyridylthiazoles M.29.12.a) to M.29.12.c) are known from WO2010/006713, M.29.12.d) and M.29.12.e) are known from WO2012/000896, and M.29.12.f) to M.29.12.m) from WO2010/129497. The compounds M.29.14a) and M.29.14b) are known from WO2007/101369. The pyrazoles M.29.16.a) to M.29.16h) are described in WO2010/034737, WO2012/084670, and WO2012/143317, respectively, and the pyrazoles M.29.16i) and M.29.16j) are described in U.S. 61/891,437.

The following list of fungicides, in conjunction with which the compounds of the present invention can be used, is intended to illustrate the possible combinations but does not limit them:

A) Respiration Inhibitors

Inhibitors of complex III at Q. site (e. g. strobilurins): azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxy.strobin (A.1.13), pyraclostrobin (A.1.14), pyrametostrobin (A.1.15), pyraoxystrobin (A.1.16), trifloxystrobin (A.1.17), 2-(2-(3-(2,6-dichlorophenyl)-1-methyl-allylideneaminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5-phenylpyrazol-3-yl)oxylmethyl]phenyl]-N-methoxy-carbamate (A.1.22), 1-[3-chloro-2-[[1-(4-chlorophenyl)-1H-pyrazol-3-yl]oxymethyl]phenyl]-4-methyl-tetrazol-5-one (A.1.23), 1-[3-bromo-2-[[1-(4-chlorophenyl)pyrazol-3-yl]oxymethyl]phenyl]-4-methyl-tetrazol-5-one (A.1.24), 1-[2-[[1-(4-chlorophenyl)pyrazol-3-yl]oxymethyl]-3-methyl-phenyl]-4-methyl-tetrazol-5-one (A.1.25), 1-[2-[[1-(4-chlorophenyl)pyrazol-3-yl]oxymethyl]-3-fluoro-phenyl]-4-methyl-tetrazol-5-one (A.1.26), 1-[2-[[1-(2,4-dichlorophenyl)pyrazol-3-yl]oxymethyl]-3-fluoro-phenyl]-4-methyl-tetrazol-5-one (A.1.27), 1-[2-[[4-(4-chlorophenyl)thiazol-2-yl]oxymethyl]-3-methyl-phenyl]-4-methyl-tetrazol-5-one (A.1.28), 1-[3-chloro-2-[[4-(p-tolypthiazol-2-yl]oxymethyl]phenyl]-4-methyl-tetrazol-5-one (A.1.29), 1-[3-cyclopropyl-2-[[2-methyl-4-(1-methylpyrazol-3-yl)phenoxy]methyl]phenyl]-4-methyl-tetrazol-5-one (A.1.30), 1-[3-(difluoromethoxy)-2-[[2-methyl-4-(1-methyl-pyrazol-3-yl)phenoxy]methyl]phenyl]-4-methyl-tetrazol-5-one (A.1.31), 1-methyl-4-[3-methyl-2-[[2-methyl-4-(1-methylpyrazol-3-yl)phenoxy]methyl]phenyl]tetrazol-5-one (A.1.32), 1-methyl-4-[3-methyl-2-[[1-[3-(trifluoromethyl)phenyl]-ethylideneamino]oxymethyl]phenyl]tetrazol-5-one (A.1.33), (Z,2E)-5-[1-(2,4-dichlorophenyl)pyrazol-3-yl]-oxy-2-methoxyimino-N,3-dimethyl-pent-3-enamide (A.1.34), (Z,2E)-5-[1-(4-chlorophenyl)pyrazol-3-yl]oxy-2-methoxyimino-N,3-dimethyl-pent-3-enamide (A.1.35), (Z,2E)-5-[1-(4-chloro-2-fluoro-phenyl)pyrazol-3-yl]oxy-2-methoxyimino-N,3-dimethyl-pent-3-enamide (A.1.36), inhibitors of complex III at Q, site: cyazofamid (A.2.1), amisulbrom (A.2.2), [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate (A.2.3), [(3S,6S,7R,8R)-8-benzyl-3-[[3-(acetoxymethoxy)-4-methoxy-pyridine-2-carbonyl] amino]-6-methyl-4,9-dioxo-1,5-dioxonan-7-yl]

2-methylpropanoate (A.2.4), [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate (A.2.5), [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate (A.2.6); (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate (A.2.7), (3S,6S,7R,8R)-8-benzyl-3-[3-[(isobutyryloxy)methoxy]-4-methoxypicolinamido]-6-methyl-4,9-dioxo-1,5-dioxonan-7-yl isobutyrate (A.2.8);

inhibitors of complex II (e. g. carboxamides): benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.14), penthiopyrad (A.3.15), sedaxane (A.3.16), tecloftalam (A.3.17), thifluzamide (A.3.18), N-(4'-trifluoromethylthiobiphenyl-2-yl)-3-difluoromethyl-1-methyl-1H-pyrazole-4-carboxamide (A.3.19), N-(2-(1,3,3-trimethyl-butyl)phenyl)-1,3-dimethyl-5-fluoro-1H-pyrazole-4-carboxamide (A.3.20), 3-(difluoromethyl)-1-methyl-N-(1,1,3-trimethylindan-4-yl)pyrazole-4-carboxamide (A.3.21), 3-(trifluoromethyl)-1-methyl-N(1,1,3-trimethylindan-4-yl)pyrazole-4-carboxamide (A.3.22), 1,3-dimethyl-N-(1,1,3-trimethylindan-4-yl)pyrazole-4-carboxamide (A.3.23), 3-(trifluoromethyl)-1,5-dimethyl-N-(1,1,3-trimethylindan-4-yl)pyrazole-4-carboxamide (A.3.24), 1,3,5-trimethyl-N-(1,1,3-trimethylindan-4-yl)pyrazole-4-carboxamide (A.3.25), N-(7-fluoro-1,1,3-trimethyl-indan-4-yl)-1,3-dimethylpyrazole-4-carboxamide (A.3.26), N-[2-(2,4-dichlorophenyl)-2-methoxy-1-methylethyl]-3-(difluoromethyl)-1-methyl-pyrazole-4-carboxamide (A.3.27);

other respiration inhibitors (e. g. complex I, uncouplers): diflumetorim (A.4.1), (5,8-difluoroquinazolin-4-yl)-{2-[2-fluoro-4-(4-trifluoromethylpyridin-2-yloxy)-phenyl]-ethyl}-amine (A.4.2); nitrophenyl derivates: binapacryl (A.4.3), dinobuton (A.4.4), dinocap (A.4.5), fluazinam (A.4.6); ferimzone (A.4.7); organometal compounds: fentin salts, such as fentin-acetate (A.4.8), fentin chloride (A.4.9) or fentin hydroxide (A.4.10); ametoctradin (A.4.11); and silthiofam (A.4.12);

B) Sterol Biosynthesis Inhibitors (SBI Fungicides)

C14 demethylase inhibitors (DMI fungicides): triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 1-[rel-(2S,3A)-3-(2-chlorophenyl)-2-(2,4-difluorophenyl)-oxiranylmethyl]-5-thiocyanato-1H-[1,2,4]triazole (B.1.31), 2-[rel(2S;3A)-3-(2-chlorophenyl)-2-(2,4-difluorophenyl)-oxiranylmethyl]-2H-[1,2,4]triazole-3-thiol (B.1.32), 2-[2-chloro-4-(4-chlorophenoxy)phenyl]-1-(1,2,4-triazol-1-yl)pentan-2-ol (B.1.33), 1-[4-(4-chlorophenoxy)-2-(trifluoromethyl)phenyl]-1-cyclopropyl-2-(1,2,4-triazol-1-yl)ethanol (B.1.34), 2-[4-(4-chlorophenoxy)-2-(trifluoromethyl)phenyl]-1-(1,2,4-triazol-1-yl)butan-2-ol (B.1.35), 2-[2-chloro-4-(4-chlorophenoxy)phenyl]-1-(1,2,4-triazol-1-yl)butan-2-ol (B.1.36), 2-[4-(4-chlorophenoxy)-2-(trifluoromethyl)phenyl]-3-methyl-1-(1,2,4-triazol-1-yl)butan-2-ol (B.1.37), 2-[4-(4-chlorophenoxy)-2-(trifluoromethyl)phenyl]-1-(1,2,4-triazol-1-yl)propan-2-ol (B.1.38), 2-[2-chloro-4-(4-chlorophenoxy)phenyl]-3-methyl-1-(1,2,4-triazol-1-yl)butan-2-ol (B.1.39), 2-[4-(4-chlorophenoxy)-2-(trifluoromethyl)phenyl]-1-(1,2,4-triazol-1-yl)pentan-2-ol (B.1.40), 2-[4-(4-fluorophenoxy)-2-(trifluoromethyl)phenyl]-1-(1,2,4-triazol-1-yl)propan-2-ol (B.1.41), 2-[2-chloro-4-(4-chlorophenoxy)phenyl]-1-(1,2,4-triazol-1-yl)pent-3-yn-2-ol (B.1.51); imidazoles: imazalil (B.1.42), pefurazoate (B.1.43), prochloraz (B.1.44), triflumizol (B.1.45); pyrimidines, pyridines and piperazines: fenarimol (B.1.46), nuarimol (B.1.47), pyrifenox (B.1.48), triforine (B.1.49), [3-(4-chloro-2-fluoro-phenyl)-5-(2,4-difluorophenyl)isoxazol-4-yl]-(3-pyridyl)methanol (B.1.50);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

C) Nucleic Acid Synthesis Inhibitors phenylamides or acyl amino acid fungicides: benalaxyl (C.1.1), benalaxyl-M (C.1.2), kiralaxyl (C.1.3), metalaxyl (C.1.4), metalaxyl-M (mefenoxam, C.1.5), ofurace (C.1.6), oxadixyl (C.1.7);

others: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7);

D) Inhibitors of Cell Division and Cytoskeleton tubulin inhibitors, such as benzimidazoles, thiophanates: benomyl (D1.1), carbendazim (D1.2), fuberidazole (D1.3), thiabendazole (D1.4), thiophanate-methyl (D1.5); triazolopyrimidines: 5-chloro-7-(4-methylpiperidin-1-yl)-6-(2,4,6-trifluorophenyl)-[1,2,4]triazolo[1,5-a]pyrimidine (D1.6);

other cell division inhibitors: diethofencarb (D2.1), ethaboxam (D2.2), pencycuron (D2.3), fluopicolide (D2.4), zoxamide (D2.5), metrafenone (D2.6), pyriofenone (D2.7);

E) Inhibitors of Amino Acid and Protein Synthesis methionine synthesis inhibitors (anilino-pyrimidines): cyprodinil (E.1.1), mepanipyrim (E.1.2), pyrimethanil (E.1.3);

protein synthesis inhibitors: blasticidin-S(E.2.1), kasugamycin (E.2.2), kasugamycin hydrochloride-hydrate (E.2.3), mildiomycin (E.2.4), streptomycin (E.2.5), oxytetracyclin (E.2.6), polyoxine (E.2.7), validamycin A (E.2.8);

F) Signal Transduction Inhibitors

MAP/histidine kinase inhibitors: fluoroimid (F.1.1), iprodione (F.1.2), procymidone (F.1.3), vinclozolin (F.1.4), fenpiclonil (F.1.5), fludioxonil (F.1.6);

G protein inhibitors: quinoxyfen (F.2.1);

G) Lipid and Membrane Synthesis Inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7) and N-(1-(1-(4-cyano-phenyl)ethanesulfonyl)-but-2-yl) carbamic acid-(4-fluorophenyl) ester (G.3.8);

compounds affecting cell membrane permeability and fatty acids: propamocarb (G.4.1);

fatty acid amide hydrolase inhibitors: oxathiapiprolin (G.5.1), 2-{3-[2-(1-{[3,5-bis(difluoromethyl-1H-pyrazol-1-yl]acetyl}piperidin-4-yl)-1,3-thiazol-4-yl]-4,5-dihydro-1,2-oxazol-5-yl}phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl methanesulfonate (G.5.3).

H) Inhibitors with Multi Site Action inorganic active substances: Bordeaux mixture (H.1.1), copper acetate (H.1.2), copper hydroxide (H.1.3), copper oxychloride (H.1.4), basic copper sulfate (H.1.5), sulfur (H.1.6);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds (e. g. phthalimides, sulfamides, chloronitriles): anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11), N-(4-chloro-2-nitro-phenyl)-N-ethyl-4-methylbenzenesulfonamide (H.3.12);

guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H[1,4]dithiino[2,3-c:5,6-c']dipyrrole-1,3,5,7(2H,6H)-tetraone (H.4.10);

I) Cell Wall Synthesis Inhibitors inhibitors of glucan synthesis: validamycin (I.1.1), polyoxin B (I.1.2);

melanin synthesis inhibitors: pyroquilon (I.2.1), tricyclazole (I.2.2), carpropamid (I.2.3), dicyclomet (I.2.4), fenoxanil (I.2.5);

J) Plant Defence Inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), potassium or sodium bicarbonate (J.1.9);

K) Unknown Mode of Action bronopol (K.1.1), chinomethionat (K.1.2), cyflufenamid (K.1.3), cymoxanil (K.1.4), dazomet (K.1.5), debacarb (K.1.6), diclomezine (K.1.7), difenzoquat (K.1.8), difenzoquat-methylsulfate (K.1.9), diphenylamin (K.1.10), fenpyrazamine (K.1.11), flumetover (K.1.12), flusulfamide (K.1.13), flutianil (K.1.14), methasulfocarb (K.1.15), nitrapyrin (K.1.16), nitrothal-isopropyl (K.1.18), oxathiapiprolin (K.1.19), tolprocarb (K.1.20), oxin-copper (K.1.21), proquinazid (K.1.22), tebufloquin (K.1.23), tecloftalam (K.1.24), triazoxide (K.1.25), 2-butoxy-6-iodo-3-propylchromen-4-one (K.1.26), 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone (K.1.27), 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone (K.1.28), 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone (K.1.29), N-(cyclo-propylmethoxyimino-(6-difluoro-methoxy-2,3-difluoro-phenyl)-methyl)-2-phenyl acetamide (K.1.30), N'-(4-(4-chloro-3-trifluoromethyl-phenoxy)-2,5-dimethyl-phenyl)-N-ethyl-N-methyl formamidine (K.1.31), N'-(4-(4-fluoro-3-trifluoromethyl-phenoxy)-2,5-dimethyl-phenyl)-N-ethyl-N-methyl formamidine (K.1.32), N'-(2-methyl-5-trifluoromethyl-4-(3-trimethylsilanyl-propoxy)phenyl)-N-ethyl-N-methyl formamidine (K.1.33), N'-(5-difluoromethyl-2-methyl-4-(3-trimethylsilanyl-propoxy)-phenyl)-N-ethyl-N-methyl formamidine (K.1.34), methoxy-acetic acid 6-tert-butyl-8-fluoro-2,3-dimethyl-quinolin-4-yl ester (K.1.35), 3-[5-(4-methylphenyl)-2,3-dimethyl-isoxazolidin-3-yl]-pyridine (K.1.36), 3-[5-(4-chloro-phenyl)-2,3-dimethyl-isoxazolidin-3-yl]-pyridine (pyrisoxazole) (K.1.37), N-(6-methoxy-pyridin-3-yl) cyclopropanecarboxylic acid amide (K.1.38), 5-chloro-1-(4,6-dimethoxy-pyrimidin-2-yl)-2-methyl-1H-benzoimidazole (K.1.39), 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate (K.1.40), picarbutrazox (K.1.41), pentyl N-[6-[[(Z)[(1-methyl-tetrazol-5-yl)-phenyl-methylene]amino]oxymethyl]-2-pyridyl]carbamate (K.1.42), 2-[2-[(7,8-difluoro-2-methyl-3-quinolyl)oxy]-6-fluoro-phenyl]propan-2-ol (K.1.43), 2-[2-fluoro-6-[(8-fluoro-2-methyl-3-quinolyl)oxy]phen-yl]propan-2-ol (K.1.44), 3-(5-fluoro-3,3,4,4-tetramethyl-3,4-dihydroisoquinolin-1-yl)quinoline (K.1.45), 3-(4,4-difluoro-3,3-dimethyl-3,4-dihydroisoquinolin-1-yl)quinoline (K.1.46), 3-(4,4,5-trifluoro-3,3-dimethyl-3,4-dihydroisoquinolin-1-yl) quinoline (K.1.47), 9-fluoro-2,2-dimethyl-5-(3-quinolyl)-3H-1,4-benzoxazepine (K.1.48).

The fungicides described by common names, their preparation and their activity e.g. against harmful fungi is known (cf.: http://www.alanwood.net/pesticides/); these substances are commercially available.

The fungicides described by IUPAC nomenclature, their preparation and their pesticidal activity is also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. No. 3,296,272; U.S. Pat. No. 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303, WO 09/90181, WO 13/007767, WO 13/010862, WO 13/127704, WO 13/024009, WO 13/024010 and WO 13/047441, WO 13/162072, WO 13/092224, WO 11/135833).

Suitable mixing partners for the compounds of the present invention also include biopesticides.

Biopesticides have been defined as a form of pesticides based on micro-organisms (bacteria, fungi, viruses, nematodes, etc.) or natural products (compounds, such as metabolites, proteins, or extracts from biological or other natural sources) (U.S. Environmental Protection Agency: http://www.epa.gov/pesticides/biopesticides/). Biopesticides fall into two major classes, microbial and biochemical pesticides:

(1) Microbial pesticides consist of bacteria, fungi or viruses (and often include the metabolites that bacteria and fungi produce). Entomopathogenic nematodes are also classified as microbial pesticides, even though they are multicellular.

(2) Biochemical pesticides are naturally occurring substances or or structurally-similar and functionally identical to a naturally-occurring substance and extracts from biological sources that control pests or provide other crop protection uses as defined below, but have non-toxic mode of actions (such as growth or developmental regulation, attractants, repellents or defence activators (e.g. induced resistance) and are relatively non-toxic to mammals.

Biopesticides for use against crop diseases have already established themselves on a variety of crops. For example, biopesticides already play an important role in controlling downy mildew diseases. Their benefits include: a 0-Day Pre-Harvest Interval, the ability to use under moderate to severe disease pressure, and the ability to use in mixture or in a rotational program with other registered pesticides.

A major growth area for biopesticides is in the area of seed treatments and soil amendments. Biopesticidal seed treatments are e.g. used to control soil borne fungal pathogens that cause seed rots, damping-off, root rot and seedling blights. They can also be used to control internal seed borne fungal pathogens as well as fungal pathogens that are on the surface of the seed. Many biopesticidal products also show capacities to stimulate plant host defenses and other physiological processes that can make treated crops more resistant to a variety of biotic and abiotic stresses or can regulate plant growth. Many biopesticidal products also show capacities to stimulate plant health, plant growth and/or yield enhancing activity.

The following list of biopesticides, in conjunction with which the compounds of the present invention can be used, is intended to illustrate the possible combinations but does not limit them:

L) Biopesticides

L1) Microbial pesticides with fungicidal, bactericidal, viricidal and/or plant defense activator activity: *Ampelomyces quisqualis, Aspergillus flavus, Aureobasidium pullulans, Bacillus altitudinis, B. amyloliquefaciens, B. megaterium, B. mojavensis, B. mycoides, B. pumilus, B. simplex, B. solisalsi, B. subtilis, B. subtilis* var. *amyloliquefaciens, Candida oleophlla, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea* f. *catenulate* (also named *Gliocladium catenulatum), Gliocladium roseum, Lysobacter antibioticus, L. enzymogenes, Metschnikowia fructicola, Microdochium dimerum, Microsphaeropsis ochracea, Muscodor albus, Paenibacillus alvei, Paenibacillus polymyxa, Pantoea vagans, Penicillium bilaiae, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. violaceusniger, Talaromyces flavus, Trichoderma asperelloides, T. asperellum, T. atroviride, T. fertile, T. gamsii, T. harmatum, T. harzianum, T. polysporum, T. stromaticum, T. virens, T. viride, Typhula phacorrhiza, Ulocladium oudemansii, Verticillium dahlia*, zucchini yellow mosaic virus (avirulent strain);

L2) Biochemical pesticides with fungicidal, bactericidal, viricidal and/or plant defense activator activity: harpin protein, *Reynoutria sachalinensis* extract;

L3) Microbial pesticides with insecticidal, acaricidal, molluscidal and/or nematicidal activity: *Agrobacterium radiobacter, Bacillus cereus, B. firmus, B. thuringiensis, B. thuringiensis* ssp. *aizawai, B. t.* ssp. *israelensis, B. t.* ssp. *galleriae, B. t.* ssp. *kurstaki, B. t.* ssp. *tenebrionis, Beauveria bassiana, B. brongniartil, Burkholderia* spp., *Chromobacterium subtsugae, Cydia pomonella granulovirus* (CpGV), *Cryptophlebla leucotreta* granulovirus (CrIeGV), *Flavobacterium* sp., *Helicoverpa armigera* nucleopolyhedrovirus (HearNPV), *Helicoverpa zea* nucleopolyhedrovirus (HzNPV), *Helicoverpa zea* single capsid nucleopolyhedrovirus (HzSNPV), *HeterorhabditiS bacteriophora, lsaria fumosorosea, Lecanicillium longisporum, L. muscarium, Metarhizium anisopliae, Metarhizium anisopliae* var. *anisopliae, M. anisopliae* var. *acridum, Nomuraea rileyi, Paecilomyces fumosoroseus, P. lilacinus, Paembacillus popilliae, Pasteuria* spp., *P. nishizawae, P. penetrans, P. ramosa, P. thornea, P. usgae, Pseudomonas fluorescens, Spodoptera littoralis* nucleopolyhedrovirus (SpIiNPV), *Steinernema carpocapsae, S. feltiae, S. kraussei, Streptomyces galbus, S. microflavus,*

L4) Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, (E,Z,Z)-3,8,11-tetradecatrienyl acetate, (Z,E)-9,12-tetradecadien-1-yl acetate, Z-7-tetradecen-2-one, Z-9-tetradecen-1-ylacetate, Z-11-tetradecenal, Z-11-tetradecen-1-ol, extract of *Chenopodium ambrosiodes*, Neem oil, Quillay extract;

L5) Microbial pesticides with plant stress reducing, plant growth regulator, plant growth promoting and/or yield enhancing activity: *Azospirillum amazonense, A. brasltense, A. lipoferum, A. irakense, A. halopraeferens, Bradyrhizobium* spp., *B. elkanii, B. japonicum, B. liaoningense, B. lupini, Delfiia acidovorans, Glomus intraradices, Mesorhizobium* spp., *Rhizobium leguminosarum* bv. *phaseoli, R. l.* bv. *trifolil, R. l.* bv. *viciae, R. tropici, Sinorhizobium meliloti.*

The biopesticides from group L1) and/or L2) may also have insecticidal, acaricidal, molluscidal, pheromone, nematicidal, plant stress reducing, plant growth regulator, plant growth promoting and/or yield enhancing activity. The biopesticides from group L3) and/or L4) may also have fungicidal, bactericidal, viricidal, plant defense activator, plant stress reducing, plant growth regulator, plant growth promoting and/or yield enhancing activity. The biopesticides from group L5) may also have fungicidal, bactericidal, viricidal, plant defense activator, insecticidal, acaricidal, molluscidal, pheromone and/or nematicidal activity.

Many of these biopesticides have been deposited under deposition numbers mentioned herein (the prefices such as ATCC or DSM refer to the acronym of the respective culture collection, for details see e. g. here: http://www.wfcc.info/ccinfo/collection/by_acronym/), are referred to in literature, registered and/or are commercially available: mixtures of *Aureobasidium pullulans* DSM 14940 and DSM 14941 isolated in 1989 in Konstanz, Germany (e. g. blastospores in Blossom Protect® from bio-ferm GmbH, Austria), *Azospirillum brasilense* Sp245 originally isolated in wheat reagion of South Brazil (Passo Fundo) at least prior to 1980 (BR 11005; e. g. GELFIX® Gramineas from BASF Agricultural Specialties Ltd., Brazil), *A. brasilense* strains Ab-V5 and Ab-V6 (e. g. in AzoMax from Novozymes BioAg Produtos papra Agricultura Ltda., Quattro Barras, Brazil or Simbiose-Maiz® from Simbiose-Agro, Brazil; Plant Soil 331, 413-425, 2010), *Bacillus amyloliquefaciens* strain AP-188 (NRRL B-50615 and B-50331; U.S. Pat. No. 8,445,255); *B. amyloliquefaciens* spp. *plantarum* D747 isolated from air in Kikugawa-shi, Japan (US 20130236522 A1; FERM BP-8234; e. g. Double Nickel™ 55 WDG from Certis LLC, USA), *B. amyloliquefaciens* spp. *plantarum* FZB24 isolated from soil in Brandenburg, Germany (also called SB3615; DSM 96-2; J. Plant Dis. Prot. 105, 181-197, 1998; e. g. Taegro® from Novozyme Biologicals, Inc., USA), *B. amyloliquefaciens* ssp. *plantarum* FZB42 isolated from soil in Brandenburg, Germany (DSM 23117; J. Plant Dis. Prot. 105, 181-197, 1998; e. g. RhizoVital® 42 from AbiTEP GmbH, Germany), *B. amyloliquefaciens* ssp. *plantarum* MBI600 isolated from faba bean in Sutton Bonington, Nottinghamshire, U.K. at least before 1988 (also called 1430; NRRL B-50595; US 2012/0149571 A1; e. g. Integral® from BASF Corp., USA), *B. amyloliquefaciens* spp. *plantarum* QST-713 isolated from peach orchard in 1995 in California, U.S.A. (NRRL B-21661; e. g. Serenade® MAX from Bayer Crop Science LP, USA), *B. amyloliquefaciens* spp. *plantarum* TJ1000 isolated in 1992 in South Dakota, U.S.A. (also called 1BE; ATCC BAA-390; CA 2471555 A1; e. g. QuickRoots™ from TJ Technologies, Watertown, S. Dak., USA), *B. firmus* CNCM I-1582, a variant of parental strain EIP-N1 (CNCM I-1556) isolated from soil of central plain area of Israel (WO 2009/126473, U.S. Pat. No. 6,406,690; e. g. Votivo® from Bayer CropScience LP, USA), *B. pumilus* GHA 180 isolated from apple tree rhizosphere in Mexico (IDAC 260707-01; e. g. PRO-MIX® BX from Premier Horticulture, Quebec, Canada), *B. pumilus* INR-7 otherwise referred to as BU-F22 and BU-F33 isolated at least before 1993 from cucumber infested by *Erwinia tracheiphlla* (NRRL B-50185, NRRL B-50153; U.S. Pat. No. 8,445,255), *B. pumilus* KFP9F isolated from the rhizosphere of grasses in South Africa at least before 2008 (NRRL B-50754; WO 2014/029697; e. g. BAC-UP or FUSION-P from BASF Agricultural Specialities (Pty) Ltd., South Africa), *B. pumilus* QST 2808 was isolated from soil collected in Pohnpei, Federated States of Micronesia, in 1998 (NRRL B-30087; e. g. Sonata® or Ballad® Plus from Bayer Crop Science LP, USA), *B. simplex* ABU 288 (NRRL B-50304; U.S. Pat. No. 8,445,255), *B. subtilis* FB17 also called UD 1022 or UD10-22 isolated from red beet roots in North America (ATCC PTA-11857; System. Appl. Microbiol. 27, 372-379, 2004; US 2010/0260735; WO 2011/109395); *B. thuringiensis* sp. *aizawai* ABTS-1857 isolated from soil taken from a lawn in Ephraim, Wis., U.S.A., in 1987 (also called ABG-6346; ATCC SD-1372; e. g. Xen-Tari® from BioFa AG, Munsingen, Germany), B. t. ssp. *kurstaki* ABTS-351 identical to HD-1 isolated in 1967 from diseased Pink Bollworm black larvae in Brownsville, Tex., U.S.A. (ATCC SD-1275; e. g. Dipel® DF from Valent BioSciences, Ill., USA), *B. t.* ssp. *kurstaki* SB4 isolated from *E. saccharin* larval cadavers (NRRL B-50753; e. g. Beta Pro® from BASF Agricultural Specialities (Pty) Ltd., South Africa), *B. t.* ssp. *tenebrionis* NB-176-1, a mutant of strain NB-125, a wild type strain isolated in 1982 from a dead pupa of the beetle *Tenebrio molitor* (DSM 5480; EP 585 215 B1; e. g. Novodor® from Valent BioSciences, Switzerland), *Beauveria bassiana* GHA (ATCC 74250; e. g. BotaniGard® 22WGP from Laverlam Int. Corp., USA), *B. bassiana* JW-1 (ATCC 74040; e. g. Naturalis® from CBC (Europe) S.r.l., Italy), *B. bassiana* PPRI 5339 isolated from the larva of the tortoise beetle *Conchyloctenia punctata* (NRRL 50757; e. g. Broad Band® from BASF Agricultural Specialities (Pty) Ltd., South Africa), *Bradyrhizobium elkanii* strains SEMIA 5019 (also called 29W) isolated in Rio de Janeiro, Brazil and SEMIA 587 isolated in 1967 in the State of Rio Grande do Sul, from an area previously inoculated with a North American isolate, and used in commercial inoculants since 1968 (Appl. Environ. Microbi-Microbiol. 73(8), 2635, 2007; e. g. GELFIX 5 from BASF Agricultural Specialties Ltd., Brazil), *B. japonicum* 532c isolated from Wisconsin field in U.S.A. (Nitragin 61A152; Can. J. Plant. Sci. 70, 661-666, 1990; e. g. in Rhizoflo®, Histick®, Hicoat® Super from BASF Agricultural Specialties Ltd., Canada), *B. japonicum* E-109 variant of strain USDA 138 (INTA E109, SEMIA 5085; Eur. J. Soil Biol. 45, 28-35, 2009; Biol. Fertil. Soils 47, 81-89, 2011); *B. japonicum* strains deposited at SEMIA known from Appl. Environ. Microbiol. 73(8), 2635, 2007: SEMIA 5079 isolated from soil in Cerrados region, Brazil by Embrapa-Cerrados used in commercial inoculants since 1992 (CPAC 15; e. g. GELFIX 5 or ADHERE 60 from BASF Agricultural Specialties Ltd., Brazil), *B. japonicum* SEMIA 5080 obtained under lab conditions by Embrapa-Cerrados in Brazil and used in commercial inoculants since 1992, being a natural variant of SEMIA 586 (CB1809) originally isolated in U.S.A. (CPAC 7; e. g. GELFIX 5 or ADHERE 60 from BASF Agricultural Specialties Ltd., Brazil); *Burkholderia* sp. A396 isolated from soil in Nikko, Japan, in 2008 (NRRL B-50319; WO 2013/032693; Marrone Bio Innovations, Inc., USA), *Coniothyrium minitans* CON/M/91-08 isolated from oilseed rape (WO 1996/021358; DSM 9660; e. g. Contans® WG, Intercept® WG from Bayer CropScience AG, Germany), harpin (alpha-beta) protein (Science 257, 85-88, 1992; e. g. Messenger™ or HARP-N-Tek from Plant Health Care plc, U.K.), *Helicoverpa armigera* nucleopolyhedrovirus (HearNPV) (J. Invertebrate Pathol. 107, 112-126, 2011; e. g. Helicovex® from Adermatt Biocontrol, Switzerland; Diplomata® from Koppert, Brazil; Vivus® Max from AgBiTech Pty Ltd., Queensland, Australia), *Helicoverpa zea* single capsid nucleopolyhedrovirus (HzSNPV) (e. g. Gemstar® from Certis LLC, USA), *Helicoverpa zea* nucleopolyhedrovirus ABANPV-U (e. g. Heligen® from AgBiTech Pty Ltd., Queensland, Australia), *Heterorhabditis* bacteriophora (e. g. Nemasys® G from BASF Agricultural Specialities Limited, UK), Isaria fumosorosea Apopka-97 isolated from mealy bug on gynura in Apopka, Fla., U.S.A. (ATCC 20874; Biocontrol Science Technol. 22(7), 747-761, 2012; e. g. PFR-97™ or PreFeRal® from Certis LLC, USA), *Metarhizium amsopliae* var. *amsopliae* F52 also called 275 or V275 isolated from codling moth in Austria (DSM 3884, ATCC 90448; e. g. Met52® Novozymes Biologicals BioAg Group, Canada), *Metschnikowia fructicola* 277 isolated from grapes in the central part of Israel (U.S. Pat. No. 6,994,849; NRRL Y-30752; e. g. formerly Shemer® from Agrogreen, Israel), *Paecllomyces ilacinus* 251 isolated from infected nematode eggs in the Philippines (AGAL 89/030550; WO1991/02051; Crop Protection 27, 352-361, 2008; e. g. BioAct® from Bayer CropScience AG, Germany and MeloCon® from Certis, USA), *Paembaallus alvei* NAS6G6 isolated from the rhizosphere of grasses in South Africa at least before 2008 (WO 2014/029697; NRRL B-50755; e.g. BAC-UP from BASF Agricultural Specialities (Pty) Ltd., South Africa), *Pasteuria nishizawae* Pn1 isolated from a soybean field in the mid-2000s in Illinois, U.S.A. (ATCC SD-5833; Federal Register 76(22), 5808, Feb. 2, 2011; e.g. Clariva™ PN from Syngenta Crop Protection, LLC, USA), *Penicillium bilaiae* (also called *P. biail*) strains ATCC 18309 (=ATCC 74319), ATCC 20851 and/or ATCC 22348 (=ATCC 74318) originally isolated from soil in Alberta, Canada (Fertilizer Res. 39, 97-103, 1994; Can. J. Plant Sci. 78(1), 91-102, 1998; U.S. Pat. No. 5,026,417, WO 1995/017806; e. g. Jump Start®, Provide® from Novozymes Biologicals BioAg Group, Canada), *Reynoutria sachalinensis* extract (EP 0307510 B1; e. g. Regalia® SC from Marrone BioInnovations, Davis, Calif., USA or Milsana® from BioFa AG, Germany), *Steinemema carpocapsae* (e. g. Millenium® from BASF Agricultural Specialities Limited, UK), *S. feltiae* (e. g. Nemashield® from BioWorks, Inc., USA; Nemasys® from BASF Agricultural Specialities Limited, UK), *Streptomyces microflavus* NRRL B-50550 (WO 2014/124369; Bayer CropScience, Germany), *Trichoderma asperelloides* JM41R isolated in South Africa (NRRL 50759; also referred to as *T. fertile*; e. g. Trichoplus® from BASF Agricultural Specialities (Pty) Ltd., South Africa), *T. harzianum* T-22 also called KRL-AG2 (ATCC 20847; BioControl 57, 687-696, 2012; e. g. Plantshield® from BioWorks Inc., USA or SabrEx™ from Advanced Biological Marketing Inc., Van Wert, Ohio, USA).

According to the invention, the solid material (dry matter) of the biopesticides (with the exception of oils such as Neem oil) are considered as active components (e.g. to be obtained after drying or evaporation of the extraction or suspension medium in case of liquid formulations of the microbial pesticides).

In accordance with the present invention, the weight ratios and percentages used herein for a biological extract such as Quillay extract are based on the total weight of the dry content (solid material) of the respective extract(s).

The total weight ratios of compositions comprising at least one microbial pesticide in the form of viable microbial cells including dormant forms, can be determined using the amount of CFU of the respective microorganism to calclulate the total weight of the respective active component with the following equation that $1\times10^{10}$ CFU equals one gram of total weight of the respective active component. Colony forming unit is measure of viable microbial cells, in particular fungal and bacterial cells. In addition, here "CFU" may also be understood as the number of (juvenile) individual nematodes in case of (entomopathogenic) nematode biopesticides, such as *Steinernema feltiae*.

When mixtures comprising microbial pesticides are employed in crop protection, the application rates preferably range from about $1\times106$ to $5\times1015$ (or more) CFU/ha, preferably from about $1\times108$ to about $1\times1013$ CFU/ha, and even more preferably from about $1\times109$ to about $1\times1012$ CFU/ha. In the case of (entomopathogenic) nematodes as microbial pesticides (e. g. *Steinernema feltiae*), the application rates preferably range inform about $1\times105$ to $1\times1012$ (or more), more preferably from $1\times108$ to $1\times1011$, even more preferably from $5\times108$ to $1\times1010$ individuals (e. g. in the form of eggs, juvenile or any other live stages, preferably in an infetive juvenile stage) per ha.

When mixtures comprising microbial pesticides are employed in seed treatment, the application rates with respect to plant propagation material preferably range from about $1\times106$ to $1\times1012$ (or more) CFU/seed. Preferably, the concentration is about $1\times106$ to about $1\times109$ CFU/seed. In the case of the microbial pesticides II, the application rates with respect to plant propagation material also preferably range from about $1\times107$ to $1\times1014$ (or more) CFU per 100 kg of seed, preferably from $1\times109$ to about $1\times1012$ CFU per 100 kg of seed.

The invention also relates to agrochemical compositions comprising an auxiliary and at least one compound of the present invention or a mixture thereof.

An agrochemical composition comprises a pesticidally effective amount of a compound of the present invention or a mixture thereof. The term "pesticidally effective amount" is defined below.

The compounds of the present invention or the mixtures thereof can be converted into customary types of agrochemical compositions, e. g. solutions, emulsions, suspensions, dusts, powders, pastes, granules, pressings, capsules, and mixtures thereof. Examples for composicomposition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Mono-graph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyhnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxyiates, N-substituted fatty acid amides, amine oxides, esters, sugar-based surfactants, polymeric surfactants, and mixtures thereof. Examples of alkoxyiates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compounds of the present invention on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100% (according to NMR spectrum).

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage de-vice, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e. g. components comprising compounds of the present invention and/or mixing partners as defined above, may be mixed by the user in a spray tank and further auxiliaries and additives may be added, if appropriate.

In a further embodiment, either individual components of the composition according to the invention or partially premixed components, e. g. components comprising compounds of the present invention and/or mixing partners as defined above, can be applied jointly (e.g. after tank mix) or consecutively.

The compounds of the present invention are suitable for use in protecting crops, plants, plant propagation materials, such as seeds, or soil or water, in which the plants are growing, from attack or infestation by animal pests. Therefore, the present invention also relates to a plant protection method, which comprises contacting crops, plants, plant propagation materials, such as seeds, or soil or water, in which the plants are growing, to be protected from attack or infestation by animal pests, with a pesticidally effective amount of a compound of the present invention.

The compounds of the present invention are also suitable for use in combating or controlling animal pests. Therefore, the present invention also relates to a method of combating or controlling animal pests, which comprises contacting the animal pests, their habitat, breeding ground, or food supply, or the crops, plants, plant propagation materials, such as seeds, or soil, or the area, material or environment in which the animal pests are growing or may grow, with a pesticidally effective amount of a compound of the present invention.

The compounds of the present invention are effective through both contact and ingestion. Furthermore, the compounds of the present invention can be applied to any and all developmental stages, such as egg, larva, pupa, and adult.

The compounds of the present invention can be applied as such or in form of compositions comprising them as defined above. Furthermore, the compounds of the present invention can be applied together with a mixing partner as defined above or in form of compositions comprising said mixtures as defined above. The components of said mixture can be applied simultaneously, jointly or separately, or in succession, that is immediately one after another and thereby creating the mixture "in situ" on the desired location, e.g. the plant, the sequence, in the case of separate application, generally not having any effect on the result of the control measures.

The application can be carried out both before and after the infestation of the crops, plants, plant propagation materials, such as seeds, soil, or the area, material or environment by the pests.

Suitable application methods include inter alia soil treatment, seed treatment, in furrow application, and foliar application. Soil treatment methods include drenching the soil, drip irrigation (drip application onto the soil), dipping roots, tubers or bulbs, or soil injection. Seed treatment techniques include seed dressing, seed coating, seed dusting, seed soaking, and seed pelleting. In furrow applications typically include the steps of making a furrow in cultivated land, seeding the furrow with seeds, applying the pesticidally active compound to the furrow, and closing the furrow. Foliar application refers to the application of the pesticidally active compound to plant foliage, e.g. through spray equipment. For foliar applications, it can be advantageous to modify the behavior of the pests by use of pheromones in combination with the compounds of the present invention. Suitable pheromones for specific crops and pests are known to a skilled person and publicly available from databases of pheromones and semiochemicals, such as http://www.pherobase.com.

As used herein, the term "contacting" includes both direct contact (applying the compounds/compositions directly on the animal pest or plant—typically to the foliage, stem or roots of the plant) and indirect contact (applying the compounds/compositions to the locus, i.e. habitat, breeding ground, plant, seed, soil, area, material or environment in which a pest is growing or may grow, of the animal pest or plant).

The term "animal pest" includes arthropods, gastropods, and nematodes. Preferred animal pests according to the invention are arthropods, preferably insects and arachnids, in particular insects. Insects, which are of particular relevance for crops, are typically referred to as crop insect pests.

The term "crop" refers to both, growing and harvested crops.

The term "plant" includes cereals, e.g. durum and other wheat, rye, barley, triticale, oats, rice, or maize (fodder maize and sugar maize/sweet and field corn); beet, e.g. sugar beet or fodder beet; fruits, such as pomes, stone fruits or soft fruits, e.g. apples, pears, plums, peaches, nectarines, almonds, cherries, papayas, strawberries, raspberries, blackberries or gooseberries; leguminous plants, such as beans, lentils, peas, alfalfa or soybeans; oil plants, such as rapeseed (oilseed rape), turnip rape, mustard, olives, sunflowers, coconut, cocoa beans, castor oil plants, oil palms, ground nuts or soybeans; cucurbits, such as squashes, pumpkins, cucumber or melons; fiber plants, such as cotton, flax, hemp or jute; citrus fruit, such as oranges, lemons, grapefruits or mandarins; vegetables, such as eggplant, spinach, lettuce (e.g. iceberg lettuce), chicory, cabbage, asparagus, cabbages, carrots, onions, garlic, leeks, tomatoes, potatoes, cucurbits or sweet peppers; lauraceous plants, such as avocados, cinnamon or camphor; energy and raw material plants, such as corn, soybean, rapeseed, sugar cane or oil palm; tobacco; nuts, e.g. walnuts; pistachios; coffee; tea; bananas; vines (table grapes and grape juice grape vines); hop; sweet leaf (also called Stevia); natural rubber plants or ornamental and forestry plants, such as flowers (e.g. carnation, petunias, geranium/pelargoniums, pansies and impatiens), shrubs, broad-leaved trees (e.g. poplar) or evergreens, e.g. conifers; eucalyptus; turf; lawn; grass such as grass for animal feed or ornamental uses. Preferred plants include potatoes sugar beets, tobacco, wheat, rye, barley, oats, rice, corn, cotton, soybeans, rapeseed, legumes, sunflowers, coffee or sugar cane; fruits; vines; ornamentals; or vegetables, such as cucumbers, tomatoes, beans or squashes.

The term "plant" is to be understood as including wild type plants and plants, which have been modified by either conventional breeding, or mutagenesis or genetic engineering, or by a combination thereof.

Plants, which have been modified by mutagenesis or genetic engineering, and are of particular commercial importance, include alfalfa, rapeseed (e.g. oilseed rape), bean, carnation, chicory, cotton, eggplant, eucalyptus, flax, lentil, maize, melon, papaya, petunia, plum, poplar, potato, rice, soybean, squash, sugar beet, sugarcane, sunflower, sweet pepper, tobacco, tomato, and cereals (e.g. wheat), in particular maize, soybean, cotton, wheat, and rice. In plants, which have been modified by mutagenesis or genetic engineering, one or more genes have been mutagenized or integrated into the genetic material of the plant. The one or more mutagenized or integrated genes are preferably selected from pat, epsps, cry1Ab, bar, cry1Fa2, cry1Ac, cry34Ab1, cry35AB1, cry3A, cryF, cry1F, mcry3a, cry2Ab2, cry3Bb1, cry1A.105, dfr, barnase, vip3Aa20, barstar, als, bxn, bp40, asn1, and ppo5. The mutagenesis or integration of the one or more genes is performed in order to improve certain properties of the plant. Such properties, also known as traits, include abiotic stress tolerance, altered growth/yield, disease resistance, herbicide tolerance, insect resistance, modified product quality, and pollination control. Of these properties, herbicide tolerance, e.g. imidazolinone tolerance, glyphosate tolerance, or glufosinate tolerance, is of particular importance. Several plants have been rendered tolerant to herbicides by mutagenesis, for example Clearfield® oilseed rape being tolerant to imidazolinones, e.g. imazamox. Alternatively, genetic engineering methods have been used to render plants, such as soybean, cotton, corn, beets and oil seed rape, tolerant to herbicides, such as glyphosate and glufosinate, some of which are commercially available under the trade names RoundupReady® (glyphosate) and LibertyLink® (glufosinate). Furthermore, insect resistance is of importance, in particular lepidopteran insect resistance and coleopteran insect resistance. Insect resistance is typically achieved by modifying plants by integrating cry and/or vip genes, which were isolated from *Bacillus thuringiensis* (Bt), and code for the respective Bt toxins. Genetically modified plants with insect resistance are commercially available under trade names including Wide- Strike®, Bollgard®, Agrisure®, Herculex®, YieldGard®, Genuity®, and Intacta®. Plants may be modified by mutagenesis or genetic engineering either in terms of one property (singular traits) or in terms of a combination of properties (stacked traits). Stacked traits, e.g. the combination of herbicide tolerance and insect resistance, are of increasing importance. In general, all relevant modified plants in connection with singular or stacked traits as well as detailed information as to the mutagenized or integrated genes and the respective events are available from websites of the organizations "International Service for the Acquisition of Agri-biotech Applications (ISAAA)" (http://www.isaaa.org/gmapprovaldatabase) and "Center for Environmental Risk Assessment (CERA)" (http://cera-gmc.org/GMCropDatabase).

It has surprisingly been found that the pesticidal activity of the compounds of the present invention may be enhanced by the insecticidal trait of a modified plant. Furthermore, it has been found that the compounds of the present invention are suitable for preventing insects to become resistant to the insecticidal trait or for combating pests, which already have become resistant to the insecticidal trait of a modified plant. Moreover, the compounds of the present invention are suitable for combating pests, against which the insecticidal trait is not effective, so that a complementary insecticidal activity can advantageously be used.

The term "plant propagation material" refers to all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "seed" embraces seeds and plant propagules of all kinds including but not limited to true seeds, seed pieces, suckers, corms, bulbs, fruit, tubers, grains, cuttings, cut shoots and the like, and means in a preferred embodiment true seeds.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment, in furrow application or of application to the pests dwelling place or nest, the quantity of active ingredient ranges from 0.0001 to 500 g per 100 m², preferably from 0.001 to 20 g per 100 m².

For use in treating crop plants, e.g. by foliar application, the rate of application of the active ingredients of this invention may be in the range of 0.0001 g to 4000 g per hectare, e.g. from 1 g to 2 kg per hectare or from 1 g to 750 g per hectare, desirably from 1 g to 100 g per hectare, more desirably from 10 g to 50 g per hectare, e.g., 10 to 20 g per hectare, 20 to 30 g per hectare, 30 to 40 g per hectare, or 40 to 50 g per hectare.

The compounds of the present invention are particularly suitable for use in the treatment of seeds in order to protect the seeds from insect pests, in particular from soil-living insect pests, and the resulting seedling's roots and shoots against soil pests and foliar insects. The present invention therefore also relates to a method for the protection of seeds from insects, in particular from soil insects, and of the seedling's roots and shoots from insects, in particular from soil and foliar insects, said method comprising treating the seeds before sowing and/or after pregermination with a compound of the present invention. The protection of the seedling's roots and shoots is preferred. More preferred is the protection of seedling's shoots from piercing and sucking insects, chewing insects and nematodes.

The term "seed treatment" comprises all suitable seed treatment techniques known in the art, such as seed dressing, seed coating, seed dusting, seed soaking, seed pelleting, and in-furrow application methods. Preferably, the seed treatment application of the active compound is carried out by spraying or by dusting the seeds before sowing of the plants and before emergence of the plants.

The present invention also comprises seeds coated with or containing the active compound. The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is for example seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, Brassica species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment of seeds from plants, which have been modified by mutagenisis or genetic engineering, and which e.g. tolerate the action of herbicides or fungicides or insecticides. Such modified plants have been described in detail above.

Conventional seed treatment formulations include for example flowable concentrates FS, solutions LS, suspoemulsions (SE), powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter. Preferably, the formulations are applied such that germination is not included.

The active substance concentrations in ready-to-use formulations, which may be obtained after two-to-tenfold dilution, are preferably from 0.01 to 60% by weight, more preferably from 0.1 to 40% by weight.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of the compounds of the present invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

In the treatment of seed, the application rates of the compounds of the invention are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed, e.g. from 1 g to 100 g or from 5 g to 100 g per 100 kg of seed.

The invention therefore also relates to seed comprising a compound of the present invention, or an agriculturally useful salt thereof, as defined herein. The amount of the compound of the present invention or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

The compounds of the present invention may also be used for improving the health of a plant. Therefore, the present invention also relates to a method for improving plant health by treating a plant, plant propagation material and/or the locus where the plant is growing or is to grow with an effective and non-phytotoxic amount of a compound of the present invention.

As used herein "an effective and non-phytotoxic amount" means that the compound is used in a quantity which allows to obtain the desired effect but which does not give rise to any phytotoxic symptom on the treated plant or on the plant grown from the treated propagule or treated soil.

The terms "plant" and "plant propagation material" are defined above.

"Plant health" is defined as a condition of the plant and/or its products which is determined by several aspects alone or in combination with each other such as yield (for example increased biomass and/or increased content of valuable ingredients), quality (for example improved content or composition of certain ingredients or shelf life), plant vigour (for example improved plant growth and/or greener leaves ("greening effect"), tolerance to abiotic (for example drought) and/or biotic stress (for example disease) and production efficiency (for example, harvesting efficiency, processability).

The above identified indicators for the health condition of a plant may be interdependent and may result from each other. Each indicator is defined in the art and can be determined by methods known to a skilled person.

The compounds of the invention are also suitable for use against non-crop insect pests. For use against said non-crop pests, compounds of the present invention can be used as bait composition, gel, general insect spray, aerosol, as ultra-low volume application and bed net (impregnated or surface applied). Furthermore, drenching and rodding methods can be used.

As used herein, the term "non-crop insect pest" refers to pests, which are particularly relevant for non-crop targets, such as ants, termites, wasps, flies, ticks, mosquitos, crickets, or cockroaches.

The bait can be a liquid, a solid or a semisolid preparation (e.g. a gel). The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature (e.g. http://www.pherobase.com), and are known to those skilled in the art.

For use in bait compositions, the typical content of active ingredient is from 0.001 weight % to 15 weight %, desirably from 0.001 weight % to 5% weight % of active compound.

Formulations of the compounds of the present invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents, furthermore auxiliaries such as emulsifiers, perfume oils, if appropriate stabilizers, and, if required, propellants.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of the present invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the present invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder.

The compounds of the present invention and its compositions can be used for protecting wooden materials such as trees, board fences, sleepers, frames, artistic artifacts, etc. and buildings, but also construction materials, furniture, leathers, fibers, vinyl articles, electric wires and cables etc. from ants and/or termites, and for controlling ants and termites from doing harm to crops or human being (e.g. when the pests invade into houses and public facilities).

Customary application rates in the protection of materials are, for example, from 0.001 g to 2000 g or from 0.01 g to 1000 g of active compound per $m^2$ treated material, desirably from 0.1 g to 50 g per $m^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

The compounds of the the present invention are especially suitable for efficiently combating animal pests such as arthropods, gastropods and nematodes including but not limited to: insects from the order of Lepidoptera, for example *Achroia grisella, Acleris* spp. such as *A. fimbriana, A. gloverana, A. variana; acrolepiopsis assectella, Acronicta major, Adoxophyes* spp. such as *A. cyrtosema, A. orana; Aedia leucomelas, Agrotis* spp. such as *A. exclamationis, A. fucosa, A. ipsllon, A. orthogoma, A. segetum, A. subterranea; Alabama argillacea, Aleurodicus dispersus, Alsophlla pometaria, Ampelophaga rubiginosa, Amyelois transitella, Anacampsis sarcitella, Anagasta kuehniella, Anarsia lineatella, Anisota senatoria, Antheraea pernyi, Anticarsia (=Thermesia)* spp. such as *A. gemmatalis; Apamea* spp., *Aproaerema modicella, Archips* spp. such as *A. argyrospila, A. fuscocupreanus, A. rosana, A. xyloseanus; Argyresthia conjugella, Argyroploce* spp., *Argyrotaenia* spp. such as *A. velutinana; Athetis mindara, Austroasca ridigrisea, Autographa gamma, Autographa nigrisigna, Barathra brassicae, Bedellia* spp., *Bonagota salubricola, Borbo cinnara, Bucculatrix thurberiella, Bupalus piniarius, Busseola* spp., *Cacoecia* spp. such as *C. murinana, C. podana; Cactoblastis cactorum, Cadra cautella, Calingo braziliensis, Caloptiltis theivora, Capua reticulana, Carposina* spp. such as *C. niponensis, C. sasakii; Cephus* spp., *Chaetocnema aridula, Cheimatobia brumata, Chilo* spp. such as *C. lndicus C. suppressalis, C. partellus; Choreutis pariana, Choristoneura* spp. such as *C. conflictana, C. fumiferana, C. longicellana, C. murinana, C. occidentalis, C. rosaceum; Chlysodeixis (=Pseudoplusia)* spp. such as *C. eriosoma, C. includens; Cirphis unipuncta, Ciysia ambiguella, Cnaphalocerus* spp., *Cnaphalocrocis medinalis, Cnephasia* spp., *Cochylis hospes, Coieophora* spp., *Colias eurytheme, Conopomorpha* spp., *Conotrachelus* spp., *Copitarsia* spp., *Corcyra cephalonica, Crambus caliginosellus, Crambus teterrellus, Crocidosema (=Epinotia) aporema, Cydalima (=Diaphania) perspectalis, Cydia (=Carpocapsa)* spp. such as *C. pomonella, C. latiferreana; Dalaca noctuides, Datanaintegerrima, Dasychira pinicola, Dendrolimus* spp. such as *D. pini, D. spectabilis, D. sIbiricus; Desmia funeralis, Diaphania* spp. such as *D. nitidalis, D. hyalinata; Diatraea grandiosella, Diatraea saccharalis, Diphthera festiva, Earias* spp. such as *E. insulana, E. vittella; Ecdytolopha aurantianu, Egira (=Xylomyges) Elasmopalpus sellus, Eldana saccharina, Endopiza viteana, Ennomos subsignaria, Eoreuma loftini, Ephestia* spp. such as *E. cautella, E. elutella, E. kuehniella; Epinotia aporema, Epiphyas postvittana, Erannis tiliaria, Erionota thrax, Etiella* spp., *Eulia* spp., *Eupoecilia ambiguella, Euproctis chrysorrhoea, Euxoa* spp., *Evetria bouliana, Faronta Feltia* spp. such as *F. subterranean; Galleria mellonella, Gracillaria* spp., *Grapholita* spp. such as *G. funebrana, G. molesta, G. inopinata; Halysidota* spp., *Harrisina americana, Hedyiepta* spp., *Helicoverpa* spp. such as *H. armigera (=Heliothis armigera), H. zea (=Heliothis zea); Heliothis* spp. such as *H. assulta, H. subflexa, H. virescens; Hellula* spp. such as *H. undalis, H. rogatalis; Helocoverpa gelotopoeon, Hemlleuca Herpetogramma licarsisalis, Hibernia defoliaria, Hofmannophila pseudospretella, Homoeosoma electellum, Homona magnanima, Hypena scabra, Hyphantria cunea, Hyponomeuta padella, Hyponomeuta Kakivoria flavofasciata, Keiferia lycopersicella, Lambdina fiscellaria fiscellaria, Lambdina fiscellaria lugubrosa, Lamprosemaindicata, Laspeyresia molesta, L eguminivora glycinivorella, L erodea eufala, L eucinodes orbonalis, L eucoma salicis, Leucoptera* spp. such as *L. coffeella, L. scitella; Leuminivora lycinivorella, LithocollenS blancardella, Lithophane antennata, Llattia octo (=Amyna axis), Lobesia botrana, Lophocampa* spp., *Loxagrotis albicosta, Loxostege* spp. such as *L. sticticalis, L. cereralis; Lymantria* spp. such as *L. dispar, L. monacha; Lyonetia clerkella, Lyonetia prunifoliella, Malacosoma* spp. such as *M. americanum, M. californicum, M. constrictum, M. neustria; Mamestra* spp. such as *M. brassicae, M. configurata; Mamstra brassicae, Manduca* spp. such as *M. quinquemaculata, M. sexta; Marasmia* spp, *Marmara* spp., *Maruca testulalis, Megalopyge Janata, Melanchra picta, Melaninis ieda, Mocis* spp. such as *M. lapites, M. repanda; Mocis latipes, Monochroa fragariae, Mythimna separata, Nemapogon cloacella, Neoieucinodes elegantalis, Nepytia* spp., *Nymphula* spp., *Oiketicus* spp., *Omiodesindicata, Omphisa anastomosalis, Operophtera brumata, Orgyia pseudotsugata, Oria* spp., *Orthaga thyrisalis, Ostrinia* spp. such as *O. nubilalis; Oulema oryzae, Paleacrita vernata, Panoils flammea, Parnara* spp., *Papaipema nebris, Papilio cresphontes, Paramyelois transitella, Paranthrene regalis, Paysandisia archon, Pectinophora* spp. such as *P. gossypiella; Peridroma saucia, Perileucoptera* spp., such as *P. coffeella; Phalera bucephala, Phryganidia californica, Phthorimaea* spp. such as *P. operculella; Phyllocnistis citrella, Phyllonorycter* spp. such as *P. blancardella, P. crataegella, P. issikil P. ringoniella; Pieris* spp. such as *P. brassicae, P. rapae, P. napi; Pilocrocis tripunctata, Plathypena scabra, Platynota* spp. such as *P. flavedana, P. idaeusalis, P. stultana; Platyptilia carduidactyla, Plebejus argus, Plodiainterpunctella, Plusia* spp, *Plutella maculipennis, Plutella xylostella, Pontia protodica, Prays* spp., *Prodenia* spp., *Proxenus lepigone, Pseudaletia* spp. such as *P. sequax, P. unipuncta; Pyrausta nubilalis, Rachiplusia nu, Richia albicosta, Rhizobius ventrals, Rhyacionia frustrana, Sabulodes aegrotata, Schizura concinna, Schoenobius* spp., *Schreckensteinia festaliella, Scirpophaga* spp. such as *S. incertulas, S. innotata; Scotia segetum, Sesamia* spp. such as *S. inferens, Seudyra subflava, Sitotroga cerealella, Sparganothis pilleriana, Spilonota lechriaspis, S. ocellana, Spodoptera (=Lamphygma)* spp. such as *S. eridania, S. exigua, S. frugiperda, S. latisfascia, S. littoralis, S. litura, S. omithogalli; Stigmella* spp., *Stomopteryx subsecivella, Strymon bazochil Sylepta derogata, Synanthedon* spp. such as *S. exitiosa, Tecia solanivora, Telehin licus, Thaumatopoea pityocampa, Thaumatotibia (=Cryptophlebia) leucotreta, Thaumetopoea pityocampa, Thecla* spp., *Theresimima ampelophaga, Thyrinteina* spp, *Tildeniainconspicuella, Tinea* spp. such as *T. cloacella, T. pellionella; Tineola bisselliella, Tortrix* spp. such as *T. viridana; Trichophaga tapetzella, Trichoplusia* spp. such as *T. ni; Tuta (=Scrobipalpula) absoluta, Udea* spp. such as *U. rubigalis, U. rubigalls; Virachola* spp., *Yponomeuta padella,* and *Zeiraphera canadensis;* insects from the order of Coleoptera, for example *Acalymma vittatum, Acanthoscehdes obtectus, Adoretus* spp., *Agelastica alni, Agrilus* spp. such as *A. anxius, A. planipennis, A. sinuatus; Agriotes* spp. such as *A. fuscicollis, A. lineatus, A. obscurus; Alphitobius diaperinus, Amphimallus solstitialis, Anisandrus dispar, Anisoplia austriaca, Anobium punctatum, Anomala corpulenta, Anomala rufocuprea, Anoplophora* spp. such as *A. glabripennis; Anthonomus* spp. such as *A. eugenh, A. grandis, A. pomorum; Anthrenus* spp., *Aphthona euphoridae, Apion* spp., *Apogonia* spp., *Athous haemorrhoidalis, Atomaria* spp. such as *A. linearis; Attagenus* spp., *Aulacophora femoralis, Blastophagus piniperda, Blitophaga undata, Bruchidius obtectus, Bruchus* spp. such as *B. lentis, B. pisorum, B. rufimanus; Byctiscus betulae, Callidiellum rufipenne, Callopistria floridensis, Callosobruchus chinensis, Cameraria ohridella, Cassida*

*nebulosa, Cerotoma trifurcata, Cetonia aurata, Ceuthorhynchus* spp. such as *C. assimilis, C. napi; Chaetocnema tibialis, Cleonus mendicus, Conoderus* spp. such as *C. vespertinus; Conotrachelus nenuphar, Cosmopolites* spp., *Costelytra zealandica, Crioceris asparagi, Cryptolestes ferrugineus, Cryptorhynchus lapathl, Ctenicera* spp. such as *C. destructor; Curculio* spp., *Cylindrocopturus* spp., *Cyclocephala* spp., *Dactylispa balyi, Dectes texanus, Dermestes* spp., *Diabrotica* spp. such as *D. undecimpunctata, D. speciosa, D. longicornis, D. semipunctata, D. virgifera; Diaprepes abbreviates, Dichocrocis* spp., *Dicladispa armigera, Diloboderus abderus, Diocalandra frumenti (Diocalandra stigmaticollis), Enaphalodes rufulus, Epilachna* spp. such as *E. varivestis, E. vigintioctomaculata; Epitrix* spp. such as *E. hirtipennis, E. simllaris; Eutheola humilis, Eutinobothrus braslliensis, Faustinus cubae, Gibbium psylloides, Gnathocerus cornutus, Hellula undalis, Heteronychus arator, Hylamorpha elegans, Hylobius abietis, Hylotrupes bajulus, Hypera* spp. such as *H. brunneipennis, H. postica; Hypomeces squamosus, Hypothenemus* spp., *lps typographus, Lachnosterna consanguinea, Lasioderma serricome, Latheticus oryzae, Lathridius* spp., *Lema* spp. such as *L. bilineata, L. melanopus; Leptinotarsa* spp. such as *L. decemlineata; Leptispa pygmaea, Limonius californicus, Lissorhoptrus oryzophiius, Lixus* spp., *Luperodes* spp., *Lyctus* spp. such as *L. bruneus; Liogenys fuscus, Macrodactylus* spp. such as *M. subspinosus; Maladera matrida, Megaplatypus mutates, Megascelis* spp., *Melanotus communis, Meligethes* spp. such as *M. aeneus; Melolontha* spp. such as *M. hippocastam, M. melolontha; Metamasius hemipterus, Microtheca* spp., *Migdolus* spp. such as *M. fryanus, Monochamus* spp. such as *M. alternatus; Naupactus xanthographus, Niptus hololeucus, Oberia brevis, Demon hirta, Oryctes rhinoceros, Oryzaephllus surinamensis, Oryzaphagus oryzae, Otiorrhynchus sulcatus, Otiorrhynchus ovatus, Otiorrhynchus sulcatus, Oulema melanopus, Oulema oryzae, Oxycetonia jucunda, Phaedon* spp. such as *P. brassicae, P. cochieariae; Phoracantha recurva, Phyllobius pyri Phyllopertha horticola, Phyllophaga* spp. such as *P. helleri; Phyllotreta* spp. such as *P. chrysocephala, P. nemorum, P. striolata, P. vittula; Phyllopertha horticola, Popillia japonica, Premnotrypes* spp., *Psacothea Maris, Psylliodes chrysocephala, Prostephanus truncates, Psylliodes* spp., *Ptinus* spp., *Pulga saltona, Rhizopertha dominica, Rhynchophorus* spp. such as *R. billineatus, R. ferrugineus, R. palmarum, R. phoenicis, R. vulneratus; Saperda candida, Scolytus schevyrewi, Scyphophorus acupunctatus, Sitona lineatus, Sitophllus* spp. such as *S. granaria, S. oryzae, S. zeamais; Sphenophorus* spp. such as *S. Levis; Stegobium paniceum, Sternechus* spp. such as *S. subsignatus; Strophomorphus ctenotus, Symphyietes* spp., *Tanymecus* spp., *Tenebrio molitor, Tenebrioides mauretanicus, Tribolium* spp. such as *T. castaneum; Trogoderma* spp., *Tychius* spp., *Xylotrechus* spp. such as *X. pyrrhoderus*; and, *Zabrus* spp. such as *Z. tenebrioides*;

insects from the order of Diptera for example *Aedes* spp. such as *A. aegypti, A. albopictus, A. vexans; Anastrepha ludens, Anopheles* spp. such as *A. albimanus, A. crucians, A. freeborni, A. gambiae, A. leucosphyrus, A. maculipennis, A. minimus, A. quadrimaculatus, A. sinensis; Bactrocera invadens, Bibio hortulanus, Calliphora eoithrocephala, Calliphora vicina, Ceratitis capitata, Chrysomyia* spp. such as *C. bezziana, C. hominivorax, C. macellaria; Chrysops atlanticus, Chrysops Chrysops silacea, Cochliomyia* spp. such as *C. hominivorax; Contarinia* spp. such as *C. sorghicola; Cordylobia anthropophaga, Culex* spp. such as *C. nigripalpus, C. pipiens, C. quinquefasciatus, C. tarsalis, C. tritaeniorhynchus; Culicoides furens, Culiseta inornata, Culiseta melanura, Cuterebra* spp., *Dacus cucurbitae, Dacus oleae, Dasineura brassicae, Dasineura oxycoccana, Della* spp. such as *D. antique, D. coarctata, D. platura, D. radicum; Dermatobia hominis, Drosophila* spp. such as *D. suzukii Fannia* spp. such as *F. canicularis; Gastraphllus* spp. such as *G. intestinalis; Geomyza tipunctata, Glossina* spp. such as *G. fuscipes, G. morsitans, G. palpalis, G. tachinoides; Haematobia irritans, Haplodiplosis equestris, Hippelates* spp., *Hylemyia* spp. such as *H. platura; Hypoderma* spp. such as *H. lineata; Hyppobosca* spp., *Hydrellia philippina, Leptoconops torrens, Liriomyza* spp. such as *L. sativae, L. trifolii; Lucllia* spp. such as *L. caprin, L. cuprina, L. sericata; Lycoria pectoralis, Mansonia titilianus, Mayetiola* spp. such as *M. destructor; Musca* spp. such as *M. autumnalis, M. domestica; Muscina stabulans, Oestrus* spp. such as *O. ovis; Opomyza florum, Oscinella* spp. such as *O. frit; Orseolia oryzae, Pegomya hysocyami, Phlebotomus argentipes, Phorbia* spp. such as *P. antiqua, P. brassicae, P. coarctata; Phytomyza gymnostoma, Prosimulium mixtum, Psila rosae, Psorophora columbiae, Psorophora discolor, Rhagoletis* spp. such as *R. cerasi, R. cingulate, R. indifferens, R. mendax, R. pomonella; Rivellia quadrifasciata, Sarcophaga* spp. such as *S. haemorrhoidalis; Simulium vittatum, Sitodiplosis mosellana, Stomoxys* spp. such as *S. calcitrans; Tabanus* spp. such as *T. atratus, T. bovinus, T. lineola, T. similis; Tannia* spp., *Thecodiplosis japonensis, Tipula oleracea, Tipula paludosa*, and *Wohlfahrtia* spp;

insects from the order of *Thysanoptera* for example, *Baliothrips biformis, Dichromothrips corbetti, Dichromothrips* ssp., *Echinothrips americanus, Enneothrips flavens, Frankliniella* spp. such as *F. fusca, F. occidentalis, F. tritici; Heliothnps* spp., *Hercinothrips femoralis, Kakothrips* spp., *Microcephalothrips abdominalis, Neohydatothnps samayunkur, Pezothrips kellyanus, Rhipiphorothrips cruentatus, Scirtothrips* spp. such as *S. citri, S. dorsalis, S. perseae; Stenchaetothrips* spp, *Taeniothrips cardamom, Taeniothrips inconsequens, Thrips* spp. such as *T. imagines, T. hawaiiensis, T. oryzae, T. palmi, T. parvispinus, T. tabaci;* insects from the order of Hemiptera for example, *Acizzia jamatonica, Acrosternum* spp. such as *A. Mare; Acyrthosipon* spp. such as *A. onobrychis, A. pisum; Adelges laricis, Adelges tsugae, Adelphocoris* spp., such as *A. rapidus, A. superbus; Aeneolamia* spp., *Agonoscena* spp., *Aulacorthum solani, Aleurocanthus woglumi, Aleurodes* spp., *Aleurodicus disperses, Aleurolobus barodensis, Aleurothrixus* spp., *Amrasca* spp., *Anasa tristis, Antestiopsis* spp., *Anuraphis cardui, Aonidiella* spp., *Aphanostigma pin, Aphidula nasturtil, Aphis* spp. such as *A. craccivora, A. fabae, A. forbesi, A. gossypii, A. grossulariae, A. maidiradicis, A. pony, A. sambuci, A. schneideri, A. spiraecola; Arboridia apicalis, Arilus critatus, Aspidiella* spp., *Aspidiotus* spp., *Atanus* spp., *Aulacaspis yasumatsui, Aulacorthum solani, Bactericera cockerelli (Paratrioza cockerelli), Bemisia* spp. such as *B. argentifolil, B. tabaci (Aleurodes tabaci); Blissus* spp. such as *B. leucopterus; Brachycaudus* spp. such as *B. cardui, B. helichlysi, B. persicae, B. prunicola; Brachycolus* spp., *Brachycorynella asparagi, Brevicoryne brassicae, Cacopsylla* spp. such as *C. fulguralis, C. pyricola (Psylla piri); Calligypona marginata, Caloconis* spp., *Campylomma livida, Capitophorus horni, Cameocephala fulgida, Caverius* spp., *Ceraplastes* spp., *Ceratovacuna lanigera, Ceroplastes ceriferus, Cerosipha gossypil, Chaetosiphon fragaefolil, Chionaspis tegalensis, Chlorita onukii, Chromaphis juglandicola, Chlysomphalus ficus, Cicadulina mblla, Cimex* spp. such as *C. hemipterus, C. lectularius; Coccomytilus Coccus* spp. such as *C. hesperidum, C. pseudomag-* noliarum; Corythucha arcuata, Creontiades Cryptomyzus ribis, Chlysomphalus aonidum, Cryptomyzus ribis, Ctenarytaina spatulata, Cyrtopeltis notatus, Dalbulus spp., Dasynus piperis, Dialeurodes spp. such as D. citrifolis; Dalbulus maidis, Diaphorina spp. such as D. citri; Diaspis spp. such as D. bromeliae; Dichelops furcatus, Diconocoris hewetti, Doralls spp., Dreyfusia nordmannianae, Dreyfusia piceae, Drosicha spp., Dysaphic spp. such as D. plantaginea, D. gyri, D. radlcola; Dysaulacorthum pseudosolani, Dysdercus spp. such as D. cingulatus, D. intermedius; Dysmicoccus spp., Edessa spp., Geocoris spp., Empoasca spp. such as E. fabae, E. solana; Epidiaspis leperii, Eriosoma spp. such as E. lanigerum, E. pyricola; Erythroneura spp., Eurygaster spp. such as E. integriceps; Euscells bllobatus, Euschistus spp. such as E. heros, E. impictiventris, E. servus; Fiorinia theae, Geococcus coffeae, Glycaspis brimblecombel, Halyomorpha spp. such as H. halys; Heliopeltis spp., Homalodisca vitripennis (=H. coagulata), Horcias nobilellus, Hyalopterus pruni, Hyperomyzus lactucae, Icelya spp. such as I. purchase; Idiocerus spp., Idioscopus spp., Laodelphax striatellus, Lecaniurn spp., Lecanoideus floccissimus, Lepidosaphes spp. such as L. ulmi; Leptocorisa spp., Leptoglossus phyllopus, Lipaphis erysimi, Lygus spp. such as L. hesperus, L. lineolaris, L. pratensis; Maconellicoccus hirsutus, Marchalina hellenica, Macropes excavatus, Macrosiphum spp. such as M. rosae, M. avenae, M. euphorbiae; Macrosteles quadrilineatus, Mahanarva fimbriolata, Megacopta cribraria, Megoura viciae, Melanaphis pyrarius, Melanaphis sacchari, Melanocallis (=Tinocallis) coyaefoliae, Metcafiella spp., Metopolophium dirhodum, Monellia costalis, Monelliopsis pecans, Myzocallis coryli, Murgantia spp., Myzus spp. such as M. ascalonicus, M. cerasi, M. nicotianae, M. persicae, M. varians; Nasonovia ribis-nigri, Neotoxoptera formosana, Neomegalotomus spp, Nephotettix spp. such as N. malayanus, N. nigropictus, N. parvus, N. virescens; Nezara spp. such as N. viridula; Nilaparvata lugens, Nysius huttoni, Oebalus spp. such as O. pugnax; Oncometopia spp., Orthezia praelonga, Oxycaraenus hyalinipennis, Parabemisia myricae, Parlatoria spp., Parthenolecanium spp. such as P. corm, P. persicae; Pemphigus spp. such as P. bursarius, P. populivenae; Peregrinus maidis, Perkinsiella saccharicida, Phenacoccus spp. such as P. aceris, P. gossypil; Phloeomyzus passerinii, Phorodon humuli, Phylloxera spp. such as P. devastatrix, Piesma quadrata, Piezodorus spp. such as P. guildinii; Pinnaspis aspidistrae, Planococcus spp. such as P. citri, P. ficus; Prosapia bicincta, Protopulvinaria pyriformis, Psallus seriatus, Pseudacysta persea, Pseudaulacaspis pentagon, Pseudococcus spp. such as P. comstocki; Psylla spp. such as P. mali; Pteromalus spp., Pulvinaria amygdali, Pyrilla spp., Quadraspidiotus spp., such as Q. perniciosus; Quesada gigas, Rastrococcus spp., Reduvius senilis, Rhizoecus americanus, Rhodnius spp., Rhopalomyzus ascalonicus, Rhopalosiphum spp. such as R. pseudobrassicas, R. insertum, R. maidis, R. padi; Sagalodes spp., Sahlbergella singularis, Saissetia spp., Sappaphis mala, Sappaphis mali, Scaptocoris spp., Scaphoides titanus, Schizaphis graminum, Schizoneura lanuginosa, Scotinophora spp., Selenaspidus articulatus, Sitobion avenae, Sogata spp., Sogatella furcifera, Solubea insularis, Spississtilus festinus (=Stictocephala festina), Stephanitis nashi, Stephanitis pyrioides, Stephanitis takeyai, Tenalaphara malayensis, Tetraleurodes perseae, Therioaphis maculate, Thyanta spp. such as T. accerra, T. perditor; Tibraca spp., Tomaspis spp., Toxoptera spp. such as T. aurantil; Trialeurodes spp. such as T. abutilonea, T. ricin, T. vaporariorum; Triatoma spp., Trioza spp., Typhlocyba spp., Unaspis spp. such as U. citri, U. yanonensis; and Viteus vitifolil, Insects from the order Hymenoptera for example Acanthomyops interjectus, Athalia rosae, Atta spp. such as A. capiguara, A. cephalotes, A. cephalotes, A. laevigata, A. robusta, A. sexdens, A. texana, Bombus spp., Brachymyrmex spp., Camponotus spp. such as C. floridanus, C. pennsylvanicus, C. modoc; Cardiocondyla nuda, Chalibion sp, Crematogaster spp., Dasymutllla occidentalis, Diprion spp., Dolichovespula maculata, Dorymyrmex spp., Dryocosmus kuriphilus, Formica spp., Hoplocampa spp. such as H. minuta, H. testudinea; Iridomyrmex humilis, Lasius spp. such as L. niger, Linepithema humile, Liometopum spp., Leptocybe invasa, Monomorium spp. such as M. pharaonis, Monomorium, Nylandria fulva, Pachycondyla chinensis, Paratrechina longicornis, Paravespula spp., such as P. germanica, P. pennsylvanica, P. vulgaris; Pheidole spp. such as P. megacephala; Pogonomyrmex spp. such as P. barbatus, P. californicus, Pollstes rubiginosa, Prenolepis impairs, Pseudomyrmex gracilis, Schelipron spp., Sirex cyaneus, Solenopsis spp. such as S. geminata, Sinvicta, S. molesta, S. richten, S. xylom, Sphecius speciosus, Sphex spp., Tapinoma spp. such as T. melanocephalum, T. sessile; Tetramorium spp. such as T. caespitum, T. bicarinatum, Vespa spp. such as V. crabro; Vespula spp. such as V. squamosal; Wasmannia auropunctata, Xylocopa sp;

Insects from the order Orthoptera for example Acheta domesticus, Calliptamus italicus, Chortoicetes terminifera, Ceuthophilus spp., Diastrammena asynamora, Dociostaurus maroccanus, Gryllotalpa spp. such as G. africana, G. gryllotalpa; Gryllus spp., Hieroglyphus daganensis, Kraussaria angulifera, Locusta spp. such as L. migratoria, L. pardalina; Melanoplus spp. such as M. bivittatus, M. femurrubrum, M. mexicanus, M. sanguinipes, M. spretus; Nomadacris septemfasciata, Oedaleus senegalensis, Scapteriscus spp., Schistocerca spp. such as S. Americana, S. gregaria, Stemopelmatus spp., Tachycines asynamorus, and Zonozerus variegatus;

Pests from the Class Arachnida for example Acari, e.g. of the families Argasidae, Ixodidae and Sarcoptidae, such as Amblyomma spp. (e.g. A. americanum, A. variegatum, A. maculatum), Argas spp. such as A. persicu), Boophilus spp. such as B. annulatus, B. decoloratus, B. microplus, Dermacentor spp. such as D. silvarum, D. andersom, D. variabilis, Hyalomma spp. such as H. truncatum, Ixodes spp. such as I. ricinus, I. rubicundus, I. scapularis, I. holocyclus, I. pacificus, Rhipicephalus sanguineus, Ornithodorus spp. such as O. moubata, O. hermsi, O. turicata, Ornithonyssus bacoti, Otobius megnim, Dermanyssus gallinae, Psoroptes spp. such as P. ovis, Rhipicephalus spp. such as R. sanguineus, R. appendiculatus, Rhipicephalus evertsi, Rhizoglyphus spp., Sarcoptes spp. such as S. Scabiei; and Family Eriophyidae including Aceria spp. such as A. sheldoni, A. anthocoptes, Acallitus spp., Aculops spp. such as A. lycopersici, A. pelekassi; Aculus spp. such as A. schlechtendali, Colomerus vitis, Epitrimerus gyri, Phyllocoptruta oleivora; Eriophytes ribis and Eriophyes spp. such as Eriophyes sheldoni; Family Tarsonemidae including Hemitarsonemus spp., Phytonemus pallidus and Polyphagotarsonemus latus, Stenotarsonemus spp. Steneotarsonemus spinki; Family Tenuipalpidae including Brevipalpus spp. such as B. phoenicis; Family Tetranychidae including Eotetranychus spp., Eutetranychus spp., Oligonychus spp., Petrobia latens, Tetranychus spp. such as T. cinnabarinus, T. evansi, T. kanzawai, T, pacificus, T. phaseulus, T. telarius and T. urticae; Bryobia praetiosa; Panonychus spp. such as P. ulmi, P. citri; Metatetranychus spp. and Oligonychus spp. such as O. pratensis, O. perseae, Vasates lycopersici; Raoiella indica, Family Carpoglyphidae including Carpoglyphus spp.; Penthaleidae spp. such as

*Halotydeus destructor*, Family Demodicidae with species such as *Demodex* spp.; Family Trombicidea including *Trombicula* spp.; Family Macronyssidae including *Omothonyssus* spp.; Family Pyemotidae including *Pyemotes tritici; Tyrophagus putrescentiae*; Family Acaridae including *Acarus siro*; Family Araneida including *Latrodectus mactans, Tegenaria agrestis, Chiracanthium* sp, *Lycosa* sp *Achaearanea tepidariorum* and *Loxosceles reclusa;*

Pests from the Phylum Nematoda, for example, plant parasitic nematodes such as root-knot nematodes, *Meloidogyne* spp. such as *M. hapla, M. incognita, M. javanica*; cyst-forming nematodes, *Globodera* spp. such as *G. rostochiensis; Heterodera* spp. such as *H. avenae, H. glycines, H. schachtii, H. trifolii*; Seed gall nematodes, *Anguina* spp.; Stem and foliar nematodes, *Aphelenchoides* spp. such as *A. besseyi*; Sting nematodes, *Belonolaimus* spp. such as *B. longicaudatus;* Pine nematodes, *Bursaphelenchus* spp. such as *B. lignicolus, B. xylophilus*; Ring nematodes, *Criconema* spp., *Criconemella* spp. such as *C. xenoplax* and *C. omata*; and, *Criconemoides* spp. such as *Criconemoides informis; Mesocriconema* spp.; Stem and bulb nematodes, *Ditylenchus* spp. such as *D. destructor, D. dipsaci*; Awl nematodes, *Dolichodorus* spp.; Spiral nematodes, *Heliocotylenchus multicinctus*; Sheath and sheathoid nematodes, *Hemicycliophora* spp. and *Hemicriconemoides* spp.; *Hirshmanniella* spp.; Lance nematodes, *Hoploaimus* spp.; False rootknot nematodes, *Nacobbus* spp.; Needle nematodes, *Longidorus* spp. such as *L. elongatus*; Lesion nematodes, *Pratylenchus* spp. such as *P. brachyurus, P. neglectus, P. penetrans, P. curvitatus, P. goodeyi*; Burrowing nematodes, *Radopholus* spp. such as *R. similis; Rhadopholus* spp.; *Rhodopholus* spp.; *Reniform* nematodes, *Rotylenchus* spp. such as *R. robustus, R. renlformis; Scutellonema* spp.; Stubby-root nematode, *Trichodorus* spp. such as *T. obtusus, T. primitivus; Paratrichodorus* spp. such as *P. minor*; Stunt nematodes, *Tylenchorhynchus* spp. such as *T. claytoni, T. dubius*; Citrus nematodes, *Tylenchulus* spp. such as *T. semipenetrans;* Dagger nematodes, *Xiphinema* spp.; and other plant parasitic nematode species;

Insects from the order Isoptera for example *Calotermes Coptotermes* spp. such as *C. formosanus, C. gestroi, C. acinaciformis; Cornitermes cumulans, Cryptotermes* spp. such as *C. brevis, C. cavifrons; Globitermes sulfureus, Heterotermes* spp. such as *H. aureus, H. longiceps, H. tenuis; Leucotermes flavipes, Odontotermes* spp., *Incisitermes* spp. such as *I. minor, I. Snyder, Marginitermes hubbardi, Mastotermes* spp. such as *M. darwiniensis Neocapritermes* spp. such as *N. opacus, N. parvus; Neotermes* spp., *Procornitermes* spp., *Zootermopsis* spp. such as *Z. angusticollis, Z. nevadensis, Reticulitermes* spp. such as *R. hesperus, R. tibialis, R. speratus, R. flavipes, R. grassei, R. lucifugus, R. santonensis, R. virginicus; Termes natalensis,*

Insects from the order Blattaria for example *Blatta* spp. such as *B. orientalis, B. lateralis; Blattella* spp. such as *B. asahinae, B. germanica; Leucophaea maderae, Panchlora nivea, Periplaneta* spp. such as *P. americana, P. australasiae, P. brunnea, P. fuligginosa, P. japonica; Supella longipalpa, Parcoblatta pennylvanica, floridana, Pycnoscelus surinamensis,*

Insects from the order Siphonoptera for example *Cediopsylla simples, Ceratophyllus* spp., *Ctenocephalides* spp. such as *C. fells, C. canis, Xenopsylla cheopis, Pulex irritans, Trichodectes Tunga penetrans,* and *Nosopsyllus fasciatus,*

Insects from the order Thysanura for example *Lepisma saccharin, Ctenolepisma urban,* and *Thermobia domestica,*

Pests from the class Chilopoda for example *Geophllus* spp., *Scutigera* spp. such as *Scutigera coleoptrata;*

Pests from the class Diplopoda for example *Blaniulus guttulatus, Julus* spp., *Narceus* spp., Pests from the class Symphyla for example *Scutigerella immaculata,*

Insects from the order Dermaptera, for example *Forticula auricularia,*

Insects from the order Collembola, for example *Onychiurus* spp., such as *Onychiurus armatus,*

Pests from the order Isopoda for example, *Armadillidium vulgare, Oniscus asellus, Porcellio scaber,*

Insects from the order Phthiraptera, for example *Damalinia* spp., *Pediculus* spp. such as *Pediculus humanus capitis, Pediculus humanus corporis, Pediculus humanus humanus; Pthirus pubis, Haematopinus* spp. such as *Haematopinus eurysternus, Haematopinus suis; Linognathus* spp. such as *Linognathus Bovicola bovis, Menopon gallinae, Menacanthus stramineus* and *Solenopotes capillatus, Trichodectes* spp., Examples of further pest species which may be controlled by compounds of formula (I) include: from the Phylum Mollusca, class Bivalvia, for example, *Dreissena* spp.; class Gastropoda, for example, *Arion* spp., *Biomphalana* spp., *Bulinus* spp., *Deroceras* spp., *Galba* spp., *Lymnaea* spp., *Oncomelania* spp., *Pomacea canaliclata, Succinea* spp.; from the class of the helminths, for example, *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus Diphyllobothrium latum, Dracunculus medinensis, Echinococcus granulosus, Echinococcus mufilloculariss, Enterobius vermicularis, Faciola* spp., *Haemonchus* spp. such as *Haemonchus contortus; Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercora lis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichunis trichiura, Wuchereria bancrofii.*

The compounds of the present invention are suitable for use in treating or protecting animals against infestation or infection by parasites. Therefore, the present invention also relates to the use of a compound of the present invention for the manufacture of a medicament for the treatment or protection of animals against infestation or infection by parasites. Furthermore, the present invention relates to a method of treating or protecting animals against infestation and infection by parasites, which comprises orally, topically or parenterally administering or applying to the animals a parasiticidally effective amount of a compound of the present invention.

The present invention also relates to the non-therapeutic use of compounds of the present invention for treating or protecting animals against infestation and infection by parasites. Moreover, the present invention relates to a non-therapeutic method of treating or protecting animals against infestation and infection by parasites, which comprises applying to a locus a parasiticidally effective amount of a compound of the present invention.

The compounds of the present invention are further suitable for use in combating or controlling parasites in and on animals. Furthermore, the present invention relates to a method of combating or controlling parasites in and on animals, which comprises contacting the parasites with a parasitically effective amount of a compound of the present invention.

The present invention also relates to the non-therapeutic use of compounds of the present invention for controlling or combating parasites. Moreover, the present invention relates to a non-therapeutic method of combating or controlling parasites, which comprises applying to a locus a parasiticidally effective amount of a compound of the present invention.

The compounds of the present invention can be effective through both contact (via soil, glass, wall, bed net, carpet, blankets or animal parts) and ingestion (e.g. baits). Furthermore, the compounds of the present invention can be applied to any and all developmental stages.

The compounds of the present invention can be applied as such or in form of compositions comprising the compounds of the present invention.

The compounds of the present invention can also be applied together with a mixing partner, which acts against pathogenic parasites, e.g. with synthetic coccidiosis compounds, polyetherantibiotics such as Amprolium, Robenidin, Toltrazuril, Monensin, Salinomycin, Maduramicin, Lasalocid, Narasin or Semduramicin, or with other mixing partners as defined above, or in form of compositions comprising said mixtures.

The compounds of the present invention and compositions comprising them can be applied orally, parenterally or topically, e.g. dermally. The compounds of the present invention can be systemically or non-systemically effective.

The application can be carried out prophylactically, therapeutically or non-therapeutically. Furthermore, the application can be carried out preventively to places at which occurrence of the parasites is expected.

As used herein, the term "contacting" includes both direct contact (applying the compounds/compositions directly on the parasite, including the application directly on the animal or excluding the application directly on the animal, e.g. at its locus for the latter) and indirect contact (applying the compounds/compositions to the locus of the parasite). The contact of the parasite through application to its locus is an example of a non-therapeutic use of the compounds of the present invention.

The term "locus" means the habitat, food supply, breeding ground, area, material or environment in which a parasite is growing or may grow outside of the animal.

As used herein, the term "parasites" includes endo- and ectoparasites. In some embodiments of the present invention, endoparasites can be preferred. In other embodiments, ectoparasites can be preferred. Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the present invention are especially useful for combating parasites of the following orders and species, respectively:

fleas (Siphonaptera), e.g. *Ctenocephalides fells, Ctenocephalides canis, Xenopsylla cheopis, Pulex irritans, Tunga penetrans*, and *Nosopsyllus fasciatus*; cockroaches (Blattaria—Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis*; flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops sllacea, Cholsops atlanticus, Cochliomyia hominivorax, Cordylobia anthropophaga, Culicoides furens, Culex pipiens, Culex nigripalpus, Culex quinquefasciatus, Culex tarsalis, Culiseta inomata, Culiseta melanura, Dermatobia hominis, Fannia canicularis, Gasterophllus intestinalis, Glossina morsitans, Glossina palpalis, Glossina fuscipes, Glossina tachinoides, Haematobia irritans, Haplodiplosis equestris, Hippelates spp., Hypoderma lineata, Leptoconops torrens, Lucilia caprin, Lucilia cuprina, Lucilia sericata, Lycoria pectoralis, Mansonia spp., Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga sp., Simulium vittatum, Stomoxys calcitrans, Tabanus bovinus, Tabanus atratus, Tabanus lineola*, and *Tabanus similis*; lice (Phthiraptera), e.g. *Pediculus humanus capitis, Pediculus humanus corporis, Pthirus pubis, Haematopinus eurysternus, Haematopinus suis, Linognathus Bovicola bovis, Menopon gallinae, Menacanthus stramineus* and *Solenopotes capillatus*; ticks and parasitic mites (Parasitiformes): ticks (Ixodida), e.g. *Ixodes scapularis, Ixodes holocyclus, Ixodes pacificus, Rhiphicephalus sanguineus, Dermacentor andersom, Dermacentor variabllis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae*; Actinedida (Prostigmata) and Acaridida (Astigmata), e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp; Bugs (Heteropterida): *Cimex lectularius, Cimex hemipterus, Reduvius senllis, Triatoma* spp., *Rhodnius* ssp., *Panstrongylus* ssp., and *Arilus critatus*; Anoplurida, e.g. *Haematopinus* spp., *Linognathus* spp., *Pediculus* spp., *Phtirus* spp., and *Solenopotes* spp.; Mallophagida (suborders *Arnblycerina* and *Ischnocerina*), e.g. *Trimenopon* spp., *Menopon* spp., *Trinoton* spp., *Bovicola* spp., *Werneckiella* spp., *Lepikentron* spp., *Trichodectes* spp., and *Felicola* spp.; Roundworms Nematoda: Wipeworms and Trichinosis (Trichosyringida), e.g. Trichinellidae (*Trichinella* spp), (Irichuridae) *Trichunis* spp., *Capillaria* spp.; Rhabditida, e.g. *Rhabditis* spp., *Strongyloides* spp., *Helicephalobus* spp.; Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp., *Aleurostrongylus abstrusus*, and *Dioctophyma renale*; Intestinal roundworms (Ascaridida), e.g. *Ascanis lumbricoides, Ascanis suum, Ascaridia galli, Parascaris equorum, Enterobius vermiculanis* (Threadworm), *Toxocara canis, Toxascaris leonine, Skrjabinema* spp., and *Oxyuris equi*; Cannallanida, e.g. *Dracunculus medinensis* (guinea worm); Spirurida, e.g. *Thelazia* spp., *Wuchereria* spp., *Brugia* spp., *Onchocerca* spp., *Dirotilari* spp. a, *Dipetalonema* spp., *Setaria* spp., *Elaeophora* spp., *Spirocerca lupi*, and *Habronema* spp.; Thorny headed worms (Acanthocephala), e.g. *Acanthocephalus* spp., *Macracanthorhynchus hirudinaceus* and *Oncicola* spp.; Planarians (Plathelminthes): Flukes (Trematoda), e.g. *Faciola* spp., *Fascioloides magna*, *Paragonimus* spp., *Dicrocoelium* spp., *Fasciolopsis buski*, *Clonorchlis sinensis, Schistosoma* spp., *Trichobilharzia* spp., *Alaria alata, Paragonimus* spp., and *Nanocyetes* spp.; Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

As used herein, the term "animal" includes warm-blooded animals (including humans) and fish. Preferred are mammals, such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels. Particularly preferred are domestic animals, such as dogs or cats.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

Generally, it is favorable to apply the compounds of the present invention in total amounts of 0.5 mg/kg to 100 mg/kg per day, preferably 1 mg/kg to 50 mg/kg per day.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further auxiliaries such as acids, bases, buffer salts, preservatives, and solubilizers. Suitable auxiliaries for injection solutions are known in the art. The solutions are filtered and filled sterile.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on. Solutions for use on the skin are prepared according to the state of the art and according to what is described above for injection solutions, sterile procedures not being necessary.

Gels are applied to or spread on the skin or introduced into body cavities. Gels are prepared by treating solutions which have been prepared as described in the case of the injection solutions with sufficient thickener that a clear material having an ointment-like consistency results. Suitable thickeners are known in the art.

Pour-on formulations are poured or sprayed onto limited areas of the skin, the active compound penetrating the skin and acting systemically. Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added. Suitable such auxiliaries are known in the art.

Emulsions can be administered orally, dermally or as injections. Emulsions are either of the water-in-oil type or of the oil-in-water type. They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances. Suitable hydrophobic phases (oils), suitable hydrophilic phases, suitable emulsifiers, and suitable further auxiliaries for emulsions are known in the art.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers. Suitable suspending agents, and suitable other auxiliaries for suspensions including wetting agents are known in the art.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form. Suitable auxiliaries for this purpose are known in the art.

The compositions which can be used in the invention can comprise generally from about 0.001 to 95% of the compound of the present invention.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

Topical application may be conducted with compound-containing shaped articles such as collars, medallions, ear tags, bands for fixing at body parts, and adhesive strips and foils.

Generally it is favorable to apply solid formulations which release compounds of the present invention in total amounts of 10 ring/kg to 300 mg/kg, preferably 20 mg/kg to 200 mg/kg, most preferably 25 mg/kg to 160 mg/kg body weight of the treated animal in the course of three weeks.

EXAMPLES

A. Preparation Examples

With appropriate modification of the starting materials, the procedures as described in Scheme 1 and the synthesis examples below were used to obtain further compounds I. The compounds obtained in this manner are listed in the table that follows, together with physical data.

The products shown below were characterized by melting point determination, by NMR spectroscopy or by the masses ([m/z]) or retention time (RT; [min.]) via HPLC-MS or HPLC spectrometry.

HPLC-MS=high performance liquid chromatography-coupled mass spectrometry; HPLC method 1: Phenomenex Kinetex 1.7 μm XB-C18 100A; 50×2.1 mm; mobile phase: A: water+0.1% trifluoroacetic acid (TFA); B: acetonitrile+0.1% TFA; gradient: 5-100% B in 1.50 minutes; 100% B 0.20 min; flow: 0.8-1.0 ml/min in 1.50 minutes at 60° C. MS: quadrupole electrospray ionization, 80 V (positive mode).

Scheme 1: Synthesis of compound I-9.

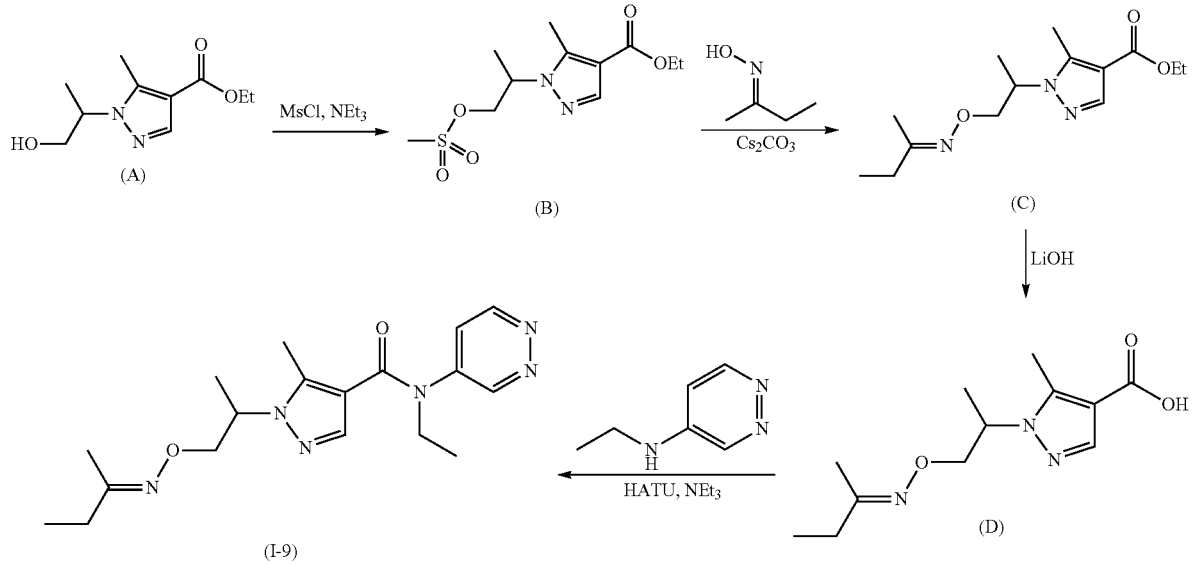

Example 1: Preparation of 5-methyl-1-(1-methyl-2-methylsulfonyloxy-ethyl)pyrazole-4-carboxylic acid ethyl ester (B)

To a stirred solution of 1-(2-hydroxy-1-methyl-ethyl)-5-methyl-pyrazole-4-carboxylic acid ethyl ester A (16 g, purity 92%, 69.2 mmol) in 150 mL dichloromethane was added dropwise methanesulfonyl chloride (24 g, 208 mmol). The mixture was cooled to −40° C. and triethylamine (21 g, 208 mmol) in 50 mL dichloromethane was added dropwise. Stirring was continued and the mixture was gradually warmed to 0° C. 100 mL water were added dropwise and the layers were separated. The organic phase was washed with water (100 mL), dried over sodium sulfate and the solvent was removed under reduced pressure to yield mesylate B (25 g, purity 80%) which was used without further purification.

Example 2: Preparation of ethyl 5-methyl-1-[1-methyl-2-[1-methylpropylidene-amino]oxy-ethyl] pyrazole-4-carboxylic acid ethyl ester (C)

To a solution of butan-2-one oxime (3.92 g, 45 mmol) in 70 mL acetonitrile was added caesium carbonate (14.7 g, 45 mmol) and the mixture was stirred at room temperature for 20 min. Then a solution of mesylate B (5.4 g, 15 mmol) in 20 mL acetonitrile was added dropwise and stirring was continued for 48 h. The reaction mixture was filtered and the solvent was removed under reduced pressure. Purification by reversed phase flash chromatography (H₂O/MeOH, 100:0→0:100) gave 1.18 g of oxime C (28%, 4.2 mmol). HPLC-MS: RT 1.118 min, m/z [MH]+282.2

Example 3: Preparation of 5-methyl-1-[1-methyl-2-[1-methylpropylidene-amino]oxy-ethyl]pyrazole-4-carboxylic acid (D)

To a solution of pyrazole carboxylic acid ethyl ester C (715 mg, 2.54 mmol) in 25 mL ethanol was added LiOH (183 mg, 7.64 mmol) in 5 mL water and the reaction mixture was stirred at room temperature overnight. Additional LiOH (150 mg, 6.26 mmol) were added and the mixture was stirred at 50° C. for 8 h. The solvent was removed under reduced pressure and the residue diluted with water. The mixture was washed with ethyl acetate (3×20 mL), acidified to pH 1 by addition of 2N aqueous HCl solution and precipitated acid D was filtered. Additionally, the solution was extracted with ethyl acetate (2×20 mL) and the combined organic layers were dried over sodium sulfate, filtered and the solvent was removed under reduced pressure. The combined carboxylic acid D (572 mg, 2.26 mmol, 89%) was used without further purification. 1H-NMR (MeOD, 500 MHz)•=1.04 (t, 3H), 1.46 (d, 3H), 1.68 (s, 3H), 2.15 (q, 2H), 2.50 (s, 3H), 4.16-4.28 (m, 2H), 4.71-4.81 (m, 1H), 7.87 (s, 1H) ppm.

Example 4: Preparation of N-ethyl-5-methyl-1-[1-methyl-2-[1-methyl-propylideneamino]oxy-ethyl]-N-pyridazin-4-yl-pyrazole-4-carboxamide (1-9)

To a solution of 258 mg (1.0 mmol) of 5-methyl-1-[1-methyl-2-[1-methylpropylidene-amino]oxy-ethyl]pyrazole-4-carboxylic acid in 10 mL DMF was added ethylaminopyridazine (370 mg, 3.0 mmol), HATU [O-(7-Azabenzotriazol-1-yl)-N,N,N',N'-tetramethyluronium-hexafluorphosphat] (1.52 g, 4.0 mmol) and triethylamine (606 mg, 6.0 mmol). The resulting mixture was stirred at room temperature overnight and the solvent was removed under reduced pressure. Purification by flash chromatography (cyclohexane/EtOAc/MeOH, 100:0:0→0:100:0→0:0:100) gave 190 mg of the title compound I-9 (53%). HPLC-MS: RT 0.872 min, m/z [MH]+358.9

The following compounds of formula I, wherein $R^{P1}$, $R^{P2}$, and $R^{P3}$ are in each case H, i.e. compounds falling under generic formula I*, were obtained in the same manner.

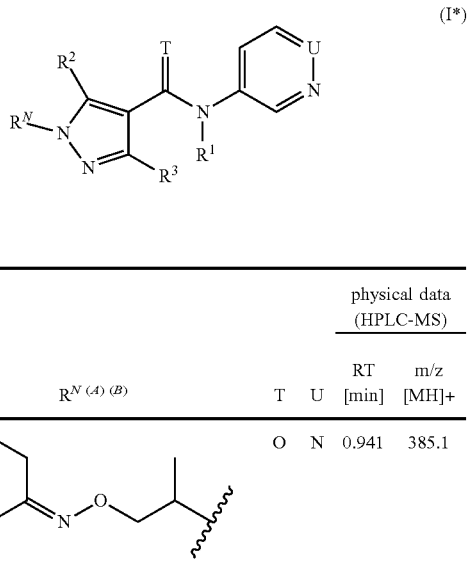

(I*)

| Comp. | R¹ | R² | R³ | R^N (A) (B) | T | U | RT [min] | m/z [MH]+ |
|---|---|---|---|---|---|---|---|---|
| I-1 | CH₂CH₃ | CH₃ | H | cyclohexyl=N-O-CH₂-CH(CH₃)- | O | N | 0.941 | 385.1 |
| I-2 | H | CH₃ | H | cyclohexyl=N-O-CH₂-CH(CH₃)- | O | N | 0.893 | 357.2 |
| I-3 | CH₃ | CH₃ | H | cyclohexyl=N-O-CH₂-CH(CH₃)- | O | N | 0.910 | 371.3 |
| I-4 | CH₂CH₃ | CH₃ | H | CH₃O-CH(CH₃)-CH=N-O-CH₂-CH(CH₃)- | O | N | 0.815 | 374.9 |
| I-5 | CH₃ | CH₃ | H | CH₃O-CH(CH₃)-CH=N-O-CH₂-CH(CH₃)- | O | N | 0.768 | 360.9 |

-continued

| Comp. | R¹ | R² | R³ | R^N (A)(B) | T | U | RT [min] | m/z [MH]+ |
|---|---|---|---|---|---|---|---|---|
| | | | | | | | physical data (HPLC-MS) | |
| I-6 | H | CH₃ | H | (structure) | O | N | 0.751 | 347.6 |
| I-7 | H | CH₃ | H | (structure) | O | N | 0.810 | 331.5 |
| I-8 | CH₃ | CH₃ | H | (structure) | O | N | 0.821 | 344.9 |
| I-9 | CH₂CH₃ | CH₃ | H | (structure) | O | N | 0.872 | 358.9 |

(A)In case of compounds I-4 to I-9: single isomer, E or Z not determined (B)"{" in each case marks the connection to the N atom of the pyrazole ring of formula I*

B. Biological Examples

The activity of the compounds of formula I of the present invention could be demonstrated and evaluated in biological tests described in the following.

If not otherwise specified the test solutions were prepared as follows:

The active compound was dissolved at the desired concentration in a mixture of 1:1 (vol:vol) distilled water: aceton. The test solution was prepared at the day of use and in general at concentrations of ppm (wt/vol).

B.1 Cowpea aphid (*Aphis craccivora*)

Potted cowpea plants colonized with 100-150 aphids of various stages were sprayed after the pest population had been recorded. Population reduction was assessed after 24, 72, and 120 hours.

In this test, the compounds I-1, I-2, I-3, I-4, I-5, I-6, I-7, I-8, and I-9, respectively, at 500 ppm showed a mortality of at least 75% in comparison with untreated controls.

B.2 Cotton aphid (*Aphis gossypii*, mixed life stages)

The active compounds were formulated in cyclohexanone as a 10,000 ppm solution supplied in 1.3 ml ABgene® tubes. These tubes were inserted into an automated electrostatic sprayer equipped with an atomizing nozzle and they served as stock solutions for which lower dilutions were made in 1:1 (vol:vol) water:aceton. A nonionic surfactant (Kinetic®) was included in the solution at a volume of 0.01% (v/v).

Cotton plants at the cotyledon stage were infested with aphids prior to treatment by placing a heavily infested leaf from the main aphid colony on top of each cotyledon. Aphids were allowed to transfer overnight to accomplish an infestation of 80-100 aphids per plant and the host leaf was removed. The infested plants were then sprayed by an automated electrostatic plant sprayer equipped with an atomizing spray nozzle. The plants were dried in the sprayer fume hood, removed from the sprayer, and then maintained in a growth room under fluorescent lighting in a 24-hr photoperiod at 25° C. and 20-40% relative humidity. Aphid mortality on the treated plants, relative to mortality on untreated control plants, was determined after 5 days.

In this test, the compounds I-3, I-4, I-5, I-6, I-7, I-8, and I-9, respectively, at 300 ppm showed a mortality of at least 75% in comparison with untreated controls.

B.3 Silverleaf whitefly (*Bemisia argentifolii*, adult)

The active compounds were formulated in cyclohexanone as a 10,000 ppm solution supplied in 1.3 ml ABgene® tubes. These tubes were inserted into an automated electrostatic sprayer equipped with an atomizing nozzle and they served as stock solutions for which lower dilutions were made in 1:1 (vol:vol) water:aceton. A nonionic surfactant (Kinetic®) was included in the solution at a volume of 0.01% (v/v).

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and 10 to 12 whitefly adults (approximately 3-5 days 2) were introduced. The insects were collected using an aspirator and 0.6 cm, nontoxic Tygon® tubing (R-3603) connected to a barrier pipette tip. The tip, containing the collected insects, was then gently inserted into the soil containing the treated plant, allowing insects to crawl out of the tip to reach the foliage for feeding. Cups were covered with a reusable screened lid (150-micron mesh polyester screen PeCap from Tetko, Inc.). Test plants were maintained in a growth room at 25° C. and 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, the compounds I-2, I-3, I-4, I-5, I-6, I-7, I-8, and I-9, respectively, at 300 ppm showed a mortality of at least 75% in comparison with untreated controls.

B.4 Vetch aphid (*Megoura viciae*)

The active compounds were formulated in 3:1 (vol:vol) water:DMSO with different concentrations of formulated compounds.

Bean leaf disks were placed into microtiterplates filled with 0.8% agar-agar and 2.5 ppm OPUS™. The leaf disks were sprayed with 2.5 µl of the test solution and 5 to 8 adult aphids were placed into the microtiter plates which were then closed and kept at 23±1° C. and 50±5% relative humidity under fluorescent light for 6 days. Mortality was assessed on the basis of vital, reproduced aphids. Aphid mortality and fecundity was then visually assessed.

In this test, the compounds I-1, I-2, I-3, I-4, I-5, I-6, I-7, and I-9, respectively, at 2500 ppm showed a mortality of at least 75% in comparison with untreated controls.

B.5 Green peach aphid (*Myzus persicae*)

The active compounds were formulated in cyclohexanone as a 10,000 ppm solution supplied in 1.3 ml ABgene® tubes. These tubes were inserted into an automated electrostatic sprayer equipped with an atomizing nozzle and they served as stock solutions for which lower dilutions were made in 1:1 (vol:vol) water:aceton. A nonionic surfactant (Kinetic®) was included in the solution at a volume of 0.01% (v/v).

Bell pepper plants at the first true-leaf stage were infested prior to treatment by placing heavily infested leaves from the main colony on top of the treatment plants. Aphids were allowed to transfer overnight to accomplish an infestation of 30-50 aphids per plant and the host leaves were removed. The infested plants were then sprayed by an automated electrostatic plant sprayer equipped with an atomizing spray nozzle. The plants were dried in the sprayer fume hood, removed, and then maintained in a growth room under fluorescent lighting in a 24 hour photoperiod at 25° C. and 20-40% relative humidity. Aphid mortality on the treated plants, relative to mortality on untreated control plants, was determined after 5 days.

In this test, the compounds I-2, I-3, I-4, I-5, I-6, I-7, I-8, and I-9, respectively, at 300 ppm showed a mortality of at least 75% in comparison with untreated controls.

B.6 Boll weevil (*Anthonomus grandis*)

The compounds were formulated in 3:1 (vol:vol) water:DMSO.

For evaluating control of boll weevil (*Anthonomus grandis*) the test unit consisted of 24-well-microtiter plates containing an insect diet and 20-30 *A. grandis* eggs. Different concentrations of formulated compounds were sprayed onto the insect diet at 20 µl, using a custom built micro atomizer, at two replications. After application, the microtiter plates were incubated at 23±1° C. and 50±5% relative humidity for 5 days. Egg and larval mortality was then visually assessed.

In this test, the compounds I-2 and I-6, respectively, at 2500 ppm showed a mortality of at least 75% in comparison with untreated controls.

B.7 Orchid thrips (*Dichromothrips corbetti*)

The active compounds were formulated as a 1:1 (vol:vol) water:aceton solution. Surfactant (Alkamuls EL 620) was added at the rate of 0.1% (vol/vol). Vanda orchids petals were cleaned, washed and air dried prior to spraying. Petals were dipped into the test solution for 3 seconds, air dried, placed inside a resealable plastic and inoculated with 20 adults. The treated petals were kept inside the h2ing room at 28-29° C. and relative humidity of 50-60%. Percent mortality was recorded after 72 hours.

In this test, the compounds I-4 and I-6, respectively, at 500 ppm showed a mortality of at least 75% in comparison with untreated controls.

B.8 Diamondback moth (*Plutella xylostella*)

The active compounds were formulated in 1:1 (vol:vol) water:aceton and 0.1% (vol/vol) Alkamuls EL 620 surfactant. A 6 cm leaf disk of cabbage leaves was dipped in the test solution for 3 seconds and allowed to air dry in a Petri plate lined with moist filter paper. The leaf disk was inoculated with 10 third instar larvae and kept at 25-27° C. and 50-60% humidity for 3 days. Mortality was assessed after 72 h of treatment.

In this test, the compounds I-4, and I-6, respectively, at 500 ppm showed a mortality of at least 75% in comparison with untreated controls.

The invention claimed is:

1. A pyrazole compound of formula I

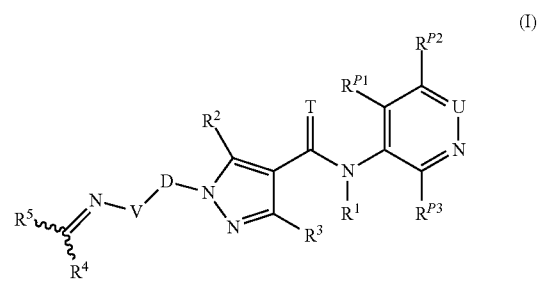

wherein

V is O, S or $NR^{1a}$, wherein $R^{1a}$ is selected from the group consisting of H, $C_1$-$C_{10}$-alkyl, $C_1$-$C_4$-haloalkyl, $C_3$-$C_{10}$-cycloalkyl, $C_3$-$C_{10}$-cycloalkylmethyl, $C_3$-$C_{10}$-halocycloalkyl, $C_2$-$C_{10}$-alkenyl, $C_2$-$C_{10}$-haloalkenyl, $C_2$-$C_{10}$-alkynyl, $C_1$-$C_{10}$-alkoxy-$C_1$-$C_4$-alkyl, $OR^a$, heterocyclyl, heterocyclyl-$C_1$-$C_4$-alkyl, phenyl, hetaryl, phenyl-$C_1$-$C_4$-alkyl and hetaryl-$C_1$-$C_4$-alkyl, wherein the ring in the six last mentioned radicals may be unsubstituted or may carry 1, 2, 3, 4 or 5 identical or different substituents selected from the group consisting of halogen, CN, $NO_2$, $C_1$-$C_4$-alkyl, $C_1$-$C_4$-haloalkyl, $C_1$-$C_4$-alkoxy and $C_1$-$C_4$-haloalkoxy, or wherein $R^{1a}$ and $R^4$ together with the carbon atom to which $R^4$ is bound and the nitrogen atom to which $R^{1a}$ is bound as well as the nitrogen atom between said carbon atom and said nitrogen atom form a 4- to 8-membered heterocycle, which contains the two nitrogen atoms as heteroatoms, and may further contain 1 or 2 heteroatoms which, independently of each other, are selected from the group consisting of $NR^B$, O, and S, wherein S may be oxidized, and/or wherein the heterocycle may be unsubstituted or may be partially or fully substituted by substituents which, independently of each other, are selected from $R^A$;

D is selected from the group consisting of $C_1$-$C_8$-alkylene, $C_3$-$C_8$-cycloalkylene, $C_3$-$C_8$-heterocycloalkylene, $C_2$-$C_8$-alkenylene, $C_3$-$C_8$-cycloalkenylene, $C_3$-$C_8$-heterocycloalkenylene, and $C_2$-$C_8$-alkynylene, wherein D may be unsubstituted or may be partially or fully substituted by substituents which, independently of each other, are selected from $R^A$;

U is N or $CR^U$;

T is S, O or $NR^{1b}$, wherein $R^{1b}$ is selected from the group consisting of H, $C_1$-$C_{10}$-alkyl, $C_1$-$C_4$-haloalkyl, $C_3$-$C_{10}$-cycloalkyl, $C_3$-$C_{10}$-cycloalkylmethyl, $C_3$-$C_{10}$-halocycloalkyl, $C_2$-$C_{10}$-alkenyl, $C_2$-$C_{10}$-haloalkenyl, $C_2$-$C_{10}$-alkynyl, $C_1$-$C_{10}$-alkoxy-$C_1$-$C_4$-alkyl, $OR^a$, heterocyclyl, heterocyclyl-$C_1$-$C_4$-alkyl, phenyl, hetaryl, phenyl-$C_1$-$C_4$-alkyl and hetaryl-$C_1$-$C_4$-alkyl, wherein the ring in the six last mentioned radicals may be unsubstituted or may carry 1, 2, 3, 4 or 5 identical or different substituents selected from the group consisting of halogen, CN, $NO_2$, $C_1$-$C_4$-alkyl, $C_1$-$C_4$-haloalkyl, $C_1$-$C_4$-alkoxy and $C_1$-$C_4$-haloalkoxy;

$R^{P1}$, $R^{P2}$, $R^{P3}$, and $R^U$ are independently of each other selected from the group consisting of H, halogen, $C_1$-$C_4$-alkyl, $C_1$-$C_3$-haloalkyl, $C_1$-$C_4$-alkoxy, $C_1$-$C_3$-haloalkoxy, $C_1$-$C_4$-alkylthio, $C_1$-$C_3$-haloalkylthio, $C_1$-$C_4$-alkylsulfinyl, $C_1$-$C_3$-haloalkylsulfinyl, $C_1$-$C_4$-alkylsulfonyl, $C_1$-$C_3$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl;

$R^1$ is selected from the group consisting of H, CN, $C_1$-$C_{10}$-alkyl, $C_1$-$C_{10}$-haloalkyl, $C_3$-$C_{10}$-cycloalkyl, $C_3$-$C_{10}$-halocycloalkyl, $C_1$-$C_4$-alkoxy-$C_1$-$C_4$-alkyl, $C_2$-$C_{10}$-alkenyl, $C_2$-$C_{10}$-haloalkenyl, $C_2$-$C_{10}$-alkynyl, $C_3$-$C_{10}$-haloalkynyl, $C_1$-$C_5$-alkylen-CN, $OR^a$, $C_1$-$C_5$-alkylen-$OR^a$, $C(Y)R^b$, $C_1$-$C_5$-alkylen-$C(Y)R^b$, $C(Y)OR^c$, $C_1$-$C_5$-alkylen-$C(Y)OR^c$, $S(O)_2R^d$, $NR^eR^f$, $C_1$-$C_5$-alkylen-$NR^eR^f$, $C(Y)NR^gR^h$, $C_1$-$C_5$-alkylen-$C(Y)NR^gR^h$, $S(O)_nNR^eR^f$, $C(Y)NR^iNR^eR^f$, $C_1$-$C_5$-alkylen-$S(O)_2R^d$, $C_1$-$C_5$-alkylen-$S(O)_nNR^eR^f$, $C_1$-$C_5$-alkylen-$C(Y)NR^iNR^eR^f$, phenyl, heterocyclyl, hetaryl, phenyl-$C_1$-$C_5$-alkyl, $C_3$-$C_{10}$-cycloalkyl-$C_1$-$C_5$-alkyl, heterocyclyl-$C_1$-$C_5$-alkyl and hetaryl-$C_1$-$C_5$-alkyl wherein the ring of the seven last mentioned radicals may be unsubstituted or may carry 1, 2, 3, 4 or 5 identical or different substituents selected from the radicals $R^y$ and $R^x$;

$R^2$ and $R^3$ are independently of each other selected from the group consisting of H, halogen, CN, $NO_2$, $C_1$-$C_{10}$-alkyl, $C_2$-$C_{10}$-alkenyl and $C_2$-$C_{10}$-alkynyl, wherein the 3 last mentioned radicals may be unsubstituted, may be partially or fully halogenated or may carry 1, 2 or 3 identical or different substituents $R^x$, or wherein $R^2$ and $R^3$ are further selected from the group consisting of $OR^a$, $SR^a$, $C(Y)R^b$, $C(Y)OR^c$, $S(O)R^d$, $S(O)_2R^d$, $NR^eR^f$, $C(Y)NR^gR^h$, heterocyclyl, hetaryl, $C_3$-$C_{10}$-cycloalkyl, $C_5$-$C_{10}$-cycloalkenyl and phenyl, wherein the five last mentioned radicals may be unsubstituted or may carry 1, 2, 3, 4 or 5 identical or different substituents selected from the radicals $R^y$ and $R^x$, and wherein $R^4$ is selected from the group consisting of H, $C_1$-$C_6$-alkyl, $C_1$-$C_6$-alkyl-X, $C_3$-$C_6$-cycloalkyl and $C_3$-$C_6$-cycloalkyl-X, wherein X is selected from the group consisting of O, S, and $NR^B$, wherein the $C_1$-$C_6$-alkyl or $C_3$-$C_6$-cycloalkyl may be unsubstituted or may be partially or fully substituted by substituents which, independently of each other, are selected from $R^A$; and $R^5$ is selected from the group consisting of $C_1$-$C_6$-alkyl, $C_1$-$C_6$-alkyl-X, $C_3$-$C_6$-cycloalkyl and $C_3$-$C_6$-cycloalkyl-X, wherein X is selected from the group consisting of O, S, and $NR^B$, wherein the $C_1$-$C_6$-alkyl or $C_3$-$C_6$-cycloalkyl may be unsubstituted or may be partially or fully substituted by substituents which, independently of each other, are selected from $R^A$, or wherein $R^4$ and $R^5$ together with the carbon atom to which they are bound form a 3- to 8-membered, saturated or unsaturated carbo- or heterocycle, which may contain 1, 2, or 3 heteroatoms which, independently of each other, are selected from the group consisting of $NR^B$, O, and S, wherein S may be oxidized and/or wherein the carbo- or heterocycle may be unsubstituted or may be partially or fully substituted by substituents which, independently of each other, are selected from $R^A$;

and wherein $R^A$ is selected from the group consisting of halogen, $NO_2$, CN, $C_1$-$C_6$-alkyl, $C_1$-$C_6$-alkoxy, $C_1$-$C_6$-haloalkyl, $C_1$-$C_6$-haloalkoxy, $C_3$-$C_6$-cycloalkyl, $C_3$-$C_6$-cycloalkoxy, $C_3$-$C_6$-halocycloalkyl, $C_3$-$C_6$-halocycloalkoxy, $C_2$-$C_4$-alkenyl, $C_2$-$C_4$-alkynyl, $S(O)_nR^D$, =O, =S, =$NR^C$, =$NOR^C$, and =$NSR^C$; or wherein two $R^A$ bound to the same carbon atom or to adjacent carbon atoms together with the carbon atom(s) to which they are bound form a 3- to 6-membered, saturated or unsaturated carbo- or heterocycle, which may contain 1 or 2 heteroatoms which, independently of each other, are selected from the group consisting of $NR^B$, O, and S, wherein S may be oxidized;

and wherein $R^B$ is selected from the group consisting of H, $C_1$-$C_2$-alkyl, $C_1$-$C_2$-haloalkyl, $C_1$-$C_2$-alkylcarbonyl, $C_1$-$C_2$-haloalkylcarbonyl, and $C_1$-$C_2$-alkoxycarbonyl;

$R^C$ is selected from the group consisting of H, $C_1$-$C_4$-alkyl, $C_1$-$C_4$-haloalkyl, $C_3$-$C_6$-cycloalkyl, and $C_3$-$C_6$-halocycloalkyl;

$R^D$ is selected from the group consisting of H, $C_1$-$C_4$-alkyl, $C_1$-$C_4$-haloalkyl, $C_3$-$C_6$-cycloalkyl, or $C_3$-$C_6$-halocycloalkyl, $C_1$-$C_4$-alkoxy, and $C_1$-$C_4$-haloalkoxy;

n is 0, 1, or 2;

Y is O or S;

$R^a$, $R^b$, $R^c$ are independently of each other selected from the group consisting of H, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, phenyl, hetaryl, phenyl-$C_1$-$C_4$-alkyl and hetaryl-$C_1$-$C_4$-alkyl, wherein the ring in the six last mentioned radicals may be unsubstituted or may carry 1, 2, 3, 4 or 5 substituents which, independently of each other, are selected from the group consisting of halogen, CN, $NO_2$, $C_1$-$C_4$-alkyl, $C_1$-$C_4$-haloalkyl, $C_1$-$C_4$-alkoxy and $C_1$-$C_4$-haloalkoxy;

$R^d$ is selected from the group consisting of $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, phenyl, hetaryl, phenyl-$C_1$-$C_4$-alkyl and hetaryl-$C_1$-$C_4$-alkyl, wherein the ring in the six last mentioned radicals may be unsubstituted or may carry 1, 2, 3, 4 or 5 substituents which are independently of each other selected from the group consisting of halogen, CN, $NO_2$, $C_1$-$C_4$-alkyl, $C_1$-$C_4$-haloalkyl, $C_1$-$C_4$-alkoxy and $C_1$-$C_4$-haloalkoxy; and wherein $R^e$ and $R^f$ are independently of each other selected from the group consisting of H, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, heterocyclyl, heterocyclyl-$C_1$-$C_4$-alkyl, heterocyclylcarbonyl, heterocyclylsulfonyl, phenyl, phenylcarbonyl, phenylsulfonyl, hetaryl, hetarylcarbonyl, hetarylsulfonyl, phenyl-$C_1$-$C_4$-alkyl and hetaryl-$C_1$-$C_4$-alkyl, wherein the ring in the twelve last mentioned radicals may be unsubstituted or may carry 1, 2, 3, 4 or 5 substituents which, independently of each other, are selected from the group consisting of halogen, CN, $NO_2$, $C_1$-$C_4$-alkyl, $C_1$-$C_4$-haloalkyl, $C_1$-$C_4$-alkoxy and $C_1$-$C_4$-haloalkoxy; or $R^e$ and $R^f$ together with the nitrogen atom to which they are bound form a 5- or 6-membered, saturated or unsaturated heterocycle, which may carry a further heteroatom being selected from the group consisting of O, S and N as a ring member atom and wherein the heterocycle may be unsubstituted or may carry 1, 2, 3, 4 or 5 substituents which are independently of each other selected from the group consisting of halogen, CN, $NO_2$, $C_1$-$C_4$-alkyl, $C_1$-$C_4$-haloalkyl, $C_1$-$C_4$-alkoxy and $C_1$-$C_4$-haloalkoxy;

and wherein $R^g$ and $R^h$ are independently of each other selected from the group consisting of H, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, phenyl, hetaryl, phenyl-$C_1$-$C_4$-alkyl and hetaryl-$C_1$-$C_4$-alkyl, wherein the ring in the six last mentioned radicals may be unsubstituted or may carry 1, 2, 3, 4 or 5 substituents which are independently of each other selected from the group consisting of halogen, CN, $NO_2$, $C_1$-$C_4$-alkyl, $C_1$-$C_4$-haloalkyl, $C_1$-$C_4$-alkoxy and $C_1$-$C_4$-haloalkoxy;

$R^i$ is selected from the group consisting of H, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl and phenyl-$C_1$-$C_4$-alkyl wherein the phenyl ring in the two last mentioned radicals may be unsubstituted or may carry 1, 2, 3, 4 or 5 substituents which are independently of each other selected from the group consisting of halogen, CN, $NO_2$, $C_1$-$C_4$-alkyl, $C_1$-$C_4$-haloalkyl, $C_1$-$C_4$-alkoxy and $C_1$-$C_4$-haloalkoxy;

$R^x$ is selected from the group consisting of CN, $NO_2$, $C_1$-$C_4$-alkoxy, $C_1$-$C_4$-haloalkoxy, $S(O)_nR^d$, $S(O)_n NR^eR^f$, $C_1$-$C_{10}$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, 5- to 7-membered heterocyclyl, 5- or 6-membered hetaryl, phenyl, $C_3$-$C_6$-cycloalkoxy, 3- to 6-membered heterocyclyloxy and phenoxy, wherein the last 7 mentioned radicals may be unsubstituted or may carry 1, 2, 3, 4 or 5 identical or different radicals $R^y$; and $R^y$ is selected from the group consisting of halogen, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_nR^d$, $S(O)_n NR^eR^f$, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_1$-$C_4$-alkoxy-$C_1$-$C_4$-alkyl, and/or a salt, stereoisomer, tautomer, or N-oxide thereof.

2. The compound of formula I of claim 1, wherein V is O or S.

3. The compound of formula I of claim 1, wherein D is $C_1$-$C_8$-alkylene, $C_3$-$C_8$-cycloalkylene or $C_3$-$C_8$-heterocycloalkylene, and wherein D may be unsubstituted or may be partially or fully substituted by substituents which, independently of each other, are selected from $R^A$.

4. The compound of formula I of claim 3, wherein D is a branched $C_2$-$C_8$-alkylene, and wherein the branched $C_2$-$C_8$-alkylene may be unsubstituted or may be partially or fully substituted by substituents which, independently of each other, are selected from $R^A$.

5. The compound of formula I of claim 3, wherein D is $CH(CH_3)CH_2$, wherein the $CH_2$ group is bound to V and the $CH(CH_3)$ group is bound to the nitrogen atom of the pyrazole moiety, so that a connectivity of V—$CH_2$CH($CH_3$)—N is obtained.

6. The compound of formula I of claim 1, wherein $R^4$ is selected from the group consisting of H, $C_1$-$C_4$-alkyl, $C_1$-$C_4$-haloalkyl, $C_3$-$C_6$-cycloalkyl and $C_3$-$C_6$-cycloalkylmethyl, and $R^5$ is selected from the group consisting of $C_1$-$C_4$-alkyl, $C_1$-$C_4$-haloalkyl, $C_3$-$C_6$-cycloalkyl and $C_3$-$C_6$-cycloalkylmethyl, wherein in each case the $C_1$-$C_4$-alkyl, $C_1$-$C_4$-haloalkyl, $C_3$-$C_6$-cycloalkyl or $C_3$-$C_6$-cycloalkylmethyl may be unsubstituted or may be partially or fully substituted by substituents which, independently of each other, are selected from $R^A$, or wherein $R^4$ and $R^5$ together with the carbon atom to which they are bound form a non-aromatic 5- to 6-membered carbo- or heterocycle, which may contain 1 or 2 heteroatoms which, independently from each other, are selected from the group consisting of $NR^B$, O, and S, wherein S may be oxidised, and/or wherein the carbo- or heterocycle may be unsubstituted or may be partially or fully substituted by substituents which, independently of each other, are selected from $R^A$.

7. The compound of formula I of claim 1, wherein

U is N or CH, and

T is O, and $R^{P1}$, $R^{P2}$, and $R^{P3}$ are H.

8. The compound of formula I of claim 1, wherein $R^1$ is selected from the group consisting of H, $C_1$-$C_2$-alkyl, and $C_1$-$C_2$-alkoxy-$C_1$-$C_2$-alkyl, and wherein $R^2$ and $R^3$ are independently of each other selected from the group consisting of H, halogen, CN, $C_1$-$C_4$-alkyl, $C_1$-$C_4$-haloalkyl, $C_3$-$C_4$-cycloalkyl, $C_3$-$C_4$-halocycloalkyl, $OR^a$, and $SR^a$, wherein $R^a$ is selected from the group consisting of $C_1$-$C_4$-alkyl, $C_1$-$C_4$-haloalkyl, $C_3$-$C_4$-cycloalkyl, and $C_3$-$C_4$-halocycloalkyl, wherein $R^2$ is selected from the group consisting of $C_1$-$C_2$-alkyl, $C_1$-$C_2$-haloalkyl, $C_3$-cycloalkyl, and $C_3$-halocycloalkyl, and wherein $R^3$ is H.

9. The compound of formula I of claim 1, wherein $R^4$ is selected from the group consisting of halogen, CN, $C_1$-$C_2$-alkyl, $C_1$-$C_2$-haloalkyl, $C_1$-$C_2$-alkoxy, $C_1$-$C_2$-haloalkoxy, $C_3$-$C_4$-cycloalkyl, $C_3$-$C_4$-halocycloalkyl, $C_3$-$C_4$-cycloalkoxy, and $C_3$-$C_4$-halocycloalkoxy, or wherein two $R^4$ are bound to the same carbon atom and together with the carbon atom to which they are bound form a cyclopropane.

10. A composition comprising at least one compound of claim 1 and at least one inert liquid and/or solid carrier.

11. An agricultural composition for combating animal pests comprising at least one compound of claim 1 and at least one inert liquid and/or solid acceptable carrier and, if desired, at least one surfactant.

12. A method for combating or controlling invertebrate pests, comprising contacting said pest or its food supply, habitat or breeding grounds with a pesticidally effective amount of at least one compound of claim 1.

13. A method for protecting growing plants from attack or infestation by invertebrate pests, comprising contacting a plant, or soil or water in which the plant is growing, with a pesticidally effective amount of at least one compound of claim 1.

14. A seed treated with the compound of claim 1, and/or an enantiomer, diastereomer or salt thereof, in an amount of from 0.1 g to 10 kg per 100 kg of seed.

15. The method of claim 12, wherein V is O or S.

16. The method of claim 12, wherein D is $C_1$-$C_8$-alkylene, $C_3$-$C_8$-cycloalkylene or $C_3$-$C_8$-heterocycloalkylene, and wherein D may be unsubstituted or may be partially or fully substituted by substituents which, independently of each other, are selected from $R^A$.

17. The method of claim 16, wherein D is a branched $C_2$-$C_8$-alkylene, and wherein the branched $C_2$-$C_8$-alkylene may be unsubstituted or may be partially or fully substituted by substituents which, independently of each other, are selected from $R^A$.

18. The method of claim 15, wherein D is $CH(CH_3)CH_2$, wherein the $CH_2$ group is bound to V and the $CH(CH_3)$ group is bound to the nitrogen atom of the pyrazole moiety, so that a connectivity of V—$CH_2CH(CH_3)$—N is obtained.

19. The c method of claim 12, wherein $R^4$ is selected from the group consisting of H, $C_1$-$C_4$-alkyl, $C_1$-$C_4$-haloalkyl, $C_3$-$C_6$-cycloalkyl and $C_3$-$C_6$-cycloalkylmethyl, and $R^5$ is selected from the group consisting of $C_1$-$C_4$-alkyl, $C_1$-$C_4$-haloalkyl, $C_3$-$C_6$-cycloalkyl and $C_3$-$C_6$-cycloalkylmethyl, wherein in each case the $C_1$-$C_4$-alkyl, $C_1$-$C_4$-haloalkyl, $C_3$-$C_6$-cycloalkyl or $C_3$-$C_6$-cycloalkylmethyl may be unsubstituted or may be partially or fully substituted by substituents which, independently of each other, are selected from $R^A$, or wherein $R^4$ and $R^5$ together with the carbon atom to which they are bound form a non-aromatic 5- to 6-membered carbo- or heterocycle, which may contain 1 or 2 heteroatoms which, independently from each other, are selected from the group consisting of $NR^B$, O, and S, wherein S may be oxidised, and/or wherein the carbo- or heterocycle may be unsubstituted or may be partially or fully substituted by substituents which, independently of each other, are selected from $R^A$.

20. The method of claim 12, wherein
U is N or CH, and
T is O, and
$R^{P1}$, $R^{P2}$, and $R^{P3}$ are H.

21. The method of claim 12, wherein $R^1$ is selected from the group consisting of H, $C_1$-$C_2$-alkyl, and $C_1$-$C_2$-alkoxy-$C_1$-$C_2$-alkyl, and wherein $R^2$ and $R^3$ are independently of each other selected from the group consisting of H, halogen, CN, $C_1$-$C_4$-alkyl, $C_1$-$C_4$-haloalkyl, $C_3$-$C_4$-cycloalkyl, $C_3$-$C_4$-halocycloalkyl, $OR^a$, and $SR^a$, wherein $R^a$ is selected from the group consisting of $C_1$-$C_4$-alkyl, $C_1$-$C_4$-haloalkyl, $C_3$-$C_4$-cycloalkyl, and $C_3$-$C_4$-halocycloalkyl, wherein $R^2$ is selected from the group consisting of $C_1$-$C_2$-alkyl, $C_1$-$C_2$-haloalkyl, $C_3$-cycloalkyl, and $C_3$-halocycloalkyl, and wherein $R^3$ is H.

22. The method of claim 12, wherein $R^A$ is selected from the group consisting of halogen, CN, $C_1$-$C_2$-alkyl, $C_1$-$C_2$-haloalkyl, $C_1$-$C_2$-alkoxy, $C_1$-$C_2$-haloalkoxy, $C_3$-$C_4$-cycloalkyl, $C_3$-$C_4$-halocycloalkyl, $C_3$-$C_4$-cycloalkoxy, and $C_3$-$C_4$-halocycloalkoxy, or wherein two $R^A$ are bound to the same carbon atom and together with the carbon atom to which they are bound form a cyclopropane.

* * * * *